United States Patent
Mucke et al.

(10) Patent No.: US 9,101,644 B2
(45) Date of Patent: Aug. 11, 2015

(54) METHODS OF TREATING NEURODEGENERATIVE DISEASE

(75) Inventors: Lennart Mucke, San Francisco, CA (US); Moustapha Cisse, San Francisco, CA (US)

(73) Assignee: THE J. DAVID GLADSTONE INSTITUTES, San Francisco, CA (US)

(*) Notice: Subject to any disclaimer, the term of this patent is extended or adjusted under 35 U.S.C. 154(b) by 0 days.

(21) Appl. No.: 13/881,625

(22) PCT Filed: Nov. 3, 2011

(86) PCT No.: PCT/US2011/059165
§ 371 (c)(1),
(2), (4) Date: May 29, 2013

(87) PCT Pub. No.: WO2012/067839
PCT Pub. Date: May 24, 2012

(65) Prior Publication Data
US 2013/0253041 A1 Sep. 26, 2013

Related U.S. Application Data

(60) Provisional application No. 61/413,879, filed on Nov. 15, 2010.

(51) Int. Cl.
| A61K 48/00 | (2006.01) |
| A61K 31/7088 | (2006.01) |
| G01N 33/68 | (2006.01) |

(52) U.S. Cl.
CPC ........... *A61K 31/7088* (2013.01); *A61K 48/005* (2013.01); *G01N 33/6896* (2013.01); *C12N 2799/027* (2013.01); *G01N 2333/4709* (2013.01); *G01N 2500/02* (2013.01); *G01N 2500/10* (2013.01)

(58) Field of Classification Search
CPC ................................................... A61K 48/005
See application file for complete search history.

(56) References Cited

U.S. PATENT DOCUMENTS

| 6,992,175 B1 | 1/2006 | Fox et al. |
| 7,402,389 B2 * | 7/2008 | Mousses et al. ............ 435/6.14 |
| 2008/0003210 A1 | 1/2008 | Bruckheimer et al. |
| 2008/0213250 A1 | 9/2008 | Hopf et al. |
| 2009/0170769 A1 | 7/2009 | Jin et al. |
| 2010/0120025 A1 | 5/2010 | Mousses et al. |
| 2010/0285001 A1 | 11/2010 | Land et al. |

FOREIGN PATENT DOCUMENTS

WO    WO 2006-056467 A1    6/2006

OTHER PUBLICATIONS

Malenka et al. Nature 2011;469:44-5.*
Chrencik, et al. "Three-dimensional Structure of the EphB2 Receptor in Complex with an Antagonistic Peptide Reveals a Novel Mode of Inhibition", The Journal of Biological Chemistry, 2007, vol. 282 No. 50 pp. 36505-36513.
Cisse, et al. "Reversing EphB2-ephrin-B3 interaction regulates excitatory synapse density by inhibition of postsynaptic MAPK signaling", Nature, 2010, vol. 469, No. 7328 pp. 47-52.
Gong; et al. "Review: disruption of the postsynaptic density in Alzheimer's disease and other neurodegenerative dementias", Journal of Alzheimer's Disease, 2010, vol. 25. No. 7 pp. 547-555.
Grunwald, et al. "Kinase-independent requirement of EphB2 receptors in hippocampal synaptic plasticity", Neuron, 2001, vol. 32 No. 6 pp. 1027-1040.
Henderson, et al. "The receptor tyrosine kinase EphB2 regulates NMDA-dependent synaptic function", Neuron, 2001, vol. 32 No. 6 pp. 1041-1056.
Malenka, et al. "Alzheimer's disease: Recollection of lost memories", Nature, 2011, vol. 469 No. 7328 pp. 44-45.
McClelland, et al. "Reversing EphB2-ephrin-B3 interaction regulates excitatory synapse density by inhibition of postsynaptic MAPK signaling" Proc Natl Acad Sci USA, 2010, vol. 107. No. 19 pp. 8830-8835.
Ondrejcak, et al. "Alzheimer's disease amyloid-beta protein and synaptic function", Neuromolecular Med, 2009, vol. 12. No. 1 pp. 13-26.
Simón, et al. "Early Changes in Hippocampal Eph Receptors Precede the Onset of Memory Decline in Mouse models of Alzheimer's Disease", Journal of Alzheimer's Disease, 2009, vol. 17, pp. 773-786.
Xu, et al. "Peptide EphB2/CTF2 generated by the gamma-secretase processing of EphB2 receptor promotes tyrosine phosphorylation and cell surface localization of N-methyl-D-aspartate receptors", The Journal of Biological Chemistry, 2009, vol. 284. No. 40, pp. 27220-27228.
Bakker et al.; "Reduction of hippocampal hyperactivity improves cognition in amnestic mild cognitive impairment"; Neuron; vol. 74, No. 3, pp. 467-474 (May 10, 2012).
Cheng et al.; "Collagen VI protects neurons against Aβ toxicity"; Nat. Neurosci.; 12 (2): 119 (Feb. 2009).
Meilandt et al.; "Enkephalin Elevations Contribute to Neuronal and Behavioral Impairments in a Transgenic Mouse Model of Alzheimer's Disease"; vol. 28, No. 19, pp. 5007-5017 (May 7, 2008).
Orr et al.; "Astrocytic adenosine receptor A2A and Gs-coupled signaling regulate memory"; Nature Neuroscience; Doi: 10.1038/nn. 3930 (Jan. 26, 2015).
Palop et al.; "Neoronal depletion of calcium-dependent proteins in the dentate gyrus is tightly linked to Alzheimer's disease-related cognitive deficits"; Proc. Natl. Acad. Sci. USA; vol. 100, No. 16, pp. 9572-9577 (Aug. 5, 2003).

(Continued)

*Primary Examiner* — Janice Li
(74) *Attorney, Agent, or Firm* — Bozicevic, Field & Francis LLP; Paula A. Borden

(57) ABSTRACT

The present disclosure provides a method of increasing the level and/or function of an Eph receptor B2 in a neuronal cell; and methods of treating an amyloid-beta-induced neurodegenerative disease in an individual. The present disclosure further provides methods of identifying an agent that increases the level and/or function of an Eph receptor B2 in a neuronal cell.

29 Claims, 16 Drawing Sheets

(56) References Cited

OTHER PUBLICATIONS

Sanchez et al.; "Levetiracetam supresses neuronal network dysfunction and reverses synaptic and cognitive deficits in an Alzheimer's disease model"; Proc. Natl. Acad. Sci. USA; vol. 109, No. 42, pp. E2895-E2903 (Aug. 6, 2012).

Sanchez-Mejia et al.; "Phospholipase A2 reduction ameliorates cognitive deficits in a mouse model of Alzheimer's disease"; Nat. Neurosci.; vol. 11, No. 11, pp. 1311-1318 (Nov. 2008).

Verret et al.; "Inhibitory Interneuron Deficit Links Altered Network Activity and Cognitive Dysfunction in Alzheimer Model"; Cell; vol. 149, No. 3, pp. 708-721 (Apr. 27, 2012).

* cited by examiner

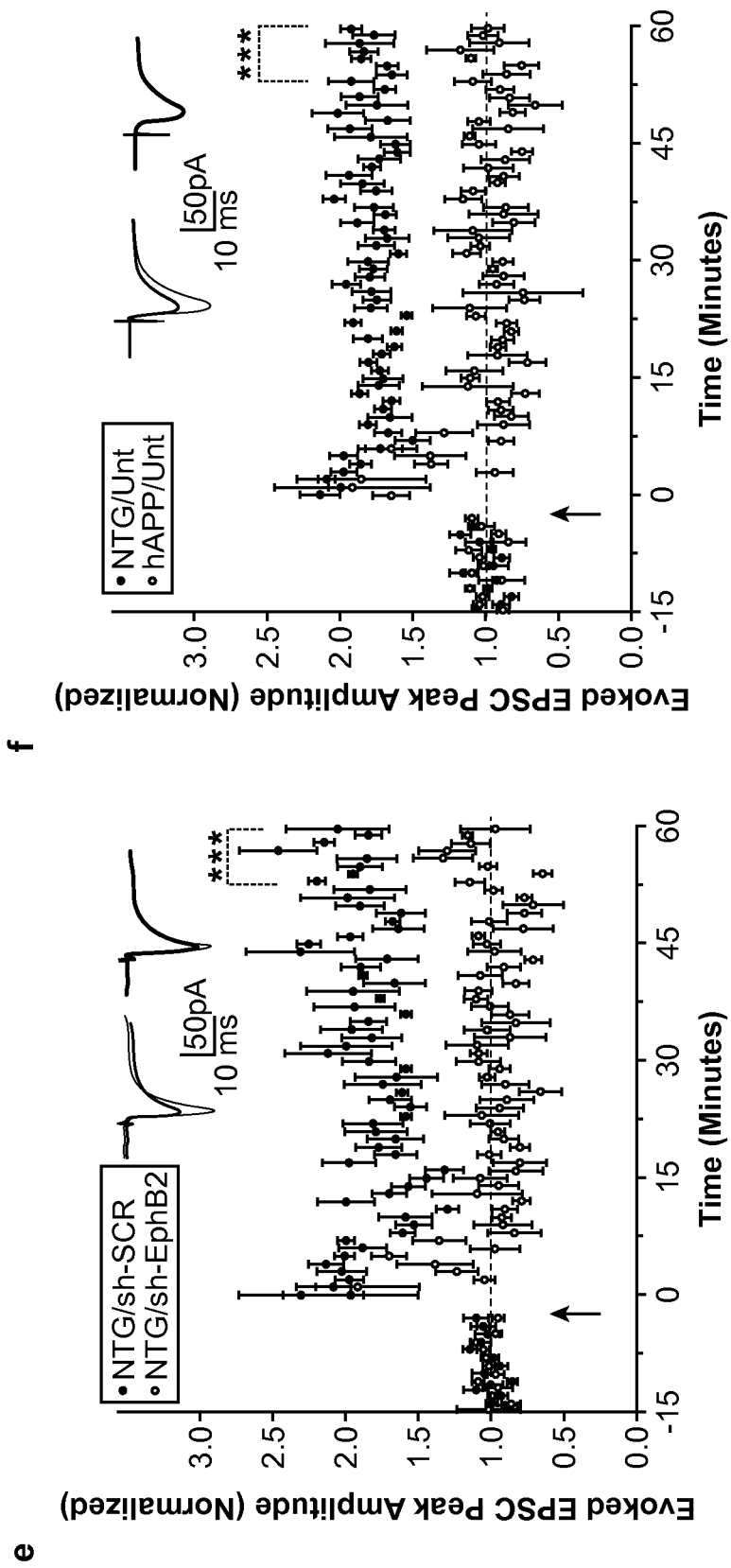
FIG. 3 (Cont. 1)

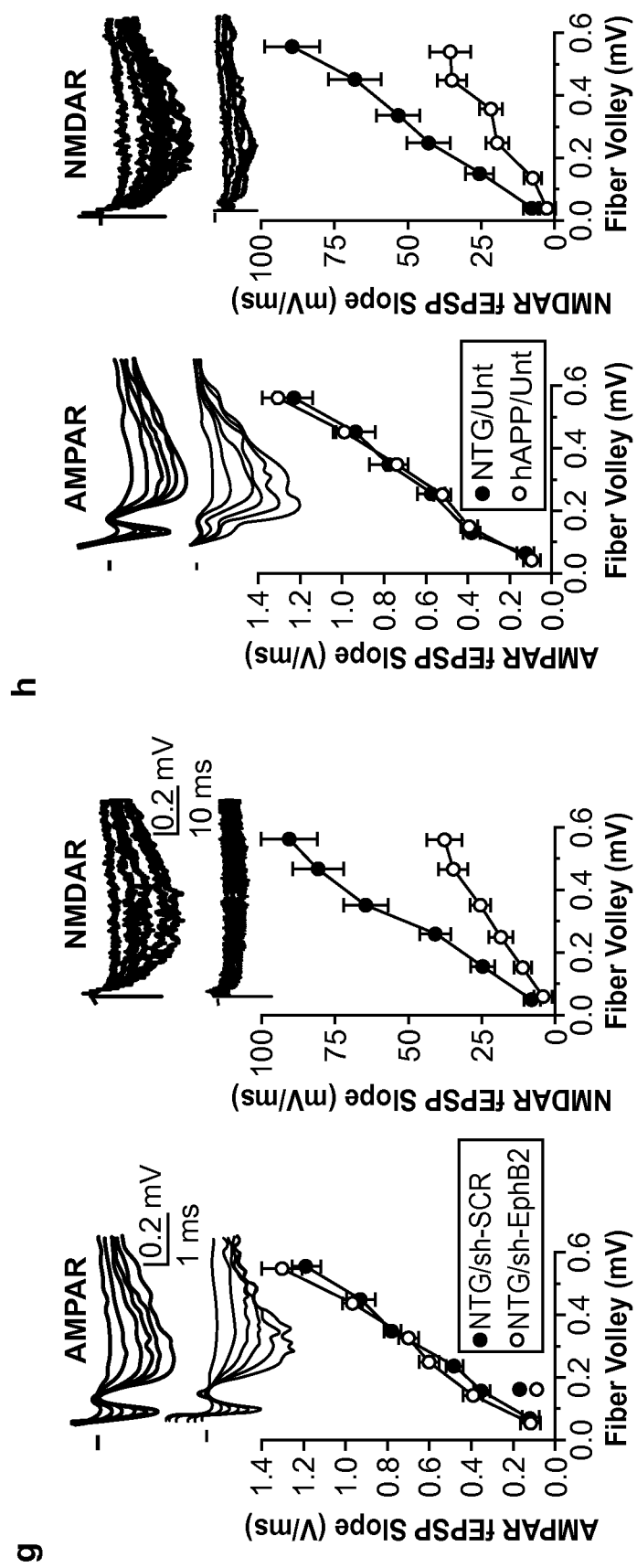
FIG. 3 (Cont. 2)

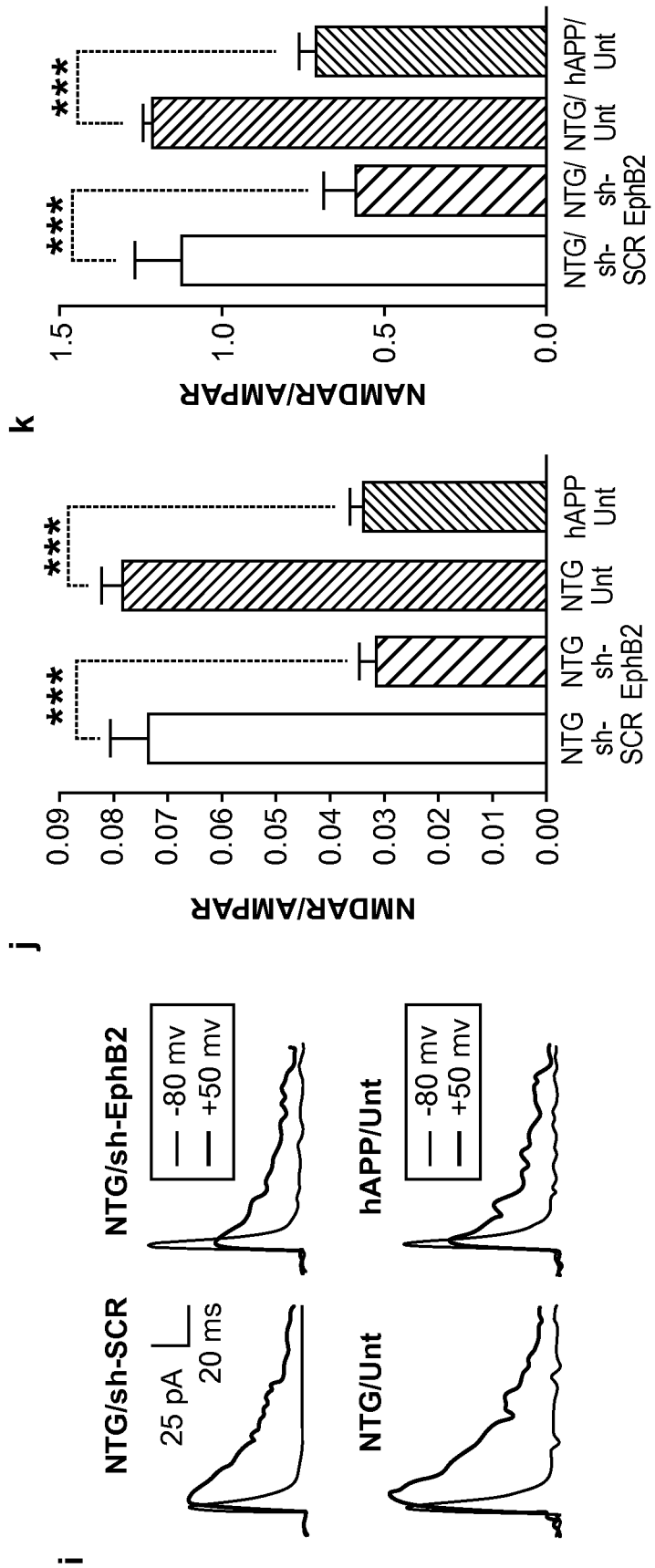
FIG. 3 (Cont. 3)

GenBank NM_004442
*Homo sapiens* EphB2
4869 nt

```
   1 cattctgctg gctgcgcggt ggcggcggct gtgtgtgcgc cgcgccttgc cgccccccct
  61 ggccccccga gcccggggcg cgcgctcccg cccgggccgt ccgggcccg cggcccccg
 121 gcccgagggcc ccgggaagcg cagccatggc tctgcggagg ctgggggccg cgctgctgct
 181 gctgccgctg ctcgccgccg tggtgcatc tggaagaaac gctaatggac tccactacag cgactgctga
 241 gctggctgg atgtgcatc ctccatcagg gtgggaagag gtgagtggct acgatgagaa
 301 catgaacacg atccgcacgt accagtgtgt caacgtgttt gagtcaagcc agaacaactg
 361 gctacggacc aagttttatcc ggcgccgtgg cgcccacgc atccacgtgg agatgaagtt
 421 ttcggtgcgt gactgcagca gcatcccag cgtgcctggc tcctgcaagg agaccttcaa
 481 cctctattac tatgaggctg actttgactc ggccaccaag accttccca actggatgga
 541 gaatccatgg gtgaaggtgg ataccattgc agccgacgag agcttctccc aggtgacct
 601 gggtggcgc gtcatgaaaa tcaacaccga ggtgcggagc ttcggaccctg tgtccgcag
 661 cggcttctac ctggccttcc aggactatgg cggctgcatg cccctcatcg ccgtgcgtgt
 721 cttctaccgc aagtgccccc gcatcatcca gaatggcgcc atcttccagg aaaccctgtc
 781 ggggctgag agcacatcgc tggtggctgc ccggggcagc tgcatcgcca atgcggaaga
 841 ggtggatgta cccatcaagc tctactgtaa cggggacggc gagtggctgg tgcccatcgg
 901 gcgctgcatg tgcaaagcag gcttcgaggc cgttgagaat ggcaccgtct gccgagttg
 961 tccatctggg actttccaag ccaaccaagg ggatgaggcc tgtaccact gtccatcaa
1021 cagccggacc acttctgaag gggccaccaa ctgtgtctgc cgcaatggct actacagagc
1081 agacctggac ccctggaca tgccctgcac cctcatgct ggagtggacc tccgcccgcg aggctgtgat
1141 ttccagtgtc aatgagacct acatcatctg caagagctgt gctccccgcg actccggagg
1201 ccgagaggac ctcgtctaca catcatctg caagagctgt ggctcgggcc gggtgcctg
1261 caccccgctgc gggacaatg tacagtacgc accacgccca ctaggcctga ccgagccacg
1321 catttacatc agtgacctgc tggcccacac ccagtacacc ttcgagatcc aggctgtgaa
1381 cggcgttact gaccagagcc ccttctcgcc tcagttcgcc tctgtgaaca tcaccaccaa
1441 ccaggcagct ccatcggcag tgtccatcat gcatcaggtg agccgcaccg tggacagcat
```

FIG. 6A

```
1501  taccctgtcg  tggtcccagc  cggaccagcc  caatggcgtg  atcctgact   atgagctgca
1561  gtactatgag  aaggagctca  gtgagtacaa  cgccacagcc  ataaaaagcc  ccaccaacac
1621  ggtcaccgtg  cagggcctca  aagccgcgc   catctatgtc  ttccaggtgc  gggcacgcac
1681  cgtggcaggc  tacgggcgct  acagcggcaa  gatgtacttc  cagaccatga  cagaagccga
1741  gtaccagaca  agcatccagg  agaagttgcc  actcatcatc  ggctcctcgg  ccgctggcct
1801  ggtcttcctc  attgctgtgg  ttgtcatcgc  catcgtgtgt  aacagaagac  ggggtttga
1861  gcgtgctgac  tcggagtaca  cggacaagct  gcaacactac  accagtggcc  acatgaccc
1921  agcatgaag   atctacatcg  atcctttcac  ctacgaggac  cccaacgagg  cagtgcggga
1981  gtttgccaag  gaaattgaca  tctcctgtgt  caaaattgag  caggtgatcg  gagcagggga
2041  gtttgcgag   gtctgcagtg  gccacctgaa  gctgccaggc  aagagagaga  tctttgtggc
2101  catcaagacg  ctcaagtcgg  gctacacgga  gaagcagcgc  cgggacttcc  tgagcgaagc
2161  ctccatcatg  ggccagttcg  accatccaca  cgtcatccac  ctggagggtg  tcgtgaccaa
2221  gagcacacct  gtgatgatca  tcaccgagtt  catggagaat  ggctccctgg  actcctttct
2281  ccggcaaaac  gatgggcagt  tcacagttgc  ccagctgttg  gccatgctc   ggggcatcgc
2341  agctgcatg   aagtacctgg  cagacatgaa  ctatgttcac  cgtgacctgg  ctgcccgcaa
2401  catcctcgtc  aacagcaaac  tggtctgcaa  ggtgtcggac  tttgggctct  cacgctttct
2461  agaggacgat  acctcagacc  ccacctaccg  cagttcacc   gcggaaaga   tgtgtggag
2521  ctggacagcc  ccggaagcca  tccagtaccg  gaagttcacc  tcggccagtg  gggacatgac
2581  ctacggcatt  gtcatgtggg  aggtgatgtc  ctatgggag   cggcctact   ccatgactga
2641  caaccaggat  gtaatcaatg  ccattgagca  ggactatcgg  ctgttgcagc  ccatgactg
2701  cccgagcgc   ctgcacaac   tcatgctgga  caagctaga   cctgccgctg  aaggacgca  accacggcc
2761  caagttcggc  caaattgtca  acacgtcct   ctggaccga   caagatgatc  cgcaatccca  acagcctcaa
2821  agccatggcg  ccctctcct   ctgcccgc    cctgccgctg  atcaagatgg  ggcagtacaa  cgatcccga
2881  ctacaccagc  tttaaacacg  tggacagtg   gctggaggcc  ctttgacgtc  gtgtctcaga  ggcagtacaa
2941  ggagagcttc  gccaatgcc   gcttcacctc  tggccaccag  aaaaaatcc   tgaacagtat
3001  ggacattctc  cgggttgggg  tcacttggc   tgaaccagat  tcagtctgtg  gaggtttgac  attcacctgc
3061  ccaggtgatg  cgggcgcaga  cggcgccact  ctcttcctcc  aagccccgcc  cctctgtgcc  caggaggcca
3121  ctcggctcac  ctcttcctcc  aagcccgcc   agccactcgc  caggaggcca  cgggccacgg  ccctcctggt
3181  gctctatcca  ctgcagggc   cggagacg    aacatgcaac  tcaaacgacg  gaagaaccaa
3241  gcgtgccag   ccacgagacg  tcaccaagaa  acatgcaac   tcaaacgacg  gaaaaaaaa
```

FIG. 6B

```
3301 gggaatggga aaaagaaaa cagatcctgg gaggggcgg gaaatacaag gaatattt
3361 taaagaggat tctcataagg aaagcaatga ctgttcttgc ggggataaa aaagggcttg
3421 ggagattcat gcgatgtgtc caatcggaga caaagcagt ttctctccaa ctccctctgg
3481 gaaggtgacc tggccagagc caagaacac tttcagaaaa acaaatgtga agggagaga
3541 cagggccgc cctggctcc tgtccctgct gctcctctag gcctcactca acaaccaagc
3601 gcctggagga cgggacagat ggacagacag ccaccctgag aacccctctg ggaaaatcta
3661 ttcctgccac cactgggcaa acagaagaat ttttctgtct ttggagagta ttttagaaac
3721 tccaatgaaa gacactgttt ctcctgttgg ctcacagggc tgaaagggc ttttgtcctc
3781 ctgggtcagg gagaacgcgg ggacccaga aggtcagcc ttcctgagga tggcaaccc
3841 ccagtctgc agctccaggt acatatcacg cgcacagcct ggcagcctgg cctcctggt
3901 gcccactccc gccagcccct gcctcgagga ctgatactgc agtgactgcc gtcagctccg
3961 actgccgctg agaagggttg atcctgcatc tgggttgt tacagcaatt cctgactcg
4021 gggtattt ggtcacagg tggttttggt gacaatgaag tgtttgttgg gtgttt
4081 gttt tgt ttttttaat acacttg ttaggggtt acatttccta cctttgagg
4141 acttgatcct tctccaggaa gaagtgctt tctgcttact gacttaggca atacacaag
4201 gcgagatt tatatgcaca tttctggatt ttttatacg gttttcattg acactcttcc
4261 ctcctcccac ctgccaccag gcctcaccaa agcccactgc catgggcca tctgggccat
4321 tcagagactg gagtgagatt tgggtgtga ggggaggcg ccaaggtgga ggagcttccc
4381 actccagac tgttgatgaa agggacagat tgaggaggaa gtgggctctg agcctgcagg
4441 gctgaagtc cttgagggct ctttgagggc atcggaggcc aggacccgga ctatctagta cttcccctct
4501 aaataggccc accaggctgc atcggaggcc aggacccgga caagcatgcc tcttcccttc tgtatacctg
4561 gggagcctaa accaggctgc atcggaggcc aggacccgga caagcatgcc tcttcccttc cctggagaga
4621 ccctccagag ggtgcgctca gagacacggg accctccttcc ccccaccaga cctttgctgg gcctaaaggt
4681 aagtgtgtga tttctctccc acctccttcc ccccaccaga cctttgctgg gcctaaaggt
4741 cttggccatg gggacgccct cagtctaggg atctgccac agactcctc ctgtgaacca
4801 acacagacac ccaagcagag caatcagtta gtgaattgaa tggaaataaa cgctttagtt
4861 ataatatga (SEQ ID NO:1)
```

FIG. 6C

```
Seq1 = Homo sapiens EphB2
Seq2 = Rattus norvegicus EphB2
Seq3 = Pan troglodytes EphB2 seq1    ------------MALRRLG------AALLLPLIAAVEET------LMDSTTATAELGW    35
seq2    ------------MAVRRLG------AALLLPLIAAVEET------LMDSTTATAELGW    35
seq3    MEDLSCLGLCEQNLGYILRDGLGPRGFLQLIESGEASGAQDGPETLMDSTTATAELGW    60
                    ..  ..**       ..* *             ************ seq1    MVHPPSGWEEVSGYDENMNTIRTYQVCNVFESSQNNWLRTKFIRRRGAHRIHVEMKFSVR    95
seq2    MVHPPSGWEEVSGYDENMNTIRTYQVCNVFESSQNNWLRTKFIRRRGAHRIHVEMKFSVR    95
seq3    MVHPPSGWEEVSGYDENMNTIRTYQVCNVFESSQNNWLRTKFIRRRGAHRIHVEMKFSVR   120
        ************************************************************ seq1    DCSSIPSVPGSCKETFNLYYYEADFDSATKTFPNWMENPWVKVDTIAADESFSQVDLGGR   155
seq2    DCSSIPSVPGSCKETFNLYYYEADFDLATKTFPNWMENPWVKVDTIAADESFSQVDLGGR   155
seq3    DCSSIPSVPGSCKETFNLYYYEADFDSATKTFPNWMENPWVKVDTIAADESFSQVDLGGR   180
        ************************  ********************************* seq1    VMKINTEVRSFGPVSRSGFYLAFQDYGGCMSLIAVRVFYRKCPRIIQNGAIFQETLSGAE   215
seq2    VMKINTEVRSFGPVSRNGFYLAFQDYGGCMSLIAVRVFYRKCPRVIQNGAIFQETLSGAE   215
seq3    VMKINTEVRSFGPVSRSGFYLAFQDYGGCMSLIAVRVFYRKCPRIIQNGAIFQETLSGAE   240
        **************.***********************:************* seq1    STSLVAARGSCIANAEEVDVPIKLYCNGDGEWLVPIGRCMCKAGFEAVENGTVCRGCPSG   275
seq2    STSLVAARGSCIANAEEVDVPIKLYCNGDGEWLVPIGRCMCKAGFEAVENGTVCRGCPSG   275
seq3    STSLVAARGSCIANAEEVDVPIKLYCNGDGEWLVPIGRCMCKAGFEAVENGTVCRGCPSG   300
        ************************************************************ seq1    TFKANQGDEACTHCPINSRTTSEGATNCVCRNGYYRADLDPLDMPCTTIPSAPQAVISSV   335
seq2    TFKANQGDEACTHCPINSRTTSEGATNCVCRNGYYRADLDPLDMPCTTIPSAPQAVISSV   335
seq3    TFKANQGDEACTHCPINSRTTSEGATNCVCRNGYYRADLDPLDMPCTTIPSAPQAVISSV   360
        ************************************************************
```

FIG. 7A

```
seq1    NETSLMLEWTPPRDSGGREDLVYNIICKSCGSGRGACTRCGDNVQYAPRQLGLTEPRIYI    395
seq2    NETSLVLEWTPPRDSGGREDLVYNIICKSCGSGRGACTRCGDNVQYAPRQLGLTEPRIYI    395
seq3    NETSLMLEWTPPRDSGGREDLVYNIICKSCGSGRGACTRCGDNVQYAPRQLGLTEPRIYI    420
        **:******************************************************* seq1    SDLLAHTQYTFEIQAVNGVTDQSPFSPQFASVNITTNQAAPSAVSIMHQVSRTVDSITLS    455
seq2    SDLLAHTQYTFEIQAVNGVTDQSPFSPQFASVNITTNQAAPSAVSIMHQVSRTVDSITLS    455
seq3    SDLLAHTQYTFEIQAVNGVTDQSPFSPQFASVNITTNQAAPSAVSIMHQVSRTVDSITLS    480
        ************************************************************ seq1    WSQPDQPNGVILDYELQYYEKELSEYNATAIKSPTNTVTVQGLKAGAIYVFQVRARTVAG    515
seq2    WSQPDQPNGVILDYELQYYEKELSEYNATAIKSPTNTVTVQGLKAGTIYVFQVRARTVAG    515
seq3    WSQPDQPNGVILDYELQYYEKELSEYNATAIKSPTNTVTVQGLKAGAIYVFQVRARTVAG    540
        ********************************************:*********** seq1    YGRYSGKMYFQTMTEAEYQTSIQEKLPLIIGSSAAGLVFLIAVVIAIVCNRRRGFERAD    575
seq2    YGRYSGKMYFQTMTEAEYQTSIKEKLPLIVGSSAAGVVFVIAVVIAIVCNRR-GFERAD    574
seq3    YGRYSGKMYFQTMTEAEYQTSIQEKLPLIIGSSAAGLVFLIAVVIAIVCNRRRGFERAD    600
        *******************:***:**::*********  ***** seq1    SEYTDKLQHYTSGHMTPGMKIYIDPFTYEDPNEAVREFAKEIDISCVKIEQVIGAGEFGE    635
seq2    SEYTDKLQHYTSGHMTPGMKIYIDPFTYEDPNEAVREFAKEIDISCVKIEQVIGAGEFGE    634
seq3    SEYTDKLQHYTSGHMTPGMKIYIDPFTYEDPNEAVREFAKEIDISCVKIEQVIGAGEFGE    660
        ************************************************************ seq1    VCSGHLKLPGKREIFVAIKTLKSGYTEKQRRDFLSEASIMGQFDHPNVIHLEGVVTKSTP    695
seq2    VCSGHLKLPGKREIFVAIKTLKSGYTEKQRRDFLSEASIMGQFDHPNVIHLEGVVTKSTP    694
seq3    VCSGHLKLPGKREIFVAIKTLKSGYTEKQRRDFLSEASIMGQFDHPNVIHLEGVVTKSTP    720
        ************************************************************ seq1    VMIITEFMENGSLDSFLRQNDGQFTVIQLVGMLRGIAAGMKYLADMNYVHRDLAARNILV    755
seq2    VMIITEFMENGSLDSFLRQNDGQFTVIQLVGMLRGIAAGMKYLADMNYVHRDLAARNILV    754
seq3    VMIITEFMENGSLDSFLRQNDGQFTVIQLVGMLRGIAAGMKYLADMNYVHRDLAARNILV    780
        ************************************************************
```

FIG. 7B

```
seq1      NSNLVCKVSDFGLSRFLEDDTSDPTYTSALGGKIPIRWTAPEAIQYRKFTSASDVWSYGI 815
seq2      NSNLVCKVSDFGLSRFLEDDTSDPTYTSALGGKIPIRWTAPEAIQYRKFTSASDVWSYGI 814
seq3      NSNLVCKVSDFGLSRFLEDDTSDPTYTSALGGKIPIRWTAPEAIQYRKFTSASDVWSYGI 840
          ************************************************************ seq1      VMWEVMSYGERPYWDMTNQDVINAIEQDYRLPPPMDCPSALHQLMLDCWQKDRNHRPKFG 875
seq2      VMWEVMSYGERPYWDMTNQDVINAIEQDYRLPPPMDCPSALHQLMLDCWQKDRNHRPKFG 874
seq3      VMWEVMSYGERPYWDMTNQDVINAIEQDYRLPPPMDCPSALHQLMLDCWQKDRNHRPKFG 900
          ************************************************************ seq1      QIVNTLDKMIRNPNSLKAMAPLSSGINLPLLDRTIPDYTSFNTVDEWLEAIKMGQYKESF 935
seq2      QIVNTLDKMIRNPNSLKAMAPLSSGINLPLLDRTIPDYTSFNTVDEWLEAIKMGQYKESF 934
seq3      QIVNTLDKMIRNPNSLKAMAPLSSGINLPLLDRTIPDYTSFNTVDEWLEAIKMGQYKESF 960
          ************************************************************ seq1      ANAGFTSFDVVSQMMEDILRVGVTLAGHQKKILNSIQVMRAQMNQIQSVEV  987 (SEQ ID NO:2)
seq2      TNAGFTSFDVVSQMMEDILRVGVTLAGHQKKILNSIQVMRAQMNQIQSVEV  986 (SEQ ID NO:3)
seq3      ANAGFTSFDVVSQMMEDILRVGVTLAGHQKKILNSIQVMRAQMNQIQSVEV 1012 (SEQ ID NO:4)
          : ************************************************
```

FIG. 7C

METHODS OF TREATING NEURODEGENERATIVE DISEASE

CROSS-REFERENCE

This application claims the benefit of U.S. Provisional Patent Application No. 61/413,879, filed Nov. 15, 2010, which application is incorporated herein by reference in its entirety.

STATEMENT REGARDING FEDERALLY SPONSORED RESEARCH

This invention was made with government support under Grant Nos. AG011385, AG022074, and NS041787 awarded by the National Institutes of Health. The government has certain rights in the invention.

BACKGROUND

Soluble amyloid-β (Aβ) oligomers may contribute to learning and memory deficits in Alzheimer's disease (AD) by inhibiting N-methyl-D-aspartic acid (NMDA) receptor (NMDAR)-dependent long-term potentiation (LTP), a process widely considered to underlie memory formation. In AD, hippocampal levels of NMDAR subunits are reduced[5], and protein levels and phosphorylation status of NMDAR subunits NR1, NR2A, and NR2B correlate with cognitive performance. Human amyloid precursor protein (hAPP) transgenic mice with high levels of Aβ oligomers in the brain also have reduced hippocampal levels of tyrosine-phosphorylated NMDARs and key components of NMDAR-dependent signaling pathways. Notably, AD patients and hAPP mice have hippocampal depletions of the receptor tyrosine kinase EphB2, which regulates NMDAR trafficking and function through direct interaction with NMDARs and Src-mediated tyrosine phosphorylation. EphB2 regulates NMDAR-dependent $Ca^{2+}$ influx and downstream transcription factors involved in long-term potentiation (LTP) formation, such as Fos, which is depleted in the dentate gyrus (DG) of hAPP mice.

LITERATURE

U.S. Patent Publication No. 2008/0213250; Henderson et al. (2001) *Neuron* 32:1041; Grunwald et al. (2001) *Neuron* 32:1027; Chrencik et al. (2007) *J. Biol. Chem.* 282:36505; Simón et al. (2009) *J. Alzheimer's Disease* 17:773.

SUMMARY OF THE INVENTION

The present disclosure provides a method of increasing the level and/or function of an Eph receptor B2 in a neuronal cell; and methods of treating an amyloid-beta-induced neurodegenerative disease in an individual. The present disclosure further provides methods of identifying an agent that increases the level and/or function of an Eph receptor B2 in a neuronal cell.

BRIEF DESCRIPTION OF THE DRAWINGS

FIGS. 6A-C provide a nucleotide sequence encoding a EphB2 polypeptide.

FIG. 7A-C provide amino acid sequences of EphB2 polypeptides.

DEFINITIONS

Figure 1:
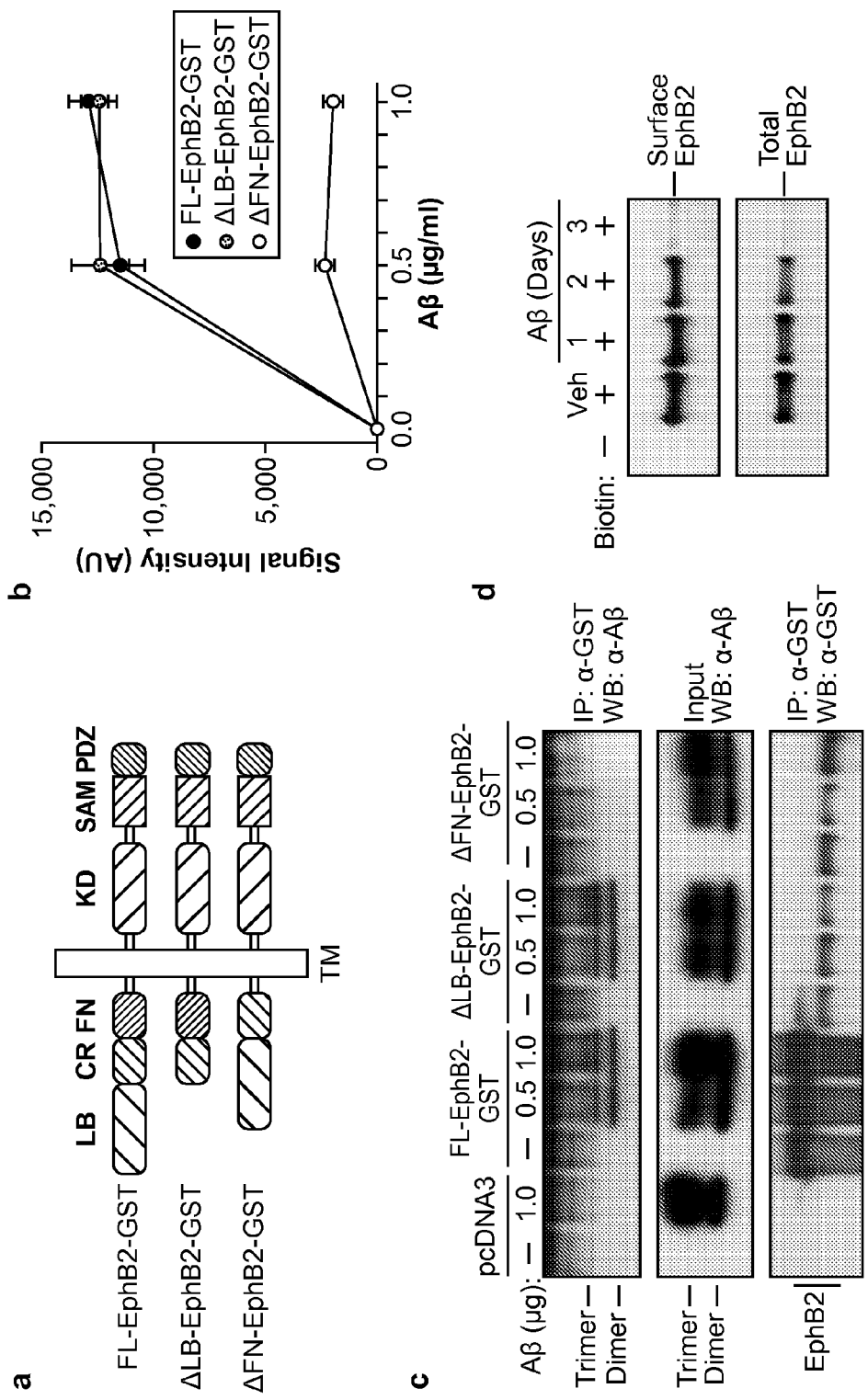
FIGS. 1A-I depict binding of Aβ oligomers to the fibronectin (FN) repeats domain of EphB2 and the effect of binding of Aβ oligomers to the FN repeats domain of EphB2 in the proteasome.
Figure 1:
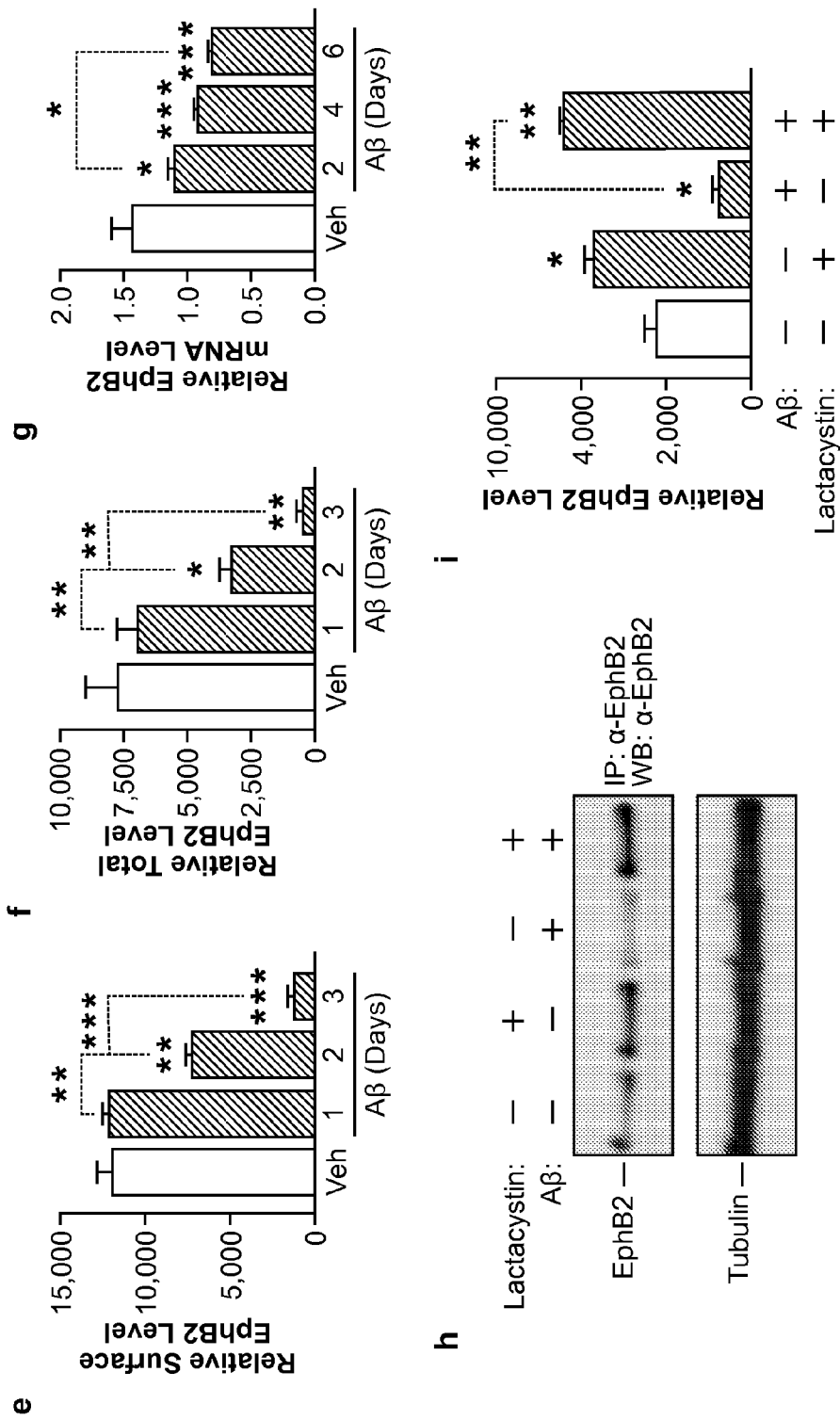

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The terms "nucleic acid" and "polynucleotide" are used interchangeably herein and refer to a polymeric form of nucleotides of any length, either deoxyribonucleotides or ribonucleotides, or analogs thereof. Non-limiting examples of polynucleotides include linear and circular nucleic acids, messenger RNA (mRNA), cDNA, recombinant polynucleotides, vectors, probes, and primers.

The term "operably linked" refers to functional linkage between molecules to provide a desired function. For example, "operably linked" in the context of nucleic acids refers to a functional linkage between nucleic acids to provide a desired function such as transcription, translation, and the like, e.g., a functional linkage between a nucleic acid expression control sequence (such as a promoter, signal sequence, or array of transcription factor binding sites) and a second polynucleotide, wherein the expression control sequence affects transcription and/or translation of the second polynucleotide.

The term "genetic modification" and refers to a permanent or transient genetic change induced in a cell following introduction of new nucleic acid (i.e., nucleic acid exogenous to the cell). Genetic change ("modification") can be accomplished by incorporation of the new nucleic acid into the genome of the host cell, or by transient or stable maintenance of the new nucleic acid as an extrachromosomal element. Where the cell is a eukaryotic cell, a permanent genetic change can be achieved by introduction of the nucleic acid into the genome of the cell. Suitable methods of genetic modification include viral infection, transfection, conjugation, protoplast fusion, electroporation, particle gun technology, calcium phosphate precipitation, direct microinjection, and the like.

As used herein, the term "exogenous nucleic acid" refers to a nucleic acid that is not normally or naturally found in and/or produced by a cell in nature, and/or that is introduced into the cell (e.g., by electroporation, transfection, infection, lipofection, or any other means of introducing a nucleic acid into a cell).

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc. In some embodiments, the individual is a human. In some embodiments, the individual is a murine.

A "therapeutically effective amount" or "efficacious amount" of a nucleic acid means the amount of a nucleic acid that, when administered to a mammal or other subject for treating a disease, is sufficient to effect such treatment for the disease. The "therapeutically effective amount" will vary depending on the compound or the cell, the disease and its severity and the age, weight, etc., of the subject to be treated.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an EphB2 receptor" includes a plurality of such receptors and reference to "the EphB2 nucleic acid" includes reference to one or more EphB2 nucleic acids and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides a method of increasing the level and/or function of an Eph receptor B2 in a neuronal cell; and methods of treating an amyloid-beta-induced neurodegenerative disease in an individual. The present disclosure further provides methods of identifying an agent that increases the level and/or function of an Eph receptor B2 in a neuronal cell.

Methods for Increasing the Level and/or Function of EPHB2

The present disclosure provides a method of increasing the level and/or function of an Eph receptor B2 in a neuronal cell. A subject method generally involves introducing into a neuronal cell an exogenous nucleic acid comprising a nucleotide sequence encoding an ephrin type-B receptor 2 (EphB2) polypeptide, where the nucleic acid enters the neuronal cell, the encoded EphB2 polypeptide is produced in the neuronal cell, and the level and/or function of EphB2 is thereby increased in the cell.

A subject method can be used to treat an amyloid beta-associated or amyloid beta-induced neurodegenerative disease in an individual. A subject method of treating an amyloid beta-induced neurodegenerative disease in an individual generally involves administering to the individual an effective amount of an exogenous nucleic acid comprising a nucleotide sequence encoding an EphB2 polypeptide, where the nucleic acid enters a neuronal cell in the individual, the encoded EphB2 polypeptide is produced in the neuronal cell, and the level and/or function of EphB2 is thereby increased in the cell. Increasing the level and/or function of EphB2 in a neuronal cell in the individual treats the amyloid beta-induced neurodegenerative disease in the individual.

In some embodiments, a subject method is effective to increase the level of EphB2 in a neuronal cell by at least about 5%, at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or greater than 10-fold, compared to the level of EphB2 in the cell before an exogenous nucleic acid encoding EphB2 polypeptide is introduced into the cell.

In some embodiments, a subject method is effective to increase a function of EphB2 in a neuronal cell by at least about 5%, at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or greater than 10-fold, compared to the level of the function of the EphB2 in the neuronal cell before an exogenous nucleic acid encoding EphB2 polypeptide is introduced into the cell.

Functions of EphB2 that can be increased using a subject method include: 1) increasing tyrosine kinase activity in phosphorylating an NMDA receptor in the cell, thereby increasing NMDA receptor function; 2) increasing NMDA receptor activity in a tyrosine kinase-independent manner; and 3) modulating EphB2 interactions with factors other than NMDA.

In some embodiments, a subject method reduces binding of Aβ to EphB2 in a neuronal cell. For example, in some embodiments, a subject method reduces binding of Aβ to EphB2 in a neuronal cell by at least about 5%, at least about 10%, at least about 15%, at least about 20%, at least about 25%, at least about 30%, at least about 40%, at least about 50%, at least about 75%, or more than 75%, compared to the level of binding of Aβ to EphB2 in the neuronal cell before an exogenous nucleic acid encoding EphB2 polypeptide is introduced into the cell.

As noted above, a subject method of treating an amyloid beta-induced neurodegenerative disease in an individual generally involves administering to the individual an effective amount of an exogenous nucleic acid comprising a nucleotide sequence encoding an EphB2 polypeptide. An exogenous nucleic acid comprising a nucleotide sequence encoding an EphB2 polypeptide is also referred to herein as "an exogenous EphB2 nucleic acid." In some embodiments, an "effective amount" of an exogenous EphB2 nucleic acid is an amount that is effective to increase cognitive function in an individual. In some embodiments, an "effective amount" of an exogenous EphB2 nucleic acid is an amount that is effective to ameliorate one or more adverse symptom of an amyloid beta-induced neurodegenerative disease in an individual.

In some embodiments, an effective amount of an exogenous EphB2 nucleic acid is an amount reduces an adverse symptom, abnormality, or pathology associated with Alzheimer's disease (AD), such as formation of neurofibrillary tangles or Aβ deposits, by at least about 10%, at least about 20%, at least about 30%, at least about 50%, at least about 60%, at least about 70%, at least about 80%, at least about 90% or more. In other embodiments, an effective amount of an exogenous EphB2 nucleic acid is an amount that improves a parameter that is in decline in individuals with AD, such as memory or cognitive function, by at least about 10%, at least about 20%, at least about 30%, at least about 50%, at least about 60%, at least about 70%, at least about 80%, at least about 90% or more, such that the decline in one of these parameters is at least slowed.

The terms "EphB2," "ephrin type-B receptor 2," and "Eph receptor B2" are used interchangeably herein to refer to a receptor tyrosine kinase that functions as a receptor for an ephrin type B ligand. EphB2 polypeptides are known in the art, as are nucleotide sequences encoding EphB2 polypeptides. EphB2 polypeptides are described in, e.g., Thanos et al. (1999) *Science* 283:833. Amino acid sequences of EphB2 polypeptides are known in the art; see, e.g., GenBank Accession Nos. NP_004433 (*Homo sapiens* EphB2), NP_034272 (*Mus musculus* EphB2), NP_001120791 (*Rattus norvegicus* EphB2), and XP_513189.2 (*Pan troglodytes* EphB2). In some embodiments, an EphB2 polypeptide comprises an amino acid sequence having at least about 80%, at least about 85%, at least about 90%, at least about 95%, at least about 98%, at least about 99%, or 100%, amino acid sequence identity to a contiguous stretch of from about 100 amino acids (aa) to about 150 aa, from about 150 aa to about 200 aa, from about 200 aa to about 250 aa, from about 250 aa to about 300 aa, from about 300 aa to about 400 aa, from about 400 aa to about 500 aa, from about 500 aa to about 600 aa, from about 600 aa to about 700 aa, from about 700 aa to about 800 aa, from about 800 aa to about 900 aa, or from about 900 aa to 987 aa, of an amino acid sequence depicted in FIGS. 7A-C.

In some embodiments, an EphB2 polypeptide comprises an amino acid sequence having at least about 80%, at least about 85%, at least about 90%, at least about 95%, at least about 98%, at least about 99%, or 100%, amino acid sequence identity to a contiguous stretch of from about 100 amino acids (aa) to about 150 aa, from about 150 aa to about 200 aa, from about 200 aa to about 250 aa, from about 250 aa to about 300 aa, from about 300 aa to about 400 aa, from about 400 aa to about 500 aa, from about 500 aa to about 600 aa, from about 600 aa to about 700 aa, from about 700 aa to about 800 aa, from about 800 aa to about 900 aa, or from about 900 aa to 987 aa, of the amino acid sequence set forth in SEQ ID NO:2 (*Homo sapiens* EphB2; GenBank Accession No. NP_004433) and depicted in FIGS. 7A-C.

In some embodiments, an EphB2 polypeptide comprises one or more of: 1) a fibronectin (FN) domain, e.g., a domain corresponding to amino acids 325-431 and 436-527 of the amino acid sequence set forth in SEQ ID NO:2; 2) a ligand-binding domain, e.g., a domain corresponding to amino acids 20-197 of the amino acid sequence set forth in SEQ ID NO:2; 3) a catalytic (tyrosine kinase) domain, e.g., a domain corresponding to amino acids 617-885 of the amino acid sequence set forth in SEQ ID NO:2; and a sterile alpha motif (SAM) domain, e.g., a domain corresponding to amino acids 913-976 of the amino acid sequence set forth in SEQ ID NO:2.

An EphB2 nucleic acid is a nucleic acid that comprises a nucleotide sequence encoding an EphB2 polypeptide, or a biologically active fragment thereof. Nucleotide sequences encoding EphB2 polypeptides are known in the art. See, e.g., GenBank Accession Nos. NM_004442 (*Homo sapiens* EphB2-encoding nucleotide sequence), NM_010142 (*Mus musculus* EphB2-encoding nucleotide sequence), NM_001127319 (*Rattus norvegicus* EphB2-encoding nucleotide sequence), and XM_513189.2 (*Pan troglodytes* EphB2-encoding nucleotide sequence).

In some embodiments, a suitable EphB2 nucleic acid comprises a nucleotide sequence having at least about 80%, at least about 85%, at least about 90%, at least about 95%, at least about 98%, at least about 99%, or 100%, nucleotide sequence identity to a contiguous stretch of from about 300 nucleotides (nt) to about 500 nt, from about 500 nt to about 750 nt, from about 750 nt to about 1000 nt, from about 1000 nt to about 1500 nt, from about 1500 nt to about 2000 nt, from about 2000 nt to about 3000 nt, from about 3000 nt to about 4000 nt, from about 4000 nt to about 4500 nt, or from about 4500 nt to 4869 nt, of a nucleotide sequence depicted in FIGS. 6A and 6B. In some embodiments, a suitable EphB2 nucleic acid comprises a nucleotide sequence having at least about 80%, at least about 85%, at least about 90%, at least about 95%, at least about 98%, at least about 99%, or 100%, nucleotide sequence identity to a contiguous stretch of from about 300 nucleotides (nt) to about 500 nt, from about 500 nt to about 750 nt, from about 750 nt to about 1000 nt, from about 1000 nt to about 1500 nt, from about 1500 nt to about 2000 nt, from about 2000 nt to about 3000 nt, from about 3000 nt to about 4000 nt, from about 4000 nt to about 4500 nt, or from about 4500 nt to 4869 nt, of the nucleotide sequence set forth in SEQ ID NO:1 (*Homo sapiens* EphB2; GenBank Accession No. NM_004442) and depicted in FIGS. 6A-C.

In some embodiments, a suitable EphB2 nucleic acid comprises a nucleotide sequence encoding an amino acid sequence having at least about 80%, at least about 85%, at least about 90%, at least about 95%, at least about 98%, at least about 99%, or 100%, amino acid sequence identity to a contiguous stretch of from about 100 amino acids (aa) to about 150 aa, from about 150 aa to about 200 aa, from about 200 aa to about 250 aa, from about 250 aa to about 300 aa, from about 300 aa to about 400 aa, from about 400 aa to about 500 aa, from about 500 aa to about 600 aa, from about 600 aa to about 700 aa, from about 700 aa to about 800 aa, from about 800 aa to about 900 aa, or from about 900 aa to 987 aa, of the amino acid sequence set forth in SEQ ID NO:2 (*Homo sapiens* EphB2; GenBank Accession No. NP_004433).

An exogenous EphB2 nucleic acid can be a recombinant expression vector, where suitable vectors include, e.g., recombinant retroviruses, lentiviruses, and adenoviruses; retroviral expression vectors, lentiviral expression vectors, nucleic acid expression vectors, and plasmid expression vectors. In some cases, the exogenous EphB2 nucleic acid is integrated into the genome of a neuronal cell. In other cases, the exogenous EphB2 nucleic acid persists in an episomal state in the neuronal cell. In some cases, an endogenous, natural version of an exogenous EphB2 nucleic acid exists in the neuronal cell; and introduction of the exogenous EphB2 nucleic acid increases the level and/or function of EphB2 in the cell. In other cases, the exogenous EphB2 nucleic acid encodes an EphB2 polypeptide having an amino acid sequence that differs by one or more amino acids from an EphB2 polypeptide encoded by an endogenous EphB2-encoding nucleic acid within the host neuronal cell.

Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:8186, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641648, 1999; Ali et al., Hum Mol Genet. 5:591594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Numerous suitable expression vectors are known to those of skill in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology*, 153:516-544).

In some embodiments, an EphB2-encoding nucleotide sequence is operably linked to a control element, e.g., a transcriptional control element, such as a promoter. The transcriptional control element is functional in a eukaryotic cell, e.g., a mammalian cell. Suitable transcriptional control elements include promoters and enhancers. In some embodiments, the promoter is constitutively active. In other embodiments, the promoter is inducible.

Non-limiting examples of suitable eukaryotic promoters (promoters functional in a eukaryotic cell) include CMV immediate early, HSV thymidine kinase, early and late SV40, long terminal repeats (LTRs) from retrovirus, and mouse metallothionein-I.

In some embodiments, the EphB2-encoding nucleotide sequence is operably linked to a neuron-specific control element (e.g., a promoter, an enhancer), a microglia-specific transcriptional control element, an oligocyte-specific transcriptional control element, or an astroglia-specific transcriptional control element.

Neuron-specific promoters and other control elements (e.g., enhancers) are known in the art. Suitable neuron-specific control sequences include, but are not limited to, a neuron-specific enolase (NSE) promoter (see, e.g., EMBL HSENO2, X51956); an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al. (1987) Cell 51:7-19); a serotonin receptor promoter (see, e.g., GenBank S62283); a tyrosine hydroxylase promoter (TH) (see, e.g., Nucl. Acids. Res. 15:2363-2384 (1987) and Neuron 6:583-594 (1991)); a GnRH promoter (see, e.g., Radovick et al., Proc. Natl. Acad. Sci. USA 88:3402-3406 (1991)); an L7 promoter (see, e.g., Oberdick et al., Science 248:223-226 (1990)); a DNMT promoter (see, e.g., Bartge et al., Proc. Natl. Acad. Sci. USA 85:3648-3652 (1988)); an enkephalin promoter (see, e.g., Comb et al., EMBO J. 17:3793-3805 (1988)); a myelin basic protein (MBP) promoter; and a CMV enhancer/platelet-derived growth factor-β promoter (see, e.g., Liu et al. (2004) *Gene Therapy* 11:52-60).

Selection of the appropriate vector and promoter is well within the level of ordinary skill in the art. The expression vector may also contain a ribosome binding site for translation initiation and a transcription terminator. The expression vector may also include appropriate sequences for amplifying expression.

Examples of suitable viral vectors include, but are not limited, viral vectors based on retroviruses (including lentiviruses); adenoviruses; and adeno-associated viruses. An example of a suitable retrovirus-based vector is a vector based on murine moloney leukemia virus (MMLV); however, other recombinant retroviruses may also be used, e.g., Avian Leukosis Virus, Bovine Leukemia Virus, Murine Leukemia Virus (MLV), Mink-Cell focus-Inducing Virus, Murine Sarcoma Virus, Reticuloendotheliosis virus, Gibbon Abe Leukemia Virus, Mason Pfizer Monkey Virus, or Rous Sarcoma Virus, see, e.g., U.S. Pat. No. 6,333,195.

In other cases, the retrovirus-based vector is a lentivirus-based vector, (e.g., Human Immunodeficiency Virus-1 (HIV-1); Simian Immunodeficiency Virus (SIV); or Feline Immunodeficiency Virus (FIV)), See, e.g., Johnston et al., (1999), Journal of Virology, 73(6):4991-5000 (FIV); Negre D et al., (2002), Current Topics in Microbiology and Immunology, 261:53-74 (SIV); Naldini et al., (1996), Science, 272:263-267 (HIV).

The recombinant retrovirus may comprise a viral polypeptide (e.g., retroviral env) to aid entry into the target cell. Such viral polypeptides are well-established in the art, see, e.g., U.S. Pat. No. 5,449,614. The viral polypeptide may be an amphotropic viral polypeptide, e.g., amphotropic env, which aids entry into cells derived from multiple species, including cells outside of the original host species. The viral polypeptide may be a xenotropic viral polypeptide that aids entry into cells outside of the original host species. In some embodiments, the viral polypeptide is an ecotropic viral polypeptide, e.g., ecotropic env, which aids entry into cells of the original host species.

Examples of viral polypeptides capable of aiding entry of retroviruses into cells include but are not limited to: MMLV amphotropic env, MMLV ecotropic env, MMLV xenotropic env, vesicular stomatitis virus-g protein (VSV-g), HIV-1 env, Gibbon Ape Leukemia Virus (GALV) env, RD114, FeLV-C, FeLV-B, MLV 10A1 env gene, and variants thereof, including chimeras. See e.g., Yee et al., (1994), Methods Cell Biol., Pt A:99-112 (VSV-G); U.S. Pat. No. 5,449,614. In some cases, the viral polypeptide is genetically modified to promote expression or enhanced binding to a receptor.

In general, a recombinant virus is produced by introducing a viral DNA or RNA construct into a producer cell. In some cases, the producer cell does not express exogenous genes. In other cases, the producer cell is a "packaging cell" comprising one or more exogenous genes, e.g., genes encoding one or more gag, pol, or env polypeptides and/or one or more retroviral gag, pol, or env polypeptides. The retroviral packaging cell may comprise a gene encoding a viral polypeptide, e.g., VSV-g that aids entry into target cells. In some cases, the packaging cell comprises genes encoding one or more lentiviral proteins, e.g., gag, pol, env, vpr, vpu, vpx, vif, tat, rev, or nef. In some cases, the packaging cell comprises genes encoding adenovirus proteins such as E1A or E1B or other adenoviral proteins. For example, proteins supplied by packaging cells may be retrovirus-derived proteins such as gag, pol, and env; lentivirus-derived proteins such as gag, pol, env, vpr, vpu, vpx, vif, tat, rev, and nef; and adenovirus-derived proteins such as E1A and E1B. In many examples, the packaging cells supply proteins derived from a virus that differs from the virus from which the viral vector derives.

Packaging cell lines include but are not limited to any easily-transfectable cell line. Packaging cell lines can be based on 293T cells, NIH3T3, COS or HeLa cell lines. Packaging cells are often used to package virus vector plasmids deficient in at least one gene encoding a protein required for virus packaging. Any cells that can supply a protein or polypeptide lacking from the proteins encoded by such virus vector plasmid may be used as packaging cells. Examples of packaging cell lines include but are not limited to: Platinum-E (Plat-E); Platinum-A (Plat-A); BOSC 23 (ATCC CRL 11554); and Bing (ATCC CRL 11270), see, e.g., Morita et al., (2000), Gene Therapy, 7:1063-1066; Onishi et al., (1996), Experimental Hematology, 24:324-329; U.S. Pat. No. 6,995, 009. Commercial packaging lines are also useful, e.g., Ampho-Pak 293 cell line, Eco-Pak 2-293 cell line, RetroPack PT67 cell line, and Retro-X Universal Packaging System (all available from Clontech).

The retroviral construct may be derived from a range of retroviruses, e.g., MMLV, HIV-1, SIV, FIV, or other retrovirus described herein. The retroviral construct may encode all viral polypeptides necessary for more than one cycle of replication of a specific virus. In some cases, the efficiency of viral entry is improved by the addition of other factors or other viral polypeptides. In other cases, the viral polypeptides encoded by the retroviral construct do not support more than one cycle of replication, e.g., U.S. Pat. No. 6,872,528. In such circumstances, the addition of other factors or other viral polypeptides can help facilitate viral entry. In an exemplary embodiment, the recombinant retrovirus is HIV-1 virus comprising a VSV-g polypeptide but not comprising a HIV-1 env polypeptide.

The retroviral construct may comprise: a promoter, a multi-cloning site, and/or a resistance gene. Examples of promoters include but are not limited to CMV, SV40, EF1α, β-actin; retroviral LTR promoters, and inducible promoters. The retroviral construct may also comprise a packaging signal (e.g., a packaging signal derived from the MFG vector; a psi packaging signal). Examples of some retroviral constructs known in the art include but are not limited to: pMX, pBabeX or derivatives thereof. See e.g., Onishi et al., (1996), Experimental Hematology, 24:324-329. In some cases, the retroviral construct is a self-inactivating lentiviral vector (SIN) vector, see, e.g., Miyoshi et al., (1998), J. Virol., 72(10):8150-8157. In some cases, the retroviral construct is LL-CG, LS-CG, CL-CG, CS-CG, CLG or MFG. Miyoshi et al., (1998), J. Virol., 72(10):8150-8157; Onishi et al., (1996), Experimental Hematology, 24:324-329; Riviere et al., (1995), PNAS, 92:6733-6737. Virus vector plasmids (or constructs), include: pMXs, pMxs-IB, pMXs-puro, pMXs-neo (pMXs-IB is a vector carrying the blasticidin-resistant gene in stead of the puromycin-resistant gene of pMXs-puro) Kimatura et al., (2003), Experimental Hematology, 31: 1007-1014; MFG Riviere et al., (1995), Proc. Natl. Acad. Sci. U.S.A., 92:6733-6737; pBabePuro; Morgenstern et al., (1990), Nucleic Acids Research, 18:3587-3596; LL-CG, CL-CG, CS-CG, CLG Miyoshi et al., (1998), Journal of Virology, 72:8150-8157 and the like as the retrovirus system, and pAdex1 Kanegae et al., (1995), Nucleic Acids Research, 23:3816-3821 and the like as the adenovirus system. In exemplary embodiments, the retroviral construct comprises blasticidin (e.g., pMXs-IB), puromycin (e.g., pMXs-puro, pBabePuro); or neomycin (e.g., pMXs-neo). See, e.g., Morgenstern et al., (1990), Nucleic Acids Research, 18:3587-3596.

Methods of producing recombinant viruses from packaging cells and their uses are well established; see, e.g., U.S. Pat. Nos. 5,834,256; 6,910,434; 5,591,624; 5,817,491; 7,070,994; and 6,995,009. Many methods begin with the introduction of a viral construct into a packaging cell line. The viral construct may be introduced into a host fibroblast by any method known in the art, including but not limited to: a calcium phosphate method, a lipofection method (Feigner et al. (1987) Proc. Natl. Acad. Sci. U.S.A. 84:7413-7417), an electroporation method, microinjection, Fugene transfection, and the like, and any method described herein.

A nucleic acid construct can be introduced into a host cell using a variety of well known techniques, such as non-viral based transfection of the cell. In an exemplary aspect the construct is incorporated into a vector and introduced into a host cell. Introduction into the cell may be performed by any non-viral based transfection known in the art, such as, but not limited to, electroporation, calcium phosphate mediated transfer, nucleofection, sonoporation, heat shock, magnetofection, liposome mediated transfer, microinjection, microprojectile mediated transfer (nanoparticles), cationic polymer mediated transfer (DEAE-dextran, polyethylenimine, polyethylene glycol (PEG) and the like) or cell fusion. Other methods of transfection include transfection reagents such as Lipofectamine™, Dojindo Hilymax™, Fugene™, jetPEI™, Effectene™, and DreamFect™

Formulations, Dosages, and Routes of Administration

As discussed above, a subject treatment method generally involves administering to an individual in need thereof an effective amount of an exogenous EphB2 nucleic acid. Formulations, dosages, and routes of administration are discussed below. For the purposes of the discussion of formulations, dosages, and routes of administration, the term "active agent" refers to an exogenous EphB2 nucleic acid. In some instances, a composition comprising an active agent can comprise a pharmaceutically acceptable excipient, a variety of which are known in the art and need not be discussed in detail herein. Pharmaceutically acceptable excipients have been amply described in a variety of publications, including, for example, A. Gennaro (1995) "Remington: The Science and Practice of Pharmacy", 19th edition, Lippincott, Williams, & Wilkins.

As noted above, an active agent is an exogenous EphB2 nucleic acid. Exemplary formulations and methods for the delivery of nucleic acids are known in the art. For example, nucleic acids can be administered to cells by a variety of methods known to those of skill in the art, including, but not restricted to, encapsulation in liposomes, by iontophoresis, or by incorporation into other vehicles, such as biodegradable polymers, hydrogels, cyclodextrins (see for example Gonzalez et al., 1999, Bioconjugate Chem., 10, 1068-1074; Wang et al., International PCT publication Nos. WO 03/47518 and WO 03/46185), poly(lactic-co-glycolic)acid (PLGA) and PLCA microspheres (see for example U.S. Pat. No. 6,447,796 and US Patent Application Publication No. U.S. 2002130430), biodegradable nanocapsules, and bioadhesive microspheres, or by proteinaceous vectors (O'Hare and Normand, International PCT Publication No. WO 00/53722). In another embodiment, a nucleic acid is formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalacto-samine (PEI-PEG-triGAL) derivatives. In one embodiment, a nucleic acid is formulated as described in U.S. Patent Application Publication No. 20030077829, incorporated by reference herein in its entirety.

In one embodiment, an exogenous EphB2 nucleic acid is complexed with membrane disruptive agents such as those described in U.S. Patent Publication No. 2001/0007666, incorporated by reference herein in its entirety. In another embodiment, the membrane disruptive agent or agents and the nucleic acid active agent are also complexed with a cationic lipid or helper lipid molecule, such as those lipids described in U.S. Pat. No. 6,235,310, incorporated by reference herein in its entirety. In one embodiment, an exogenous EphB2 nucleic acid is complexed with delivery systems as described in US 2003/077829, WO 00/03683 and WO 02/087541, each incorporated herein by reference.

Pharmaceutical compositions can be formulated for controlled or sustained delivery in a manner that provides local concentration of an active agent (e.g., bolus, depot effect) and/or increased stability or half-life in a particular local environment. The compositions can include the formulation exogenous EphB2 nucleic acids with particulate preparations of polymeric compounds such as polylactic acid, polyglycolic acid, etc., as well as agents such as a biodegradable matrix, injectable microspheres, microcapsular particles, microcapsules, bioerodible particles beads, liposomes, and implantable delivery devices that provide for the controlled or sustained release of the active agent which then can be delivered as a depot injection. Techniques for formulating such sustained- or controlled-delivery means are known and a variety of polymers have been developed and used for the controlled release and delivery of drugs. Such polymers are typically biodegradable and biocompatible. Polymer hydrogels, including those formed by complexation of enantiomeric polymer or polypeptide segments, and hydrogels with temperature or pH sensitive properties, may be desirable for providing drug depot effect because of the mild and aqueous conditions involved in trapping an active agent.

Nucleic acids can be formulated in a variety of ways in order to facilitate delivery. The form (e.g., liquid, solid, pill, capsule) and composition of the formulation will vary according to the method of administration used. For example, where the formulation is administered orally, the nucleic acid can be formulated as a tablet, pill, capsule, solution (e.g., gel, syrup, slurry, or suspension), or other suitable form.

The formulation can contain components in addition to nucleic acid, where the additional components aid in the delivery of the nucleic acid. The nucleic acid can be present in a pharmaceutical composition with additional components such as, but not limited to, stabilizing compounds and/or biocompatible pharmaceutical-carriers, e.g., saline, buffered saline, dextrose, or water. The nucleic acid can also be administered alone or in combination with other agents, including other therapeutic agents. The formulation can also contain organic and inorganic compounds to, for example, facilitate nucleic acid delivery to and uptake by the target cell (e.g., detergents, salts, chelating agents, etc.).

Where the nucleic acid formulation is administered orally, the formulation can contain buffering agents or comprise a coating to protect the nucleic acid from stomach acidity and/or facilitate swallowing. In addition or alternatively, the oral formulation can be administered during an interdigestive period (between meals or at bedtime) when stomach pH is less acidic or with the administration of inhibitors of acid secretion such as H2 blockers (e.g., cimetidine) or proton pump inhibitors (e.g., PROLISEC™) The formulation can also comprise a time-release capsule designed to release the nucleic acid upon reaching the surface of intestinal cells.

A nucleic acid can be formulated in a complex with a liposome. Such complexes comprise a mixture of lipids which bind to nucleic acid, providing a hydrophobic core and hydrophilic coat which allows the genetic material to be delivered into cells. Suitable liposomes include DOPE (dioleyl phosphatidyl ethanol amine), CUDMEDA (N-(5-cholestrum-3-β-ol 3-urethanyl)-N',N'-dimethylethylene diamine).

Other formulations can also be used for nucleic acids. Such formulations include nucleic acidcoupled to a carrier molecule (e.g., an antibody or a, receptor ligand) which facilitates delivery to a target cell. A nucleic acid can be chemically modified. By the term "chemical modification" is meant modifications of nucleic acids to allow, for example, coupling of the nucleic acid compounds to a carrier molecule such as a protein or lipid, or derivative thereof. Exemplary protein carrier molecules include antibodies specific to target cells.

A nucleic acid can be formulated with any of a variety of natural polymers, synthetic polymers, synthetic co-polymers, and the like. Generally, the polymers are biodegradable, or can be readily eliminated from the subject. Naturally occurring polymers include polypeptides and polysaccharides. Suitable synthetic polymers include, but are not limited to, polylysines, and polyethyleneimines (PEI; Boussif et al., *PNAS* 92:7297-7301, 1995) which molecules can also serve as condensing agents. These carriers may be dissolved, dispersed or suspended in a dispersion liquid such as water, ethanol, saline solutions and mixtures thereof. A wide variety of synthetic polymers are known in the art and can be used.

A nucleic acid can be formulated in a lipid-based vehicle. Lipid-based vehicles include cationic liposomes such as disclosed by Feigner et al (U.S. Pat. Nos. 5,264,618 and 5,459,127; *PNAS* 84:7413-7417, 1987; *Annals N.Y. Acad. Sci.* 772: 126-139, 1995); they may also consist of neutral or negatively charged phospholipids or mixtures thereof including artificial viral envelopes as disclosed by Schreier et al. (U.S. Pat. Nos. 5,252,348 and 5,766,625). Nucleic acid/liposome complexes are suitable, and can comprise a mixture of lipids which bind to nucleic acid by means of cationic charge (electrostatic interaction). Cationic liposomes that are suitable for use include 3β-[N-(N', N'-dimethyl-aminoethane)-carbamoyl]-cholesterol (DC-Choi), 1,2-bis(oleoyloxy-3-trimethylammonio-propane (DOTAP) (see, for example, WO 98/07408), lysinylphosphatidylethanolamine (L-PE), lipopolyamines such as lipospermine, N-(2-hydroxyethyl)-N,N-dimethyl-2,3-bis(dodecyloxy)-1-propanaminium bromide, dimethyl dioctadecyl ammonium bromide (DDAB), dioleoylphosphatidyl ethanolamine (DOPE), dioleoylphosphatidyl choline (DOPC), N(1,2,3-dioleyloxy) propyl-N,N,N-triethylammonium (DOTMA), DOSPA, DMRIE, GL-67, GL-89, Lipofectin, and Lipofectamine (Thiery et al. (1997) *Gene Ther.* 4:226-237; Feigner et al., *Annals N.Y. Acad. Sci.* 772: 126-139, 1995; Eastman et al., *Hum. Gene Ther.* 8:765-773, 1997). Polynucleotide/lipid formulations described in U.S. Pat. No. 5,858,784 can also be used in the methods described herein. Many of these lipids are commercially available from, for example, Boehringer-Mannheim, and Avanti Polar Lipids (Birmingham, Ala.). Also suitable are the cationic phospholipids found in U.S. Pat. Nos. 5,264,618, 5,223,263 and 5,459,127. Other suitable phospholipids which may be used include phosphatidylcholine, phosphatidylserine, phosphatidylethanolamine, sphingomyelin, phosphatidylinositol, and the like. Cholesterol may also be included.

Dosage levels can be readily determined by the ordinarily skilled clinician, and can be modified as required, e.g., as required to achieve the desired effect. Dosage levels can be on the order of from about 0.1 mg to about 100 mg per kilogram of body weight per day. The amount of active agent that can be combined with the carrier materials to produce a single dosage form varies depending upon, e.g., the host treated and the particular mode of administration. Dosage unit forms can contain between from about 1 mg to about 500 mg of an active agent.

An active agent can be delivered via any of a variety of modes and routes of administration, including, e.g., local delivery by injection; local delivery by continuous release; systemic delivery by oral administration; systemic delivery by intravenous administration; and the like. An active agent can be delivered by various routes, including intracranial, intrathecal, intraventricular, intracapsular and other routes of administration.

In another embodiment, a controlled release system can be placed in proximity of the target tissue. For example, a micropump may deliver controlled doses directly into the brain, thereby requiring only a fraction of the systemic dose (See, e.g., Goodson, 1984, in *Medical Applications of Controlled Release*, vol. 2, pp. 115-138).

In one embodiment, it may be desirable to administer the agent locally to the area in need of treatment; this may be achieved, for example, and not by way of limitation, by local infusion during surgery, topical application, injection, by means of a catheter, by means of a suppository, or by means of an implant. An implant can be of a porous, non-porous, or gelatinous material, including membranes, such as sialastic membranes, or fibers.

In some embodiments, an exogenous EphB2 nucleic acid is formulated and/or delivered in such a way as to facilitate or bypass crossing the blood-brain barrier (BBB). Molecules that cross the blood-brain barrier use two main mechanisms: free diffusion; and facilitated transport. Delivery of therapeutic agents to the CNS can be achieved by several methods.

Administration can be systemic or local. In some embodiments, an exogenous EphB2 nucleic acid is introduced into the central nervous system by any suitable route, including intraventricular and intrathecal injection; intraventricular injection may be facilitated by an intraventricular catheter, for example, attached to a reservoir, such as an Ommaya reservoir.

Combination Therapies

In some embodiments, a subject method further includes administering at least one additional therapeutic agent. Suitable additional therapeutic agents include, but are not limited to, acetylcholinesterase inhibitors, including, but not limited to, Aricept (donepezil), Exelon (rivastigmine), metrifonate, and tacrine (Cognex); non-steroidal anti-inflammatory agents, including, but not limited to, ibuprofen and indomethacin; cyclooxygenase-2 (Cox2) inhibitors such as Celebrex; and monoamine oxidase inhibitors, such as Selegilene (Eldepryl or Deprenyl). Dosages for each of the above agents are known in the art. For example, Aricept is generally administered at 50 mg orally per day for 6 weeks, and, if well tolerated by the individual, at 10 mg per day thereafter.

Subjects Suitable for Treatment

Subjects suitable for treatment with a method of treating an amyloid beta-induced neurodegenerative disorder include individuals who have been diagnosed as having a disorder such as Alzheimer's disease, age-related dementia, cerebral or systemic amyloidosis, hereditary cerebral hemorrhage with amyloidosis, or Down's syndrome.

Screening Methods

The present disclosure provides methods of identifying a candidate agent for the treatment of an amyloid-beta-induced neurodegenerative disease. In some embodiments, the methods generally involve: a) contacting an EphB2 receptor and an amyloid-beta polypeptide with a test agent; and b) determining the effect, if any, of the test agent on binding of the amyloid-beta polypeptide to the EphB2 receptor. A test agent that reduces binding of the amyloid-beta polypeptide to the EphB2 receptor is a candidate agent for treating an amyloid-beta-induced neurodegenerative disease. In other embodiments, the methods generally involve: a) contacting a cell that expresses an EphB2 receptor with a test agent; and b) determining the effect, if any, of the test agent on the level of the EphB2 receptor in the cell. A test agent that increases the level of the EphB2 receptor in the cell is a candidate agent for treating an amyloid-beta-induced neurodegenerative disease. In some embodiments, the cell is a neuron.

Assays of the invention include controls, where suitable controls include a sample in the absence of the test agent. Generally a plurality of assay mixtures is run in parallel with different test agent concentrations to obtain a differential response to the various concentrations. Typically, one of these concentrations serves as a negative control, i.e. at zero concentration or below the level of detection.

A variety of other reagents may be included in the screening assay. These include reagents such as salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The components of the assay mixture are added in any order that provides for the requisite binding or other activity. Incubations are performed at any suitable temperature, typically between 4° C. and 40° C. Incubation periods are selected for optimum activity, but may also be optimized to facilitate rapid high-throughput screening. Typically between 0.1 and 1 hour will be sufficient.

As used herein, the term "determining" refers to both quantitative and qualitative determinations and as such, the term "determining" is used interchangeably herein with "assaying," "measuring," and the like.

The terms "candidate agent," "test agent," "agent," "substance," and "compound" are used interchangeably herein. Candidate agents encompass numerous chemical classes, typically synthetic, semi-synthetic, or naturally-occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.). Alternatively, libraries of natural compounds in the form of bacterial, fungal, plant and animal extracts are available from Pan Labs (Bothell, Wash.) or are readily producible.

Candidate agents may be small organic or inorganic compounds having a molecular weight of more than 50 and less than about 2,500 daltons. Candidate agents may comprise functional groups necessary for structural interaction with other macromolecules such as proteins, e.g., hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

A test agent can be a small molecule. The test molecules may be individual small molecules of choice or in some cases, the small molecule test agents to be screened come from a combinatorial library, i.e., a collection of diverse chemical compounds generated by either chemical synthesis or biological synthesis by combining a number of chemical "building blocks." For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. Indeed, theoretically, the systematic, combinatorial mixing of 100 interchangeable chemical building blocks results in the synthesis of 100 million tetrameric compounds or 10 billion pentameric compounds. See, e.g., Gallop et al., (1994), J. Med. Chem., 37(9), 1233-1251. Preparation and screening of combinatorial chemical libraries are well known in the art. Combinatorial chemical libraries include, but are not limited to: diversomers such as hydantoins, benzodiazepines, and dipeptides, as described in, e.g., Hobbs et al., (1993), Proc. Natl. Acad. Sci. U.S.A., 90:6909-6913; analogous organic syntheses of small compound libraries, as described in Chen et al., (1994), J. Amer. Chem. Soc., 116:2661-2662; Oligocarbamates, as described in Cho, et al., (1993), Science, 261:1303-1305; peptidyl phosphonates, as described in Campbell et al., (1994), J. Org. Chem., 59: 658-660; and small organic molecule libraries containing, e.g., thiazolidinones and metathiazanones (U.S. Pat. No. 5,549,974), pyrrolidines (U.S. Pat. Nos. 5,525,735 and 5,519,134), benzodiazepines (U.S. Pat. No. 5,288,514).

Numerous combinatorial libraries are commercially available from, e.g., ComGenex (Princeton, N.J.); Asinex (Moscow, Russia); Tripos, Inc. (St. Louis, Mo.); ChemStar, Ltd. (Moscow, Russia); 3D Pharmaceuticals (Exton, Pa.); and Martek Biosciences (Columbia, Md.).

Cell-Free In Vitro Assays

As noted above, in some embodiments, a subject generally involves: a) contacting an EphB2 receptor and an amyloid-beta polypeptide with a test agent; and b) determining the effect, if any, of the test agent on binding of the amyloid-beta polypeptide to the EphB2 receptor. In these embodiments, the assay is a cell-free in vitro assay.

A test agent that reduces binding of the amyloid-beta polypeptide to the EphB2 receptor by at least about 5%, at least about 10%, at least about 15%, at least about 20%, at least about 25%, at least about 30%, at least about 35%, at least about 40%, at least about 50%, or more than 50%, compared to the level of binding of the amyloid-beta polypeptide to the EphB2 receptor in the absence of the test agent, is a candidate agent for treating an amyloid-beta-induced neurodegenerative disease. In some embodiments, the Aβ polypeptide and the EphB2 polypeptide are substantially pure.

In some embodiments, the Aβ polypeptide is an $A\beta_{1-42}$ polypeptide. In some embodiments, an $A\beta_{1-42}$ polypeptide has the amino acid sequence: DAEFRHDSGYEVH-HQKLVFFAEDVGSNKGAIIGLMVGGVVIA (SEQ ID NO:5).

The Aβ polypeptide can include a moiety that provides for detection, purification, or immunoprecipitation, e.g., a radiolabel, biotin, a fluorescent protein, $(His)_n$, (e.g., 6His), glutathione-S-transferase (GST), hemagglutinin (HA; e.g., CYPYDVPDYA; SEQ ID NO: 6), FLAG (e.g., DYKD-DDDK; SEQ ID NO:7), c-myc (e.g., CEQKLISEEDL); SEQ ID NO:8), immunoglobulin Fc, and the like.

Suitable EphB2 polypeptides are described above. The EphB2 polypeptide can also comprise a moiety that provides for detection, purification, or immunoprecipitation, e.g., a radiolabel, biotin, a fluorescent protein, $(His)_n$, (e.g., 6His), glutathione-S-transferase (GST), hemagglutinin (HA; e.g., CYPYDVPDYA), SEQ ID NO:6 ), FLAG (e.g., DYKD-DDDK; SEQ ID NO:7), c-myc (e.g., CEQKLISEEDL; SEQ ID NO: 8), immunoglobulin Fc, and the like.

The effect of a test agent on binding of Aβ to EphB2 can be determined using any known assay for determining binding of one polypeptide to another. Examples include, e.g., an enzyme-linked immunosorbent assay, an immunoprecipitation assay, and the like.

A test agent of interest is assessed for any cytotoxic activity (other than anti-proliferative activity) it may exhibit toward a living eukaryotic cell, using well-known assays, such as trypan blue dye exclusion, an MTT (3-(4,5-dimethylthiazol-2-yl)-2,5-diphenyl-2 H-tetrazolium bromide) assay, and the like. Agents that do not exhibit cytotoxic activity may be candidate agents for use in a treatment method.

Cell-Based Assays

As noted above, in some embodiments, a subject method generally involves: a) contacting a cell that expresses an EphB2 receptor with a test agent; and b) determining the effect, if any, of the test agent on the level and/or function of the EphB2 receptor in the cell. Such an assay is a cell-based in vitro assay. A test agent that increases the level of the EphB2 receptor in the cell is a candidate agent for treating an amyloid-beta-induced neurodegenerative disease.

The effect of the test agent on the level of EphB2 in the cell can be determined using an immunological assay, e.g., using antibody to EphB2. The effect of the test agent on a function of EphB2 in the cell can be determined by testing the activity of an NMDA receptor in the cell, e.g., using standard electrophysiological methods.

In some embodiments, the cells ("host cells") used in the assays are mammalian cells. Suitable host cells include eukaryotic host cells that can be cultured in vitro, either in suspension or as adherent cells. In some embodiments, the cell is a neuron.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

Suitable cell lines include, but are not limited to, a human glioma cell line, e.g., SVGp12 (ATCC CRL-8621), CCF-STTG1 (ATCC CRL-1718), SW 1088 (ATCC HTB-12), SW 1783 (ATCC HTB-13), LLN-18 (ATCC CRL-2610), LNZTA3WT4 (ATCC CRL-11543), LNZTA3WT11 (ATCC CRL-11544), U-138 MG (ATCC HTB-16), U-87 MG (ATCC HTB-14), H4 (ATCC HTB-148), and LN-229 (ATCC CRL-2611); a human medulloblastoma-derived cell line, e.g., D342 Med (ATCC HTB-187), Daoy (ATCC HTB-186), D283 Med (ATCC HTB-185); a human tumor-derived neuronal-like cell, e.g., PFSK-1 (ATCC CRL-2060), SK-N-DZ (ATCCCRL-2149), SK-N-AS (ATCC CRL-2137), SK-N-FI (ATCC CRL-2142), IMR-32 (ATCC CCL-127), etc.; a mouse neuronal cell line, e.g., BC3H1 (ATCC CRL-1443), EOC1 (ATCC CRL-2467), C8-D30 (ATCC CRL-2534), C8-S (ATCC CRL-2535), Neuro-2a (ATCC CCL-131), NB41A3 (ATCC CCL-147), SW10 (ATCC CRL-2766), NG108-15 (ATCC HB-12317); a rat neuronal cell line, e.g., PC-12 (ATCC CRL-1721), CTX TNA2 (ATCC CRL-2006), C6 (ATCC CCL-107), F98 (ATCC CRL-2397), RG2 (ATCC CRL-2433), B35 (ATCC CRL-2754), R3 (ATCC CRL-2764), SCP (ATCC CRL-1700), OA1 (ATCC CRL-6538).

The cell used in the assay can produce Aβ and EphB2 endogenously. The cell used in the assay can be genetically modified with a recombinant expression vector(s) comprising a nucleotide sequence encoding Aβ and EphB2, such that the encoded Aβ and EphB2 are produced in the cell. In general, the genetically modified cells can be produced using standard methods. Expression constructs comprising nucleotide sequences encoding an EphB2 polypeptide are introduced into the host cell using standard methods practiced by one with skill in the art. In some embodiments, the Aβ and/or the EphB2 polypeptide is encoded on a transient expression vector (e.g., the vector is maintained in an episomal manner by the cell). Alternatively, or in addition, an Aβ and/or an EphB2 polypeptide-encoding expression construct can be stably integrated into the cell line.

Behavioral Studies

A candidate agent can be further evaluated for its effect on behavioral parameters, e.g., learning and memory. Behavioral tests designed to assess learning and memory deficits can be employed. An example of such as test is the Morris Water maze (Morris *Learn Motivat* 12:239-260 (1981)). In this procedure, the animal is placed in a circular pool filled with water, with an escape platform submerged just below the surface of the water. A visible marker is placed on the platform so that the animal can find it by navigating toward a proximal visual cue. Alternatively, a more complex form of the test in which there are no formal cues to mark the platform's location is given to the animals. In this form, the animal must learn the platform's location relative to distal visual cues. Alternatively, or in addition, memory and learning deficits can be studied using a 3 runway panel for working memory impairment (attempts to pass through two incorrect panels of the three panel-gates at four choice points) (Ohno et al. *Pharmacol Biochem Behav* 57:257-261 (1997)).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Reversing EphB2 Depletion Rescues Cognitive Functions in an Alzheimer Model

Amyloid-β (Aβ) oligomers may cause cognitive deficits in Alzheimer's disease (AD) by impairing neuronal NMDA-type glutamate receptors (NMDARs), whose function is regulated by the receptor tyrosine kinase EphB2. Here it is shown that Aβ oligomers bind to the fibronectin repeats domain of EphB2 and trigger EphB2 degradation in the proteasome. To determine the pathogenic importance of EphB2 depletions in AD and related models, lentiviral constructs were used to reduce or increase neuronal expression of EphB2 in memory centers of the mouse brain. In nontransgenic mice, shRNA-mediated knockdown of EphB2 reduced NMDAR currents and impaired long-term potentiation (LTP) in the dentate gyrus (DG), which currents are important for memory formation. Increasing EphB2 expression in the DG of human amyloid precursor protein transgenic mice reversed their deficits in NMDAR-dependent LTP and their memory impairments. Thus, depletion of EphB2 is critical in A(3-induced neuronal dysfunction.

Materials and Methods

General. Unless indicated otherwise, all data reported discussed below were obtained in blind-coded experiments, in which the investigators who obtained the data were unaware of the specific genotype and treatment of mice, brain slices and cell cultures. The number of mice, slices, and cell cultures analyzed in each experiment are shown in the Table, below.

TABLE

| Biochemistry | | | |
|---|---|---|---|
| Figure Panels | 1: b-f, h<br>2: c-f | 1: g<br>2: a | 3: b |
| Wells per condition | 3 | 6 | |
| Independent experiments | 3 | 6 | |
| Human brain samples per condition | | | 4-6 |
| Mouse brain samples per condition | | | 4-10 |
| Electrophysiology | | | |
| Figure Panels | 3: c, d, g | 4: c, f | |
| Mice per experiment | 14 | 21 | |
| Mice per genotype and treatment | | 3-8 | |
| Mice per genotype | 3 | | |
| Mice per treatment | 4 | | |
| Slices per treatment and/or genotype | 8-9 | 6-20 | |
| Behavior | | | |
| Figure panels | 5: a-f | | |
| Total number of mice | 102 | | |
| Cohorts of mice | 1; 2 | | |
| Mice per cohort | 42; 60 | | |
| Mice per genotype and treatment | 9-12; 15 | | |

Experimental models. Heterozygous transgenic and non-transgenic (NTG) mice were from hAPP line J20[7,8,37,38]. Primary neuronal cultures from wild-type rats were treated with medium conditioned by CHO cells that do or do not produce human Aβ oligomers[39,40].

Experimental manipulations. Lentiviral constructs directing neuronal expression of no transgene products, EphB2-Flag, or green fluorescent protein (GFP) in combination with anti-EphB2 short hairpin RNAs (shRNAs) or scrambled control shRNA were injected stereotactically into dentate gyrus (DG) of mice[20,41]. Neuronal cultures were infected with some of these constructs and stimulated with Fc-ephrin-B2 or Fc control[12,42].

Outcome measures. The interaction between biotinylated or naturally secreted Aβ oligomers and EphB2 was assessed under cell-free conditions and in neuronal cultures of primary neurons or HEK cells by pull-down with Avidin-agarose beads[43] or immunoprecipitation and Western blot (WB)[44]. EphB2 and NR1 levels in brain tissues or neuronal cultures were determined by immunoprecipitation and WB or WB alone[44]. Corresponding transcripts were measured by quantitative reverse transcription-polymerase chain reaction (qRT-PCR). Expression of Fos in neuronal cultures was determined by WB[44]. Field recordings[8] or whole-cell patch-clamp recordings[45] from acute hippocampal slices were used to determine synaptic strength (fEPSP input-output relationships; mediated by either α-amino-3-hydroxy-5-methyl-4-isoxazolepropionic acid (AMPA) receptors (AMPARs) or NMDARs), synaptic plasticity (LTP), and NMDAR/AMPAR ratios of excitatory postsynaptic currents (EPSCs) at the medial perforant path to DG granule cell (GC) synapse. Learning and memory were assessed in the Morris water maze, novel object recognition test, novel place recognition test, and passive avoidance test[46-49]. Aβ levels in the DG of hAPP-J20 mice were determined by enzyme linked immunosorbent assay (ELISA)[50]. Fos and calbindin (CB) expression in hippocampal sections was determined by immunohistochemistry.

hAPP transgenic mice. Heterozygous transgenic and non-transgenic (NTG) mice were from line J20, which expresses an alternatively spliced hAPP minigene encoding hAPP695, hAPP751 and hAPP770 with the Swedish and Indiana familial AD mutations directed by the platelet derived growth factor (PDGF) β-chain promoter[57,59-63].

Preparation of Aβ oligomers. Naturally secreted Aβ oligomers. Stably hAPP-transfected CHO-7PA2 cells, which produce Aβ oligomers, were cultured as described[64,65]. Briefly, untransfected CHO cells and CHO-7PA2 cells were grown to 80% confluency in 150-mm dishes, washed with PBS, and incubated for ~24 h in serum-free Neurobasal A medium. The medium was collected and spun at 1000 rpm for 10 min to eliminate cell debris. Supernatants were concentrated 10-fold with a Centriprep YM-3 (Millipore), collected as 1-ml aliquots in 1.5-ml Eppendorf tubes and stored at −80° C. After size-exclusion chromatography to remove secreted APP, 1-ml aliquots of conditioned medium were lyophilized and reconstituted in artificial cerebrospinal fluid.

Synthetic Aβ oligomers: Synthetic biotinylated Aβ1-42 peptides (rPeptide) were lyophilized in hydroxyfluoroisopropanol (HFIP), reconstituted in dimethyl sulfoxide at 2.2 mM, diluted in Neurobasal A medium, pH 7.4 (Invitrogen) to 1 μg/ml, incubated at 4° C. for 48 h, and stored at −80° C. until use[58]. For treatment of cells, stock solutions of Aβ peptides were diluted in fresh Neurobasal A/N2 medium to final concentrations of 1 μg/ml (equivalent in total Aβ content to a 0.22 μM solution of monomeric Aβ).

Primary neuronal culture and pharmacology. Cortex and hippocampus of wild-type rat pups (P0) were digested with papain. Cells were plated in polylysine-coated wells and maintained in serum-free Neurobasal medium supplemented with B27 (Invitrogen) and antibiotics. Half the medium was changed after 5 days in culture. Cells were used after 5-11 days in culture. More than 95% of the cells were neurons, as determined by staining with an antibody against the neuron-specific marker MAP2. Neuronal cultures were treated with Aβ oligomer fractions from 7PA2-conditioned medium, control fractions from untransfected CHO cells, synthetic Aβ or vehicle, clustered recombinant Fc-ephrin-B2-(R&D Systems), or control Fc (Jackson ImmunoResearch Labs) as described in the text. For detection of Fos, cells were pretreated with tetrodotoxin (TTX, 1 μM, 48 h) and 2,3-dihydroxy-6-nitro-7-sulfamoyl-benzo[f]quinoxaline-2,3-dione (NBQX, 40 μM 48 h) to reduce endogenous synaptic activity[66]. Fc-ephrin-B2 and control Fc were preclustered with anti-human Fc antibody at 50 ng/ml in Neurobasal medium was kept at room temperature for 1 h and applied at final concentrations of 500 ng/ml. Treatment with anti-Fc antibodies served as an additional control. Inhibitors were used at the following concentration in the indicated vehicle: lactacystin (10 μM in water), bafilomycin (1.0 μM in DMSO). After treatment, cells were harvested in lysis buffer A (10 mM Tris/HCl, pH 7.5, 150 mM NaCl, 0.5% Triton X-100, 0.5% deoxycholate, 5 mM EDTA), spun at 13,000 rpm for 5 min, and frozen at −80° C. for subsequent determination of protein concentration and western blot analyses.

Biotinylation assay. Rat primary neurons were surface biotinylated as described[67]. Briefly, primary neurons were cultured for 7 divisions (DIV), placed on ice, and rinsed three times in ice-cold phosphate-buffered saline (PBS). Neurons were then incubated in ice-cold PBS containing 2 mg/ml sulfo-NHS-LC-biotin (Pierce) for 30 min at 4° C., rinsed twice in PBS, and lysed in 250 μl of PBS (for each well of a 6-well plate) containing complete protease inhibitor cocktail (Roche), 0.1% sodium dodecyl sulfate (SDS), and 1% Triton X-100. Samples were then briefly sonicated. Ten percent of the cell lysate was saved to determine total protein concentration by Bradford assay. To isolate biotinylated proteins, the other 90% of the cell lysate (approx. 250 μg of protein per sample) was incubated overnight with 50 μl of Avidin-agarose beads (Pierce) in PBS containing 1% NP-40 (non-ionic detergent) to avoid nonspecific binding. Isolated proteins were rinsed three times in PBS and boiled in 50 μl of sample buffer. Western blots were then carried out, and data were quantified by comparing the ratio of biotinylated to total protein for a given culture and normalizing to control untreated cultures.

Pull-down assay. Cell-free condition. Different amounts of synthetic biotinylated A(31-42 oligomers (rPeptide) and recombinant mouse Fc-EphB2 chimera (R&D Systems) were mixed in 400 μl of binding buffer (50 mM Tris, pH 7.5, 200 mM NaCl, 0.1% NP-40) and rotated overnight at 4° C. Avidin-agarose beads (40 μA of 75% slurry; Pierce) were added, and the tubes were rotated at 4° C. for 2 h and spun at 13,000 rpm for 30 s. The supernatant was discarded. Beads were washed twice with 500 μL of PBS and resuspended in 30 μl of 2× loading buffer. Samples were boiled at 90° C. and loaded onto a NuPAGE 4-12% Bis-Tris gel for western blot analysis.

Cell culture condition. HEK cell line: Cells grown on 12-well plates were transiently transfected with full-length EphB2 or EphB2 lacking either its LB domain or its fibronectin (FN) repeats domain. Empty pcDNA3 served as a negative control. Seventy-two hours after transfection, cells were treated or not with different amounts of synthetic Aβ for 2 h. After incubation, cells were washed with PBS to remove unbound Aβ and then lysed with buffer A supplemented with a protease inhibitor mixture (Sigma). Bound Aβ was analyzed by immunoprecipitation (IP) using an antibody against glutathione-S-transferase (GST), followed by sodium dodecyl sulfate-polyacrylamide gel electrophoresis (SDS-PAGE) and immunoblotting with an antibody directed against Aβ. Primary neurons: Rat primary neurons grown on 12-well plates for 7 DIV were treated with different amounts of synthetic Aβ oligomers for 2 h. Cells were washed with PBS to remove unbound Aβ and lysed with buffer A supplemented with a protease inhibitor mixture (Sigma). Samples were then analyzed by immunoprecipitation and SDS-PAGE followed by immunoblotting.

Immunohistochemistry. Immunofluorescence staining. Rat primary neurons were grown on coverslips for 7 DIV. Cells were rinsed with ice-cold PBS, fixed with 4% paraformaldehyde in PBS for 30 min, then rinsed in 0.1% PBS-Triton X-100 for 10 min. Coverslips were incubated in blocking solution (10% normal donkey serum in 0.01% PBS-Triton X-100) for 30 min at room temperature and overnight at 4° C. with anti-rabbit EphB2 antibody (H-80, 1:200, Santa Cruz Biotechnology) diluted in blocking solution. After rinses with 0.01% PBS-Triton X-100, cells were incubated with appropriate Alexa-conjugated secondary antibodies (1:300, Invitrogen) diluted in 10% normal donkey serum in PBS for 1 h at room temperature. Coverslips were rinsed extensively with PBS and mounted with Vectashield mounting medium (Vector Laboratories). For analysis, digitized images were obtained with a DEI-470 digital camera (Optronics) on a BX-60 microscope (Olympus). DAB staining. Tissue preparation and immunohistochemistry were performed as described[62]. Primary antibodies used included the following: rabbit anti-calbindin (1:15,000; Swant), rabbit anti-Fos (1:10,000; Ab-5, Oncogene).

Generation of EphB2 deletion and point mutants.

Deletion mutant: Cloning of full-length EphB2 and deletion mutants lacking the ligand binding (LB) domain or the FN repeats domain was performed using polymerase chain reaction. Each construct was designed with a carboxyl terminal GST-tag by cloning synthetic genes into NdeI digested pET41a(+) derivative lacking its multiple cloning sites. The resulting GST-tagged genes were then inserted between the XbaI and xhoI sites of a pcDNA3 vector and their expression was tested in HEK cells. Point mutant: To generate EphB2 point mutant, Wild-type EphB2 cDNA (encoding for Flag-tagged mouse EphB2) was used as the template to introduce point mutations using the QuickChange site-directed mutagenesis kit (Stratagene) according to the manufacturer's protocol. The resulting EphB2 gene bears the following mutations: T6836C, C6839A and G6842A. These mutations were introduced into the EphB2 sequence targeted by sh-EphB2-308, without altering its amino acid sequence. The EphB2 mutant was used to produce active lentiviral particles by cotransfecting the transfer vector with two helper plasmids, delta8.9 (packaging vector) and VSV-G (envelope vector), into HEK293T cells.

Lentivirus production and stereotaxic injection. Lentiviral vectors were based on FUGW[68]. EphB2 expression was reduced with two different shRNAs targeting mouse EphB2 placed under the U6 promoter. The target sequences were 5'-ACGAGAACATGAACACTAT-3' (sh-EphB2-306; SEQ ID NO:9), 5'-TGAACAGTATCCAGGTGAT-3' (sh-EphB2-308; SEQ ID NO:10). The U6-shRNA expression cassette (pSilencer 2.0, Ambion) was inserted between the Pad and NheI sites of a modified FUGW lentiviral backbone, placing the shRNA cassette upstream of an ubiquitin C promoter directing expression of enhanced GFP. A similar construct expressing a scrambled shRNA was used as a control. To increase expression of EphB2, a sequence encoding EphB2-Flag was inserted between the NodI sites of the FUW backbone. Because EphB2 cDNA is ~3 kB and large inserts can lead to packaging problems and low viral titers GFP was not included in this construct; instead, the short Flag tag was used. Active lentiviral particles were generated by cotransfecting the transfer vector with two helper plasmids, delta8.9 (packaging vector) and VSV-G (envelope vector), into HEK293T cells. The viral particles were purified from the culture medium by ultracentrifugation. An empty virus was used as control. Viral titers were determined by p24 ELISA[55].

Two- to 4-month-old NTG and hAPP-J20 mice were anesthetized by intraperitoneal injection with Avertin (tribromoethanol, 250 mg/kg) or a mixture of ketamine (75 mg/kg) and medetomidine (1 mg/kg). Mice were placed in a stereotaxic frame, and lentiviral vectors were stereotactically injected bilaterally into the DG (2-3 ml/site; 1 site/hemisphere) at the following coordinates[69]: a/p, −2.1, m/l±1.8, d/v, −2.0. After surgery, anesthesia was reversed with atipamezole (1 mg/kg). Behavioral assays were carried out 4-8 weeks after lentiviral injections. Hemibrains from replicate groups of mice injected with lentiviral vectors as described above were used after a similar interval to prepare acute hippocampal slices for electrophysiological measurements; the opposite hemibrains were snap-frozen at −80° C. and homogenized in lysis buffer for biochemical analyses.

While the small size of shRNAs allowed us to incorporate GFP into shRNA-encoding lentiviral constructs, the large size of the EphB2 cDNA made this strategy impossible for EphB2-encoding lentiviral constructs. Consequently, GFP could be used to document typical transduction efficiencies and expression patterns only for the former but not the latter. Based on the results obtained with Lenti-sh-SCR/GFP, it was estimated that on average ~60% of GCs are transduced. Similar transduction efficiencies and expression patterns were observed when lentiviral constructs were used to express other factors in DG GCs[70,71], making it likely that the transduction efficiency and expression pattern of Lenti-EphB2-Flag were not much different.

Protein extraction from tissues. Total tissue lysates from mouse or human brain were obtained by homogenizing entire mouse hemibrains or microdissected hippocampus in ice-cold lysis buffer (10 mM Tris/HCl, pH 7.5, 150 mM NaCl, 0.5% Triton X-100, 0.5% deoxycholate, 5 mM EDTA) supplemented with a protease inhibitor mixture (Sigma). Samples were centrifuged at 1000×g for 10 min at 4° C. The supernatant was placed on ice and the pellets were re-homogenized in 500 μL1 of lysis buffer and centrifuged at 1000×g for 10 min at 4° C. The supernatant was combined with the first supernatant collected and centrifuged at 100,000×g for 1 h at 4° C. Supernatant from this last centrifugation was then collected and used to determine the protein concentration of the samples and for western blot analyses.

ELISA Analysis of Aβ Levels. Whole hemibrains were microdissected, and the DG was isolated. DG tissues homogenized in 5M guanidine buffer were analyzed by ELISA for levels of human Aβ1-x and Aβ1-42 as described[55].

Immunoblotting. For detection of Fos and NR1, 25 μg of protein was loaded into each well of a 4-12% gradient SDS-PAGE gel. Gels were transferred to nitrocellulose membranes and immunoblotted with rabbit anti-Fos (1:500, Santa Cruz Biotechnology) or mouse anti-NR1 (1:1000, Millipore). For detection of EphB2 in mouse samples, 250 μg of proteins were immunoprecipitated with an anti-mouse EphB2 antibody (2 μg, R&D Systems) and analyzed by WB. For detection of EphB2 in human samples, 100 μg of proteins were directly immunoblotted with a rabbit polyclonal antibody against amino acids 255-334 in the N-terminal extracellular domain of human EphB2 (H-80, 1:200, Santa Cruz Biotechnology) in blocking buffer (Tris-buffered saline/0.1% Tween/ 5% milk, pH 7.6) overnight. For detection of ubiquitinated EphB2, 100 μg of proteins were immunoprecipitated with anti-ubiquitin (P4D1, 2 μg, Santa Cruz Biotechnology) and analyzed by WB with anti-mouse EphB2 (R&D Systems). Tubulin signals were obtained by loading 15 μg of protein per well from corresponding samples and immunoblotting with an anti-tubulin antibody. Goat anti-rabbit or anti-mouse antibodies (1:5000, Chemicon; room temperature, 2 h) were used as secondary antibodies. Protein bands were visualized with an ECL system (Pierce) and quantified densitometrically with Image J software (National Institutes of Health).

qRT-PCR. For quantitative fluorogenic reverse transcription-polymerase chain reaction (RT-PCR), total RNA was isolated from frozen brain tissues with RNeasy Mini kits with an on column RNase-free DNase I treatment (Qiagen). Total RNA was reverse transcribed with random hexamers and oligo(dT) primers. Diluted reactions were analyzed with SYBR green polymerase chain reaction (PCR) reagents and an ABI Prism 7700 sequence detector (Applied Biosystems). Human EphB2 mRNA levels were normalized to 18S RNA, whose levels did not differ between AD cases and nondemented controls. Endogenous mouse EphB2 and exogenous EphB2-Flag mRNA levels were normalized to glyceraldehyde-3-phosphate dehydrogenase (GAPDH). cDNA levels of EphB2, Flag-EphB2, 18S and GAPDH were determined relative to standard curves from pooled samples. The slope of standard curves, control reactions without reverse transcriptase (RT), and dissociation curves of products indicated adequate PCR quality. The following primers were used: mouse EphB2 forward, 5'-GTGTGGAGCTATGGCATCGT-3'(SEQ ID NO:11); reverse, 5'-TGGGCG GAGGTAGTCT-GTAG-3' (SEQ ID NO:12). Human EphB2 forward, 5'-TG-CAATGTCTTTGAGTCAA GCC-3' (SEQ ID NO:13); reverse, 5'-ATGCGG TGGGCGCC-3' (SEQ ID NO:14). Human 18S forward, 5'-ATCAACTTTCGATGGTAGTCG-3' (SEQ ID NO:15); reverse, 5'-TCCTTGGATGTGG-TAGCCG-3' (SEQ ID NO:16) . Flag forward, 5'-ATTCT-GCTGGCTGCTGCT-3' (SEQ ID NO:18); reverse, 5'-CGTTGCTGTCGTAGAGTCC ' (SEQ ID NO:17).

Electrophysiology in acute slice preparations. NTG and/or hAPP (J20 line) mice (2-5 months old) were anesthetized with Avertin (tribromoethanol, 250 mg/kg) and decapitated 4-8 weeks after the injection with lentivirus. For NTG mice injected with Lenti-sh-EphB2/GFP or Lenti-sh-Scramble/ GFP, half of the brain was used to measure levels of EphB2 mRNA by qRT-PCR, and the other half from the same mice was used for electrophysiology recordings. For hAPP mice and NTG controls injected with Lenti-EphB2-Flag or lenti-Empty, half of the brain was used for biochemical measurements (WB, immunohistochemistry) and the other half from the same mice was used for electrophysiology measurements. Brains were quickly removed and placed in ice-cold solution containing (in mM) 2.5 KCl, 1.25 $NaPO_4$, 10 $MgSO_4$, 0.5 $CaCl_2$, 26 $NaHCO_3$, 11 glucose, and 234 sucrose (pH, ~7.4; 305 mOsmol). Coronal 350-μm slices were cut with a vibratome and collected in the above solution. Slices were then incubated for 30 min in standard artificial cerebrospinal fluid (30° C.) containing (in mM) 2.5 KCl, 126 NaCl, 10 glucose, 1.25 $NaH_2PO_4$, 1 $MgSO_4$, 2 $CaCl_2$, and 26 $NaHCO_3$ (290 mOsmol; gassed with 95% $O_2$-5% $CO_2$, pH~7.4). Subsequently, slices were maintained at room temperature for 30 min before recording. Individual slices were transferred to a submerged recording chamber, where they were maintained at 30° C. and perfused with artificial cerebrospinal fluid at a rate of 2 ml/min. No recordings were made on slices >5 h after dissection.

For whole-cell patch-clamp recordings, EGFP-expressing GCs were identified under epifluorescence, and voltage-clamp recordings were obtained under infrared differential interference contrast video microscopy. The intracellular patch pipette solution contained (in mM) 120 Cs-gluconate, 10 HEPES, 0.1 EGTA, 15 $CsCl_2$, 4 $MgCl_2$, 4 Mg-ATP, and 0.3 $Na_2$-GTP, pH 7.25, adjusted with 1M CsOH (285-290 mOsm; patch electrode resistance: 3-6 MΩ). EPSCs were evoked with a theta-glass pipette filled with 1M NaCl and 25 mM HEPES, pH 7.3, placed in the medial perforant path in the dorsal blade of the DG. A stable 15-min baseline of EPSCs evoked at ~30% of maximum peak amplitude was established before LTP was induced by theta burst stimulation (TBS; 10 theta bursts were applied at 15 s intervals, each theta burst consisted of 10 bursts at 200 ms intervals, and each burst consisted of four 100-Hz pulses). Miniature EPSCs were isolated by focally applying TTX (1 μM) to the DG through a local perfusion system (AutoMate Scientific). Miniature EPSCs were analyzed by event detection software (wDetecta; Dr. John Huguenard, Stanford University). Amplitude measurements were determined from isolated miniature EPSCs uncontaminated by other EPSCs, and 100 miniature EPSCs from each granule cell were pooled for each experimental group to generate cumulative histograms.

Field excitatory postsynaptic potentials (fEPSPs) were recorded with glass electrodes (~3MΩ tip resistance) filled with 1M NaCl and 25 mM HEPES, pH 7.3, and were evoked every 20 s with a parallel bipolar tungsten electrode (FHC). The stimulating electrode was placed in the same location (halfway between the end of the GC layer and the vertex of the two blades of the DG, ~75 μm from the GC layer) of the medial perforant path in the dorsal blade of the DG for all slices. The recording electrode was also placed in the medial perforant path but ~150 μm closer to CA3 than the recording electrode and also ~75 μm from the GC layer. fEPSPs were recorded in the presence of 50 μM picrotoxin (Tocris). Measures of synaptic strength and plasticity assessed in each slice consisted of input-output (I-O) relationships, paired pulse ratios, and LTP; these measures were recorded in the order listed. Synaptic transmission strength was assessed by generating 1-0 curves for fEPSPs; input was the peak amplitude of the fiber volley and the output was the initial slope of the fEPSP. For each slice, the fiber volley amplitude and initial slope of the fEPSP responses was measured to a range of stimulation from 25 to 800 μA, and a response curve was generated for both values. Following the 1-0 curve, stimulus strength was then adjusted to be ~30% of the maximal fEPSP. Paired pulse ratios were determined by evoking two fEPSPs 50 ms apart and dividing the initial slope of the second fEPSP by the initial slope of the first fEPSP (fEPSP2/fEPSP1). After measurement of paired-pulse ratios, a 15-min stable baseline was established, and LTP was induced by theta burst stimulation. Measurements of AMPAR- and NMDAR-mediated synaptic strength were performed on naïve slices (i.e., no LTP protocol was performed before or after I/Os). First, measurements of AMPAR-mediated synaptic strength were recorded in normal ACSF where the overwhelming majority of the initial fEPSP slope is mediated by AMPARs in a range of stimulation from 25 to 800 μA. $Mg^{2+}$-free ACSF containing 20 μM NBQX was then washed in to relieve blockade of NMDARs and block AMPARs, respectively. fEPSPs were continued to be evoked every 20 s until a stable 10-min baseline was reached, indicating all AMPARs were blocked and there was no further removal of $Mg^{2+}$ blockade of NMDARs. It typically took ~15 min to reach the beginning of the stable baseline. NMDAR-mediated fEPSPs were then evoked using the exact same set of stimulus strengths used for the AMPAR I/O curve.

Patch and recording electrodes (3-6 MΩ) were pulled from borosilicate glass capillary tubing (World Precision Instruments) on a horizontal Flaming-Brown microelectrode puller (model P-97, Sutter Instruments). Whole-cell voltage-clamp data were low-pass filtered at 6 kHz (−3 dB, eight-pole Bessel), digitally sampled at 20 kHz with a Multiclamp 700A amplifier (Molecular Devices), and acquired with a Digidata-1322A digitizer and pClamp 9.2 software (Molecular Devices). Field recordings were filtered at 2 kHz (−3 dB, eight-pole Bessel) and digitally sampled data were analyzed offline with pClamp9 software and OriginPro 8.0 (OriginLab).

Behavioral tests. Morris water maze: The maze consisted of a pool (122-cm diameter) filled with water (21±1° C.) made opaque with nontoxic white tempera paint powder; the pool was located in a room surrounded by distinct extra-maze cues. Before hidden platform training, mice were given four pre-training trials in which they had to swim in a rectangular channel (15 cm×122 cm) and mount a platform hidden 1.5 cm below the surface in the middle of the channel. Mice that did not mount the platform were gently guided to it and allowed to sit on it for 10 sec before being removed by the experimenter. The maximum time allowed per trial in this task was 90 sec. The day after pre-training, mice were trained in the circular water maze. For hidden platform training, the platform (14×14 cm) was submerged 1.5 cm below the surface. The platform location remained the same throughout hidden-platform training, but the drop location varied semi-randomly between trials. Mice received two training sessions with a 3-h intersession interval for 5 consecutive days. Each session consisted of two trials with a 10-min intertrial interval. The maximum time allowed per trial in this task was 60 sec. If a mouse did not find the platform, it was guided to it and allowed to sit on it for 10 sec. For probe trials, the platform was removed and mice were allowed to swim for 60 sec before they were removed. The drop location for probe trials was 180° from where the platform was located during hidden-platform training. After the probe trial, mice were allowed to rest for 1 day before visible platform training was performed. In the latter task, the platform location was marked with a visible cue (15 cm tall black-and-white striped pole) placed on top of the platform. Mice received two training sessions per day with a 3- to 4-h intersession interval. Each session consisted of two training trials with a 10-min intertrial interval. The maximum time allowed per trial in this task was 60 sec. For each session, the platform was moved to a new location, and the drop location varied semi-randomly between trials.

Novel object recognition: Mice were transferred to the testing room and acclimated for at least 1 h before testing. The testing was performed in a white round plastic chamber 35 cm in diameter under a red light. On day 1, mice were habituated to the testing arena for 30 min. On day 2, each mouse was presented with two identical objects in the same chamber and allowed to explore freely for 10 min. Three hours after this training session, mice were placed back into the same arena for the test session, during which they were presented with an exact replica of one of the objects used during training and with a novel, unfamiliar object of different shape and texture. Object locations were kept constant during training and test sessions for any given mouse, but objects were changed semi-randomly between mice. Arenas and objects were cleaned with 70% ethanol between each mouse. Behavior was recorded with a video tracking system (Noldus). Frequency of object interactions and time spent exploring each object were recorded for subsequent data analysis.

Novel place recognition: Mice were transferred to the testing room and acclimated for at least 1 h before testing. The testing was performed in a white plastic chamber (40×20×20 cm) under red light. On the first day, mice were habituated to the testing arena for 30 min. On the second day, each mouse was presented with two identical objects and allowed to explore freely for 10 min. Three hours after training, mice were presented with the same two objects, only this time one of the objects had been moved to a new location. Arenas and objects were cleaned with 70% ethanol between each mouse. Behavior was recorded with a video tracking system (Noldus). Frequency of object interactions and time spent exploring each object were recorded for subsequent data analysis.

Passive avoidance: The apparatus consisted of a two-compartment dark/light shuttle box separated by a guillotine door (Gemini, Avoidance System, San Diego Instruments). The dark compartment had a stainless-steel shock grid floor. During the acquisition trial, each mouse was placed in the lit chamber. After a 15-s habituation period, the door separating the light and dark chambers was opened, and the time before mice entered the dark chamber was recorded. Immediately after mice entered the dark chamber, the door was closed and an electric foot shock (0.5 mA, 2 s) was delivered by the floor grids. Ten seconds later, the mouse was removed from the dark chamber and returned to its home cage. After 24 h, the re-entrance latency was measured as in the acquisition trial, except that no foot shock was delivered. The latency to enter the dark chamber was recorded up to a maximum of 300 s.

Open field: Spontaneous locomotor activity in an open field was measured in an automated Flex-Field/Open Field Photobeam Activity System (San Diego Instruments, San Diego, Calif.). Before testing, mice were transferred to the testing room and acclimated for at least 1-hour. Mice were tested in a clear plastic chamber (41×41×30 cm) for 15 min, with two 16×16 photobeam arrays detecting horizontal and vertical movements. The apparatus was cleaned with 70% alcohol between testing of each mouse. Total movements (ambulations) in the outer periphery and center of the open field were recorded for further data analysis.

Elevated plus maze: The elevated plus maze consisted of two open (without walls) and two enclosed (with walls) arms elevated 63 cm above the ground (Hamilton-Kinder, Poway, Calif.). Mice were allowed to habituate in the testing room under dim light for 1 h before testing. During testing, mice were placed at the junction between the open and closed arms of the plus maze and allowed to explore for 5 min. The maze was cleaned with 70% alcohol between testing of each mouse. Total distance traveled and time spent in both the open and closed arms were calculated for data analysis.

Statistical analyses. Statistical analyses were performed with GraphPad Prism or SPSS v13.0 (SPSS). Data distribution was assessed by Kolmogorov-Smirnoff non-parametric test of equality. Differences between two means were assessed by paired or unpaired t test. Differences among multiple means were assessed, as indicated, by one-way, two-way or repeated-measures ANOVA, followed by Bonferroni's, Dunn's, Kruskal-Wallis's or Tukey's post-hoc test. Error bars represent s.e.m. Null hypotheses were rejected at the 0.05 level.

Results

Aβ Oligomers Interact with the Fibronectin Repeats Domain of EphB2

To determine if Aβ oligomers interact directly with EphB2, the binding of biotinylated synthetic Aβ1-42 oligomers to a purified recombinant EphB2-Fc chimeric protein was measured. Biotinylated Aβ oligomers and EphB2-Fc were pulled down together by Avidin-agarose beads and co-immunoprecipitated under cell-free conditions. EphB2 and Aβ oligomers were also co-immunoprecipitated from homogenates of primary neurons. These results suggest that Aβ oligomers interact directly with the extracellular region of EphB2.

This region comprises a ligand-binding (LB) domain, cysteine-rich (CR) domain, and fibronectin type III repeats (FN) domain (FIG. 1a). To determine which of these domains mediates the interaction with Aβ oligomers, EphB2-GST deletion mutants lacking the LB domain (ΔLB-EphB2) or the FN domain (ΔFN-EphB2) (FIG. 1a) were generated. Aβ oligomers bound effectively to FL-EphB2 and ΔLB-EphB2, but not ΔFN-EphB2 (FIG. 1b, c), suggesting that the FN domain is critical for their interaction with EphB2.

Deleting the FN domains did not affect the trafficking of EphB2 to the cell surface. FL-EphB2 and ΔFN-EphB2 were both able to phosphorylate the NMDAR subunit NR1 upon stimulation of cells with the EphB2 ligand, Fc-ephrin-B2. Thus, deleting the FN domain did not eliminate the kinase function of EphB2. As expected, deleting the LB domain prevented Fc-ephrin-B2-induced phosphorylation of NR1.

Mechanisms of Aβ-Induced EphB2 Depletion

At 3-4, but not 2, months of age, EphB2 mRNA and protein levels in hippocampus were lower in hAPP mice than in nontransgenic (NTG) controls and in humans with AD than in nondemented controls, consistent with previous findings[9].

As reported by others[16], a doublet of putative EphB2 C-terminal fragments (CTFs) of 45-50 kDa was observed in hippocampi of hAPP mice and NTG controls on WBs. Relative to NTG controls, hAPP mice showed a comparable decrease in CTFs and FL-EphB2 and no difference in the ratio of CTF1+CTF2/FL-EphB2 (hAPP:2.7±0.36, NTG:2.3±0.59, P=0.55 by t test), suggesting that pathologically elevated levels of Aβ do not affect EphB2 cleavage into CTFs.

Treating primary neuronal cultures from wild-type rats with naturally secreted Aβ oligomers caused severe EphB2 depletions by 3 days (FIG. 1d-f). Aβ oligomers also reduced EphB2 mRNA levels (FIG. 1g), but the mRNA reduction was subtle and unlikely to account for the severe EphB2 protein depletion.

Aβ-induced depletion of EphB2 was blocked by treating cells with the proteasome inhibitor lactacystin (FIG. 1h, i). Bafilomycin, an inhibitor of endosomal acidification, had no effect. Compared with Aβ treatment alone, treatment of cells with lactacystin, alone or in combination with Aβ, increased levels of ubiquitinated EphB2. These results suggest that Aβ depletes neuronal EphB2 mainly by enhancing its degradation in the proteasomal pathway.

FIGS. 1A-I. Aβ oligomers bind to the fibronectin repeats domain of EphB2 and cause degradation of EphB2 in the proteasome. a, Domain structure of full-length (FL) EphB2 and deletion constructs. Ligand-binding (LB) domain, cystein-rich (CR) region, fibronectin type III repeats (FN) domain, transmembrane (TM) region, tyrosine kinase (KD) domain, sterile alpha motif (SAM) domain, and PSD95, DLG, and ZO1 (PDZ) domain. b, Binding of Aβ dimers and trimers to different EphB2 constructs expressed in HEK cells was quantitated by immunoprecipitation with anti-GST antibodies and densitometric analysis of anti-Aβ (6E10) WB signals. c, Representative WB. d-f, Aβ-induced depletion of EphB2. Primary rat neurons were treated with vehicle (Veh, medium conditioned by untransfected control CHO cells, 3 days) or Aβ (equivalent of 60 ng/ml or 12.5 nM in 7PA2 cell-conditioned medium, for indicated times). Surface levels of EphB2 were determined by biotinylation and subsequent WB analysis, and total levels of EphB2 by WB analysis alone. Representative WBs (d). Quantitation of surface (e) and total (f) levels of EphB2. g, Primary rat neurons were treated with Veh for 6 days or with Aβ for the indicated times. EphB2 mRNA levels were determined by qRT-PCR. h, i, Primary rat neurons were pretreated for 36 h with synthetic Aβ oligomers or Veh, followed by addition of lactacystin (10 μM) or vehicle to the culture medium and incubation for another 12h. Cells were then lysed and 100 μg protein extracts immunoprecipitated with anti-EphB2 and immunoblotted with anti-EphB2. Representative WB (h) and quantitation of signals (i). For all experiments, n=3-6 wells per condition from 3 independent experiments. *P<0.05, P<0.001, *P<0.0001 versus empty bars or as indicated by brackets (Tukey test). Values are means±s.e.m.

EphB2 Depletion Impairs NMDARs

Figure 2:
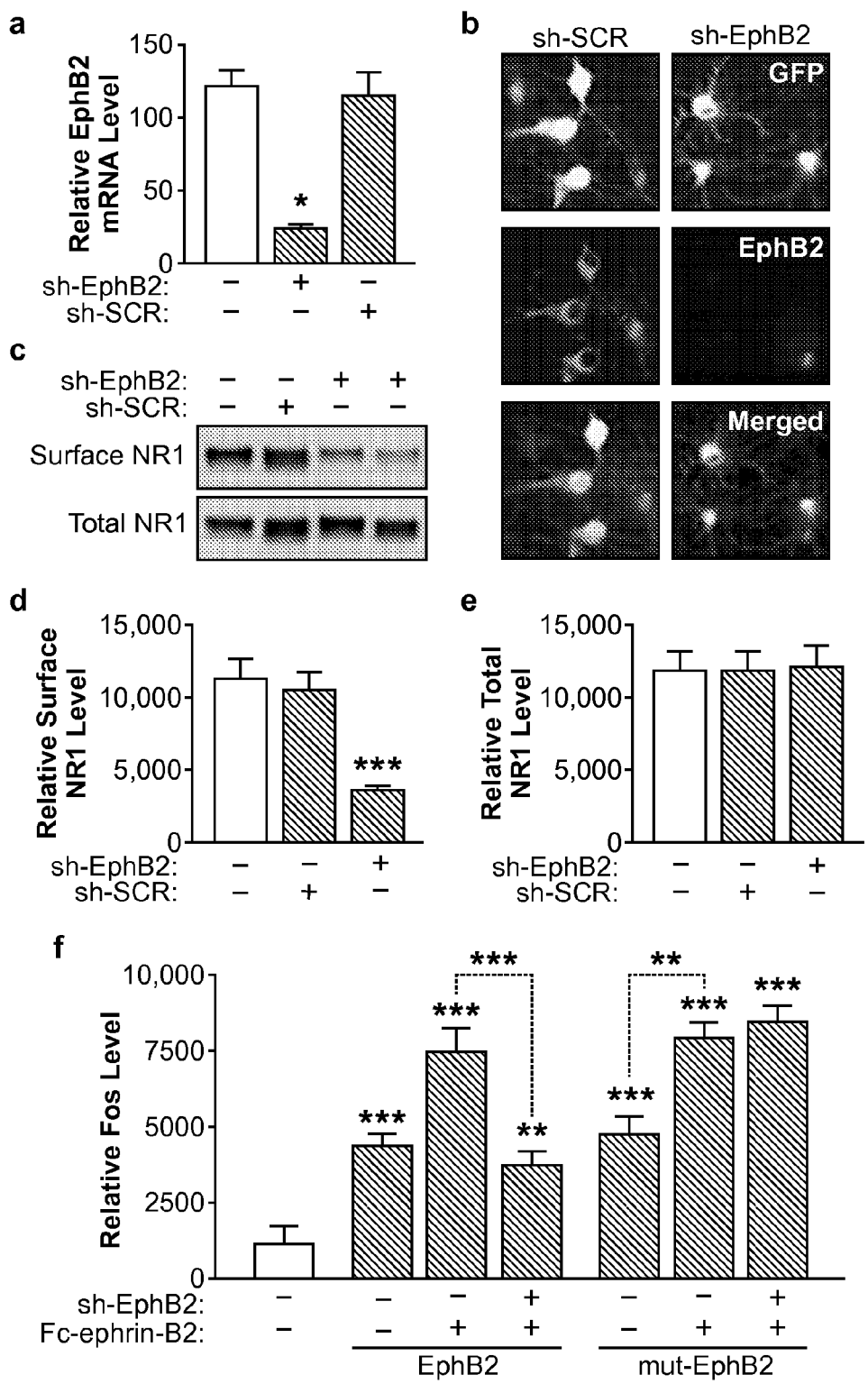
FIGS. 2A-F depict the effect of knockdown of EphB2 on surface NR1 levels and Fc-ephrin-B2-dependent Fos expression.

To determine whether EphB2 depletion per se can interfere with NMDAR-dependent functions, lentiviral vectors expressing GFP in combination with an anti-EphB2 shRNA (Lenti-sh-EphB2/GFP), or a scrambled control shRNA (Lenti-sh-SCR/GFP), were generated. In neuronal cultures, Lenti-sh-EphB2/GFP markedly reduced EphB2 mRNA and protein levels (FIG. 2a, b) and reduced surface, but not total, levels of NR1 (FIG. 2c-e), which is an essential subunit of all NMDARs. In cultures co-infected with a mutant EphB2 construct whose mRNA is resistant to sh-EphB2 (Lenti-mut-EphB2-Flag) and Lenti-sh-EphB2/GFP, neurons did not show reduced EphB2 and surface NR1, thus excluding a potential off-target effect. Next, the effects of sh-EphB2 on expression of the immediate-early gene c-fos, which depends on NMDARs and is regulated by EphB2[12], were examined. Anti-EphB2 shRNA prevented Fc-ephrin-B2-induced increases in Fos expression in neurons expressing wild-type EphB2, but not in neurons expressing mutant EphB2 (FIG. 2f). Thus, depleting EphB2 reduces NR1 expression at the neuronal surface and impairs NMDAR-dependent gene expression.

FIGS. 2A-F. Knockdown of EphB2 reduces surface NR1 levels and Fc-ephrin-B2-dependent Fos expression. a,b, Reduction of EphB2 expression by Lenti-sh-EphB2/GFP in primary rat neurons. EphB2 mRNA levels were determined by qRT-PCR (a) or neurons were immunostained for EphB2 (b). Scale bar: 20 μm. c-e, Reduction of EphB2 levels by Lenti-sh-EphB2/GFP and impact on surface NR1 levels. f, shRNA against wild-type, but not mutated, EphB2 reduces Fc-ephrin-B2-dependent Fos expression. Primary rat neurons were co-infected or not with Lenti-sh-ephB2/GFP (sh-ephB2) in combination with either Lenti-ephB2 encoding wild-type ephB2 or Lenti-mut-ephB2 (mut-ephB2) encoding a mutated ephB2 mRNA that is not recognized by sh-ephB2. Four days later, cells were stimulated with clustered multimeric recombinant Fc-ephrin-B2 ligand to activate ephB2. WB signals were quantitated by densitometry. n=3-6 wells per condition from three independent experiments. *P<0.05, P<0.001, *P<0.0001 versus empty bar or as indicated by brackets (Tukey's test). Values are mean±s.e.m.

EphB2 Depletion Impairs Synaptic Plasticity

To explore whether EphB2 depletion may account for LTP deficits in hAPP mice[8], EphB2 was reduced in the DG of NTG mice. Although granule cells (GCs) are not very susceptible to degeneration in AD, the perforant path to GC synapse is affected early and severely[17,18].

Two anti-EphB2 shRNAs effectively reduced EphB2 mRNA and protein levels in neuronal culture. Mice injected with lentiviral vectors expressing sh-EphB2-308/GFP (FIG. 3a, b) or sh-EphB2-306/GFP had lower EphB2 mRNA levels in the DG than controls. Transduction efficiencies, reflected by the proportion of CB-positive neurons co-expressing GFP, were 50-74% (mean±sem: 62.4±6.2, n=7 mice), consistent with other reports[19,20].

Figure 3:
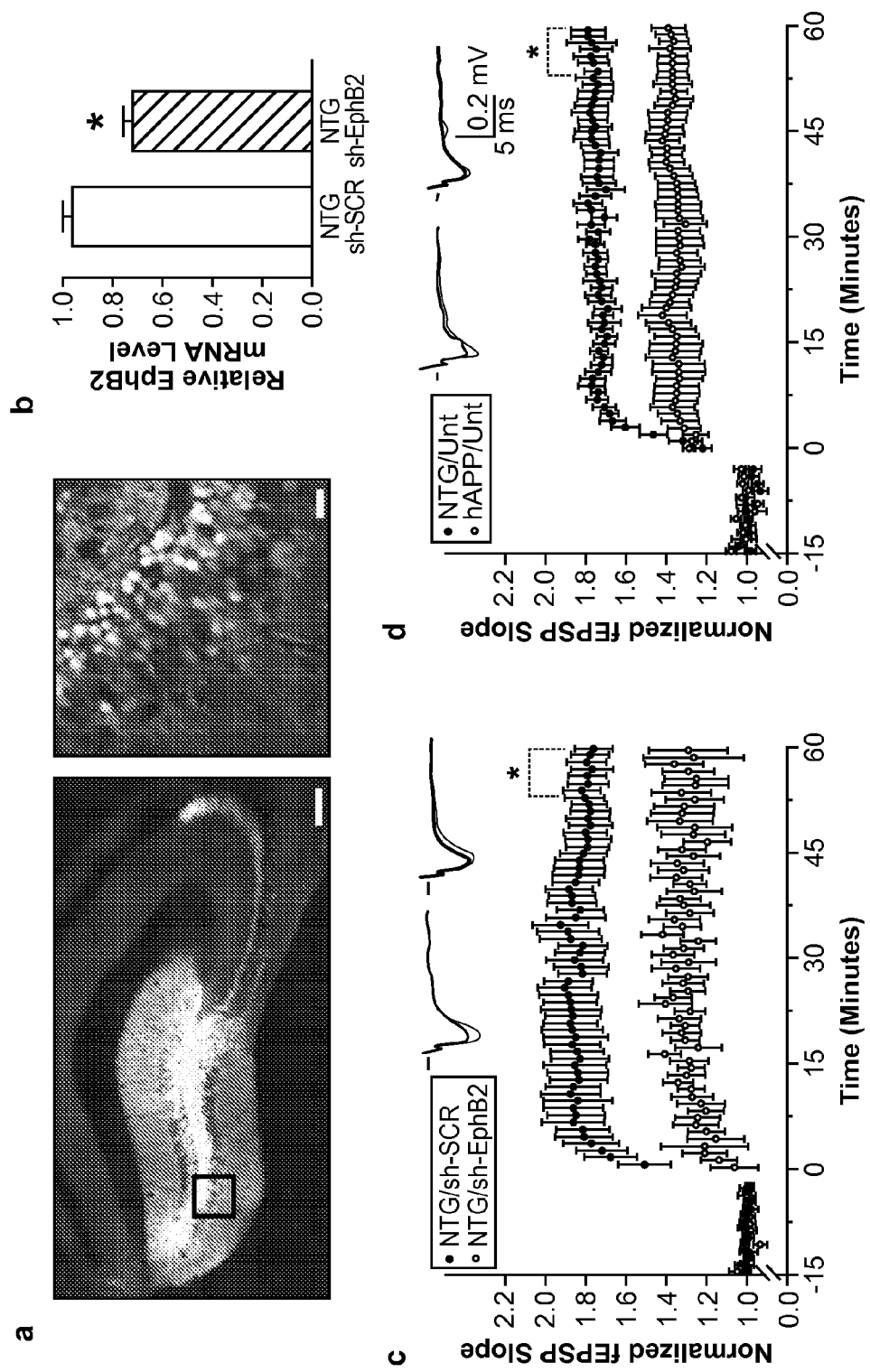
FIGS. 3A-K depict the effect of knockdown of EphB2 on long-term potentiation (LTP) in dentate gyrus (DG) granule cells (GCs) of non-transgenic (NTG) mice.

Field recordings (FIG. 3c) and whole-cell patch-clamp recordings (FIG. 3e) from DG GCs in acute hippocampal slices revealed prominent LTP deficits in Lenti-sh-EphB2/GFP-injected NTG mice. These deficits closely resembled those in untreated hAPP-J20 mice (FIG. 3d, f) and in other lines of hAPP mice[21,22]. In contrast, Lenti-sh-SCR/GFP injected NTG mice showed robust LTP in the DG (FIG. 3c, e). Whole-cell recordings from individual GFP-negative GCs in Lenti-sh-ephB2/GFP-injected mice revealed no LTP deficits, compared with GFP-negative GCs in untreated NTG mice and GFP-positive GCs in Lenti-sh-SCR/GFP-injected mice (p>0.1 by RMANOVA, n=6 neurons from 3 mice per group).

EphB2 Depletion Reduces NMDAR-Mediated Synaptic Strength

Because LTP at the medial perforant path to GC synapse depends on NMDAR activity[23], it was determined if impaired synaptic plasticity in sh-EphB2-treated NTG and untreated hAPP mice was related to a selective impairment of these glutamate receptors. NMDAR-mediated, but not AMPAR-mediated, synaptic transmission strength at this synapse was affected in sh-EphB2-treated NTG mice (FIG. 3g) and untreated hAPP mice (FIG. 3h), as determined by field recordings and analysis of input-output (I/O) curves. These alterations resulted in markedly reduced ratios of NMDAR- to AMPAR-mediated synaptic strength in sh-EphB2 treated NTG mice and untreated hAPP mice (FIG. 3j). Similar results were obtained by whole-cell recordings from individual GCs (FIG. 3i, k). To exclude the possibility that alterations in AMPAR currents contributed to the altered ratios, pharmacologically isolated, AMPAR-mediated miniature excitatory synaptic currents (mEPSCs) were recorded. The four groups of mice had comparable mEPSC peak amplitudes. Thus, similar to Aβ, EphB2 depletion probably reduces LTP by impairing NMDAR function.

FIGS. 3A-K. Knockdown of EphB2 reduces LTP in DG GCs of NTG mice. NTG mice received bilateral injections of Lenti-sh-EphB2/GFP (sh-EphB2) or Lenti-sh-SCR/GFP (sh-SCR) into the dentate gyrus (DG) at 4-5 months of age. Three weeks later, the infected brain regions were analyzed by acute slice electrophysiology, qRT-PCR, or immunostaining and fluorescence microscopy. Untreated (Unt) age-matched NTG and hAPP mice were analyzed in parallel. a, Anti-GFP immunostaining of DG showing infected neurons in Lenti-sh-EphB2/GFP treated mice. Right panel shows higher magnification image of boxed region on left. Scale bars: 100 μm (left), 25 μm (right). b, Quantitation of EphB2 mRNA by qRT-PCR demonstrating knockdown of EphB2 levels in the entire DG (reflecting levels in infected and uninfected cells) (n=5-7 mice per condition). *P<0.001 versus sh-SCR (t test). c-f, LTP at the medial perforant path to GC synapse was induced by theta burst stimulation (TBS) and measured by field recordings (c, d) or by whole-cell patch clamp from individual GFP-positive cells (e, f) in the DG. Three consecutive responses were averaged for each slice and these data were then averaged for all slices in a group to generate each point on the graph. Top traces depict the average of ten synaptic responses from a single neuron before and after TBS LTP. LTP was impaired in NTG mice treated with Lenti-sh-EphB2/GFP (sh-EphB2) compared to NTG mice treated with Lenti-sh-SCR/GFP (sh-SCR) (c, e). Similar LTP impairments were observed in untreated hAPP mice (d, f) (NTG/sh-EphB2 vs. hAPP/Unt). *P<0.05, *P<0.001 (repeated measures ANOVA and Bonferroni post-hoc test on the last 10 min of data). n=8-9 slices from 3-4 mice per treatment (c) or genotype (d). g, h, Comparison of AMPAR-mediated (left) and NMDAR-mediated (right) input-output (I/O) relationships in the medial perforant path to GC synapse of NTG mice treated with sh-EphB2 versus sh-SCR (g) and of untreated NTG (NTG/Unt) versus hAPP (hAPP/Unt) mice (h). Traces at the top show example fEPSPs for AMPAR-mediated responses or NMDAR-mediated responses. Fiber volley strengths were placed into 0.1 mV bins; fEPSP slopes were then averaged from each bin to generate the points on the graphs below. i, Example traces of evoked glutamate receptor currents from individual GCs voltage clamped at −80 or 50 mV to measure AMPAR- and NMDAR-mediated currents, respectively. j, k, Summary plot of the ratios of NMDAR I/O relationships to AMPAR I/O relationships measured by field recordings (i) or by individual GCs (k). *P<0.001 (two-way ANOVA and Bonferroni post-hoc test). n=8-9 slices from 3-4 mice per group. Values are means±s.e.m.

Increasing EphB2 Levels Rescues Synaptic Functions in hAPP Mice

Figure 4:
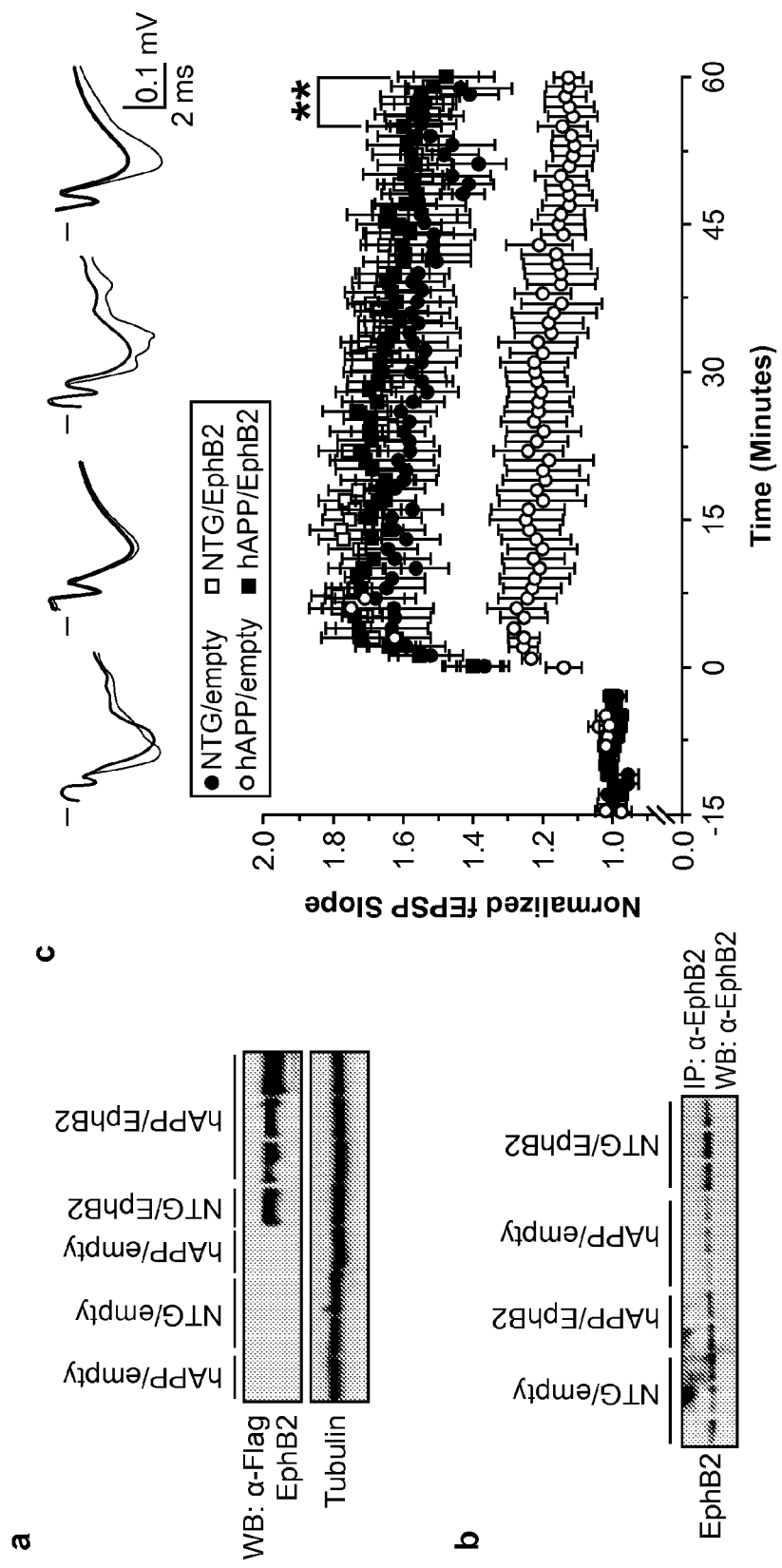
FIGS. 4A-F depict the effect of increasing EphB2 expression on synaptic plasticity in hAPP mice.
Figure 4:
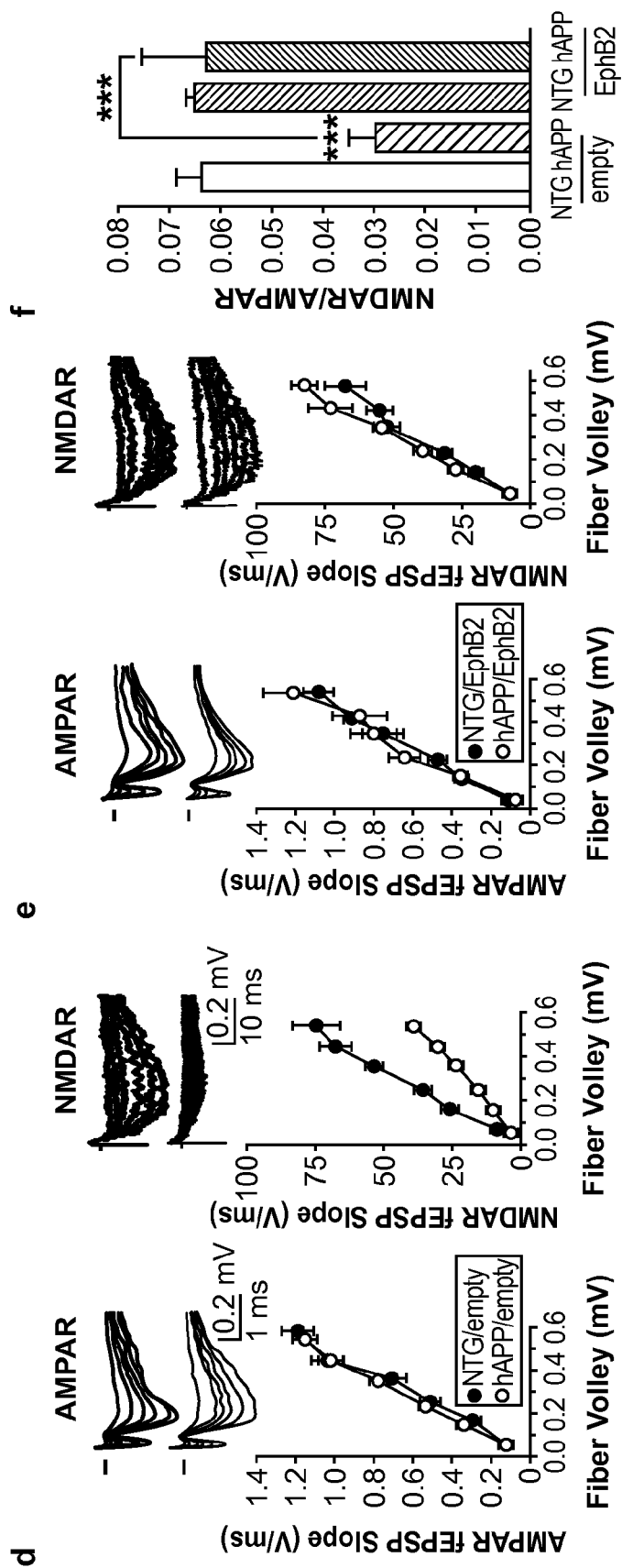

It was then determined whether increasing EphB2 expression in the DG of hAPP mice reverses their LTP deficits. For this purpose, a lentivirus expressing EphB2-Flag (Lenti-EphB2-Flag) was used. Lenti-EphB2-Flag-treated hAPP and NTG mice had comparable EphB2-Flag expression levels in the DG (FIG. 4a). Lenti-empty-treated NTG mice and Lenti-EphB2-Flag-treated hAPP mice had comparable DG levels of total (endogenous and exogenous) EphB2 (FIG. 4b), suggesting that EphB2 levels in hAPP mice were normalized. EphB2 levels were lower in Lenti-empty-injected hAPP mice and higher in Lenti-EphB2-Flag-injected NTG mice (FIG. 4b). Increasing DG EphB2 levels in two independent cohorts of hAPP mice reversed LTP deficits in both groups (combined data shown in FIG. 4c). Overexpression of EphB2 in NTG mice did not alter LTP (FIG. 4c).

Lenti-EphB2-Flag-treated mice showed a trend towards lower Aβ levels in the DG, but this effect did not reach statistical significance. At analysis, hAPP mice were 4-5 months old and had not yet formed plaques, excluding EphB2 effects on plaque formation. To determine if the LTP rescue was due to improved NMDAR function, AMPAR- and NMDAR-mediated synaptic strength were again measured. Increasing EphB2 levels in the DG of hAPP mice fully reversed their deficits in NMDAR-mediated synaptic strength without changing AMPAR-mediated synaptic strength (FIG. 4d, e), thus, normalizing the balance between NMDAR- and AMPAR-mediated synaptic strengths (FIG. 4f). Overexpressing EphB2 did not alter NMDAR- or AMPAR-mediated synaptic strength in NTG mice (FIG. 4d-f).

Increasing EphB2 expression in GCs did not reverse impairments in paired pulse modification at the perforant path to GC synapse or in synaptic strength at the Schaffer collateral to CA1 pyramidal cell synapse.

FIGS. 4A-F. Increasing EphB2 expression rescues synaptic plasticity in hAPP mice. a,b, Two-month-old NTG and hAPP mice received bilateral injections of Lenti-empty or Lenti-EphB2-Flag into the dentate gyrus (DG) (n=9-12 mice per genotype and treatment). Two months after the injection, DG were microdissected for determination of levels of EphB2-Flag (a) and total EphB2 (b) by WB analysis with anti-Flag and anti-EphB2 antibodies, respectively. c, Normalization of LTP (measured as in FIG. 3c, d) in hAPP mice treated with EphB2-Flag. P<0.01 (repeated-measures ANOVA and Bonferroni post-hoc test on the last 10 min of data). The following ratios represent the numbers of slices/mice from which the recordings were obtained. NTG-Empty: 8/4, hAPP-Empty:6/3, NTG-EphB2:13/6, hAPP-EphB2:20/8. d, e, Comparison of AMPAR-mediated (left) and NMDAR-mediated (right) input-ouput (I/O) relationships in the medial perforant path to GC synapse of NTG and hAPP mice treated with Lenti-empty (d) or Lenti-EphB2-Flag (e). Recording conditions were as in FIG. 3e, f, Summary plot of the ratios of NMDAR I/O relationships to AMPAR I/O relationships. *P<0.001 (two-way ANOVA and Bonferroni post-hoc test). Numbers of slices/mice were NTG-empty:8/4, hAPP/empty:6/3, NTG/EphB2:6/3, hAPP/EphB2:8/4. Values are means±s.e.m.

Increasing EphB2 Levels Ameliorates Cognitive Deficits in hAPP Mice

In light of the above results, it was asked whether increasing EphB2 levels in the DG would also reverse learning and memory deficits in hAPP mice[24-27]. Lenti-EphB2-Flag, or Lenti-empty, was injected bilaterally into the DG of hAPP and NTG mice; and the mice were analyzed behaviorally 2 months later.

Figure 5:
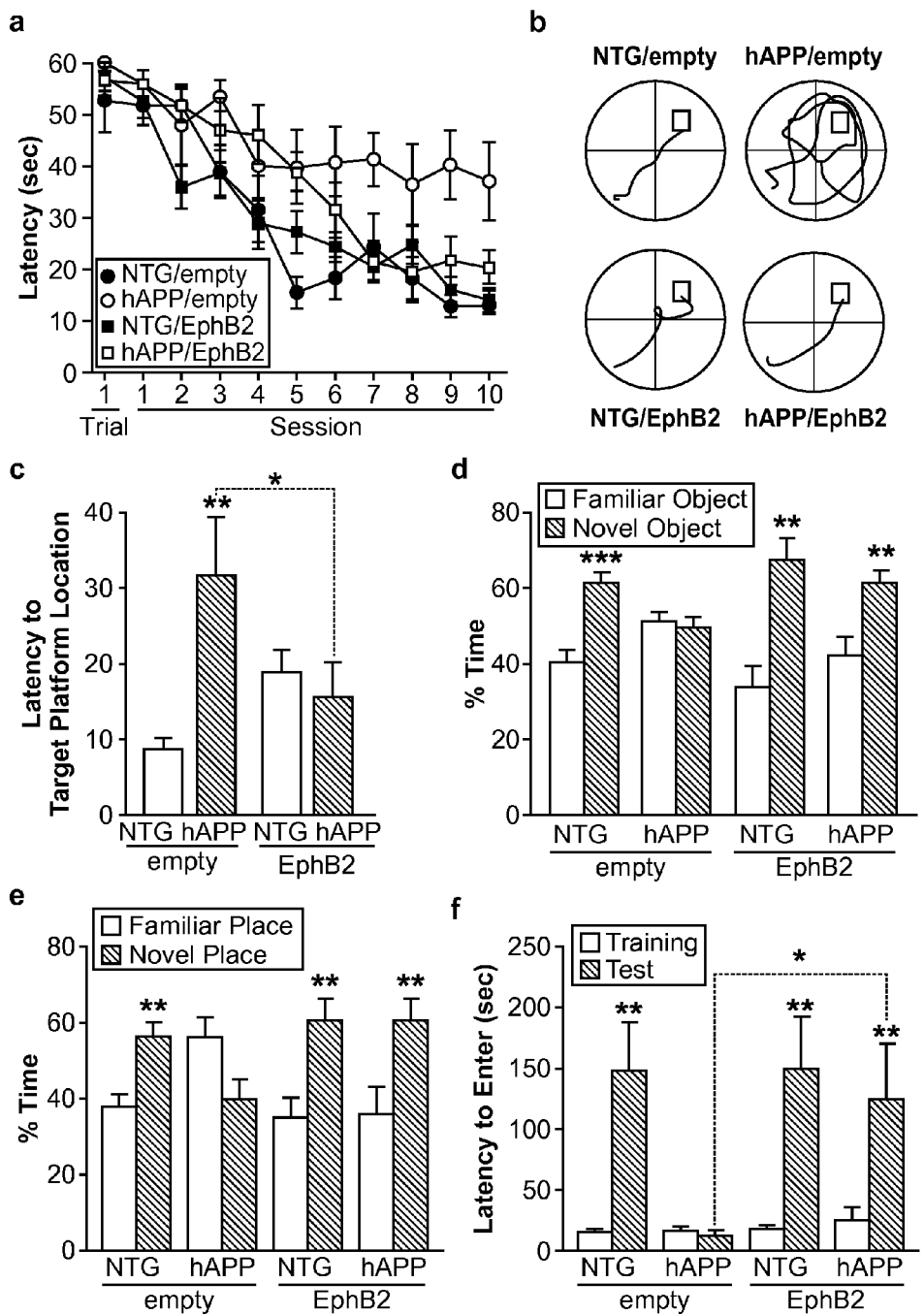
FIGS. 5A-F depict the effect of increasing EphB2 expression in the DG on learning and memory deficits in hAPP mice.

Spatial learning and memory in the Morris water maze is strongly affected by DG impairments[28]. In the spatial, hidden-platform component of this test, Lenti-EphB2-Flag-treated, but not Lenti-empty-treated, hAPP mice performed at control levels (FIG. 5a, b). Overexpressing EphB2 did not alter learning in NTG mice (FIG. 5a, b). All groups of mice learned similarly well in the cued-platform component of the test.

In a probe trial, Lenti-empty-treated, but not Lenti-EphB2-Flag-treated, hAPP mice took longer to reach the original platform location than Lenti-empty-treated NTG controls (FIG. 5c). In this test, Lenti-EphB2-Flag-treated NTG mice performed slightly worse than Lenti-empty treated NTG mice (FIG. 5c), although this trend did not reach statistical significance (P=1.0 by one-way ANOVA and Bonferroni post-hoc test).

In the novel object recognition test, Lenti-EphB2 treated, but not Lenti-empty-treated, hAPP mice spent more time exploring the novel object (FIG. 5d). In the novel place recognition task, Lenti-EphB2-treated, but not Lenti-empty-treated, hAPP mice spent more time exploring the object whose location had changed (FIG. 5e). Thus, increasing EphB2 expression in the DG of hAPP mice ameliorates deficits in both spatial and nonspatial learning and memory.

Finally, passive avoidance learning, which also depends, at least in part, on hippocampal functions[29,30], was assessed. During training, escape latencies were similar across groups (FIG. 5f). However, 24 h later, Lenti-empty-treated hAPP mice were severely impaired, whereas all other groups performed well (FIG. 5f). Increasing DG EphB2 levels in hAPP mice did not reverse behavioral deficits that are likely caused by impairments of other brain regions, including hyperactivity in the open field and disinhibition in the elevated plus maze.

FIGS. 5A-F. Increasing EphB2 expression in the DG ameliorates learning and memory deficits in hAPP mice. Four- to 5-month-old NTG and hAPP mice were analyzed behaviorally 2 months after they received bilateral injections of Lenti-empty or Lenti-EphB2-Flag in the DG (n=9 mice per genotype and treatment). a, Learning curves during spatial training in the Morris water maze. The time (latency) for each mouse to reach the hidden platform was recorded. Trial 1 represents performance on the first trial, and subsequent sessions represent the average of two training trials. Lenti-empty treated hAPP mice had longer latencies and traveled farther (not shown) to find the hidden platform than all other groups ($P<0.0001$, repeated-measures ANOVA). b, Representative paths from the last session of hidden-platform training c, Time it took mice to reach the target platform location during a probe trial (platform removed) 24 h after the last hidden-platform training. *$P<0.05$, $P<0.01$ versus first bar or as indicated by bracket (one-way ANOVA followed by Bonferroni post-hoc test). d, Object recognition memory as reflected by the percent time mice spent exploring a familiar versus a novel object during a 10-min test session. $P<0.01$, *$P<0.001$ versus familiar object (paired t test). e, Spatial location memory as reflected by the percent time mice spent exploring familiar objects whose locations were or were not altered. $P<0.01$ versus familiar place (t test). f, Passive avoidance memory assessed 24 h after training mice in a light/dark chamber as reflected by the time it took them to re-enter the dark chamber during a 5-min test session. *$P<0.05$, **$P<0.01$, versus training or as indicated by bracket (one-way nonparametric Kruskal-Wallis test followed by Dunn's post test). Values are means±s.e.m.

REFERENCES

1. Walsh, D. M. & Selkoe, D. J. Deciphering the molecular basis of memory failure in Alzheimer's disease. *Neuron* 44, 181-193 (2004).
2. Shankar, G. M. et al. Amyloid-beta protein dimers isolated directly from Alzheimer's brains impair synaptic plasticity and memory. *Nat. Med.* 14, 837-842 (2008).
3. Kamenetz, F. et al. APP processing and synaptic function. *Neuron* 37, 925-937 (2003).
4. Malenka, R. C. & Bear, M. F. LTP and LTD: An embarrassment of riches. *Neuron* 44, 5-21 (2004).
5. Ikonomovic, M. D. et al. Distribution of glutamate receptor subunit NMDAR1 in the hippocampus of normal elderly and patients with Alzheimer's disease. *Exp. Neurol.* 160, 194-204 (1999).
6. Sze, C., Bi, H., Kleinschmidt-DeMasters, B. K., Filley, C. M. & Martin, L. J. N-Methyl-D-aspartate receptor subunit proteins and their phosphorylation status are altered selectively in Alzheimer's disease. *J. Neurol. Sci.* 182, 151-159 (2001).
7. Palop, J. J. et al. Vulnerability of dentate granule cells to disruption of Arc expression in human amyloid precursor protein transgenic mice. *J. Neurosci.* 25, 9686-9693 (2005).
8. Palop, J. J. et al. Aberrant excitatory neuronal activity and compensatory remodeling of inhibitory hippocampal circuits in mouse models of Alzheimer's disease. *Neuron* 55, 697-711 (2007).
9. Simon, A. M. et al. Early changes in hippocampal Eph receptors precede the onset of memory decline in mouse models of Alzheimer's disease. *J. Alzheimers Dis.* 17, 773-786 (2009).
10. Henderson, J. T. et al. The receptor tyrosine kinase EphB2 regulates NMDA-dependent synaptic function. *Neuron* 32, 1041-1056 (2001).
11. Dalva, M. B. et al. EphB receptors interact with NMDA receptors and regulate excitatory synapse formation. *Cell* 103, 945-956 (2000).
12. Takasu, M. A., Dalva, M. B., Zigmond, R. E. & Greenberg, M. E. Modulation of NMDA receptor-dependent calcium influx and gene expression through EphB receptors. *Science* 295, 491-495 (2002).
13. Chen, Y., Fu, A. K. & Ip, N.Y. Bidirectional signaling of ErbB and Eph receptors at synapses. *Neuron Glia Biol.* 4, 211-221 (2008).
14. Grunwald, I. C. et al. Kinase-independent requirement of EphB2 receptors in hippocampal synaptic plasticity. *Neuron* 32, 1027-1040 (2001).

15. Fleischmann, A. et al. Impaired long-term memory and NR2A-type NMDA receptor-dependent synaptic plasticity in mice lacking c-Fos in the CNS. *J. Neurosci.* 23, 9116-9122 (2003).
16. Litterst, C. et al. Ligand binding and calcium influx induce distinct ectodomain/gamma-secretase-processing pathways of EphB2 receptor. *J. Biol. Chem.* 282, 16155-16163 (2007).
17. Wakabayashi, K., Honer, W. G. & Masliah, E. Synapse alterations in the hippocampal-entorhinal formation in Alzheimer's disease with and without Lewy body disease. *Brain Res.* 667, 24-32 (1994).
18. Scheff, S. W. & Price, D. A. Alzheimer's disease-related alterations in synaptic density: Neocortex and hippocampus. *J. Alzheimers Dis.* 9, 101-115 (2006).
19. Mueller-Steiner, S. et al. Anti-amyloidogenic and neuroprotective functions of cathepsin B: Implications for Alzheimer's disease. *Neuron* 51, 703-714 (2006).
20. Sun, B. et al. Imbalance between GABAergic and glutamatergic transmissions impairs adult neurogenesis in an animal model of Alzheimer's disease. *Cell Stem Cell* 5, 624-633 (2009).
21. Shemer, I. et al. Non-fibrillar b-amyloid abates spike-timing-dependent synaptic potentiation at excitatory synapses in layer 2/3 of the neocortex by targeting postsynaptic AMPA receptors. *Eur. J. Neurosci.* 23, 2035-2047 (2006).
22. Ashe, K. H. & Zahs, K. R. Probing the biology of Alzheimer's disease in mice. *Neuron* 66, 631-645 (2010).
23. Colino, A. & Malenka, R. C. Mechanisms underlying induction of long-term potentiation in rat medial and lateral perforant paths in vitro. *J. Neurophysiol.* 69, 1150-1159 (1993).
24. Harris, J. A. et al. Many neuronal and behavioral impairments in transgenic mouse models of Alzheimer's disease are independent of caspase cleavage of the amyloid precursor protein. *J. Neurosci.* 30, 372-381 (2010).
25. Sanchez-Mejia, R. O. et al. Phospholipase A2 reduction ameliorates cognitve deficits in mouse model of Alzheimer's disease. *Nat. Neurosci.* 11, 1311-1318 (2008).
26. Meilandt, W. J. et al. Enkephalin elevations contribute to neuronal and behavioral impairments in a transgenic mouse model of Alzheimer's disease. *J. Neurosci.* 28, 5007-5017 (2008).
27. Roberson, E. D. et al. Reducing endogenous tau ameliorates amyloid β-induced deficits in an Alzheimer's disease mouse model. *Science* 316, 750-754 (2007).
28. Nguyen, P. V., Abel, T., Kandel, E. R. & Bourtchouladze, R. Strain-dependent differences in LTP and hippocampus-dependent memory in inbred mice. *Learn. Mem.* 7, 170-179 (2000).
29. Nakajima, R. et al. Comprehensive behavioral phenotyping of calpastatin-knockout mice. *Mol. Brain* 1, 7 (2008).
30. Potter, M. C. et al. Reduction of endogenous kynurenic acid formation enhances extracellular glutamate, hippocampal plasticity, and cognitive behavior. *Neuropsychopharmacology* 35, 1734-1742 (2010).
31. Terashima, A. et al. An essential role for PICK1 in NMDA receptor-dependent bidirectional synaptic plasticity. *Neuron* 57, 872-882 (2008).
32. Snyder, E. M. et al. Regulation of NMDA receptor trafficking by amyloid-β. *Nat. Neurosci.* 8, 1051-1058 (2005).
33. Kurup, P. et al. Abeta-mediated NMDA receptor endocytosis in Alzheimer's disease involves ubiquitination of the tyrosine phosphatase STEP61. *J. Neurosci.* 30, 5948-5957 (2010).
34. Bonifazi, P. et al. GABAergic hub neurons orchestrate synchrony in developing hippocampal networks. *Science* 326, 1419-1424 (2009).
35. Han, J. H. et al. Selective erasure of a fear memory. *Science* 323, 1492-1496 (2009).
36. Li, C. Y., Poo, M. M. & Dan, Y. Burst spiking of a single cortical neuron modifies global brain state. *Science* 324, 643-646 (2009).
37. Rockenstein, E. M. et al. Levels and alternative splicing of amyloid b protein precursor (APP) transcripts in brains of transgenic mice and humans with Alzheimer's disease. *J. Biol. Chem.* 270, 28257-28267 (1995).
38. Mucke, L. et al. High-level neuronal expression of $A\beta_{1-42}$ in wild-type human amyloid protein precursor transgenic mice: Synaptotoxicity without plaque formation. *J. Neurosci.* 20, 4050-4058 (2000).
39. Koo, E. H. & Squazzo, S. L. Evidence that production and release of amyloid b-protein involves the endocytic pathway. *J. Biol. Chem.* 269, 17386-17389 (1994).
40. Walsh, D. M. et al. Naturally secreted oligomers of amyloid β protein potently inhibit hippocampal long-term potentiation in vivo. *Nature* 416, 535-539 (2002).
41. Franklin, K. B. J. & Paxinos, G. *The mouse brain in stereotaxic coordinates*. (Academic Press, Inc., 1997).
42. Xia, Z., Dudek, H., Miranti, C. K. & Greenberg, M. E. Calcium influx via the NMDA receptor induces immediate early gene transcription by a MAP kinase/ERK-dependent mechanism. *J. Neurosci.* 16, 5425-5436 (1996).
43. Lauren, J., Gimbel, D. A., Nygaard, H. B., Gilbert, J. W. & Strittmatter, S. M. Cellular prion protein mediates impairment of synaptic plasticity by amyloid-beta oligomers. *Nature* 457, 1128-1132 (2009).
44. Alfa Cisse, M. et al. M1 and M3 muscarinic receptors control physiological processing of cellular prion by modulating ADAM17 phosphorylation and activity. *J. Neurosci.* 27, 4083-4092 (2007).
45. Wu, J., Rush, A., Rowan, M. J. & Anwyl, R. NMDA receptor- and metabotropic glutamate receptor-dependent synaptic plasticity induced by high frequency stimulation in the rat dentate gyrus in vitro. *J. Physiol.* 533, 745-755 (2001).
46. Raber, J. et al. Hypothalamic-pituitary-adrenal function in $Apoe^{-/-}$ mice: Possible role in behavioral and metabolic alterations. *J. Neurosci.* 20, 2064-2071 (2000).
47. Raber, J., LeFevour, A., Buttini, M. & Mucke, L. Androgens protect against Apolipoprotein E4-induced cognitive deficits. *J. Neurosci.* 22, 5204-5209 (2002).
48. Dere, E., Huston, J. P. & De Souza Silva, M. A. Episodic-like memory in mice: Simultaneous assessment of object, place and temporal order memory. *Brain Res. Brain Res. Protoc.* 16, 10-19 (2005).
49. Benice, T., Rizk, A., Kohama, S., Pfankuch, T. & Raber, J. Sex-differences in age-related cognitive decline in C57BL/6J mice associated with increased brain microtubule-associated protein 2 and synaptophysin immunoreactivity. *Neuroscience* 137, 413-423 (2006).
50. Johnson-Wood, K. et al. Amyloid precursor protein processing and $A\beta_{42}$ deposition in a transgenic mouse model of Alzheimer disease. *Proc. Natl. Acad. Sci. USA* 94, 1550

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating an amyloid-beta-associated neurodegenerative disease in an individual, the method comprising administering to the individual a nucleic acid expression vector comprising a nucleotide sequence encoding an EphB2 polypeptide.

2. The method of claim 1, wherein the expression vector is a virus-based vector.

3. The method of claim 1, wherein the nucleotide sequence encoding the EphB2 polypeptide is operably linked to a neuron-specific transcriptional control element, a microglia-specific transcriptional control element, an oligocyte-specific transcriptional control element, or an astroglia-specific transcriptional control element.

4. The method of claim 1, wherein the EphB2 polypeptide comprises an amino acid sequence having at least about 85% amino acid sequence identity to the amino acid sequence set forth in SEQ ID NO:2.

5. The method of claim 1, wherein the EphB2 polypeptide comprises an amino acid sequence having at least about 95% amino acid sequence identity to the amino acid sequence set forth in SEQ ID NO:2.

6. The method of claim 1, wherein the amyloid-beta-associated neurodegenerative disease is Alzheimer's disease.

7. The method of claim 1, wherein the individual is a human.

8. The method of claim 1, wherein said administering is intracranial.

9. A method for increasing the level and/or function of an EphB2 polypeptide in a neuron, the method comprising introducing into the neuron a nucleic acid expression vector comprising a nucleotide sequence encoding an EphB2 polypeptide.

10. The method of claim 9, wherein the neuron is a dentate gyrus granule cell.

11. The method of claim 9, wherein the expression vector is a virus-based vector.

12. The method of claim 9, wherein the nucleotide sequence encoding the EphB2 polypeptide is operably linked to a neuron-specific transcriptional control element, a microglia-specific transcriptional control element, or an astroglia-specific transcriptional control element.

13. The method of claim 9, wherein the EphB2 polypeptide comprises an amino acid sequence having at least about 85% amino acid sequence identity to the amino acid sequence set forth in SEQ ID NO:2.

14. The method of claim 9, wherein the EphB2 polypeptide comprises an amino acid sequence having at least about 95% amino acid sequence identity to the amino acid sequence set forth in SEQ ID NO:2.

15. The method of claim 9, wherein increasing the function of the EphB2 increases NMDA receptor activity in the cell.

16. The method of claim 15, wherein EphB2 increases NMDA receptor activity by phosphorylating the NDMA receptor.

17. The method of claim 15, wherein EphB2 increases NMDA receptor activity in a tyrosine kinase-independent manner.

18. A method of identifying a candidate agent for the treatment of an amyloid-beta-induced neurodegenerative disease, the method comprising:
    a) contacting an EphB2 polypeptide and an amyloid-beta polypeptide with a test agent; and
    b) determining the effect, if any, of the test agent on binding of the amyloid-beta polypeptide to the EphB2 polypeptide,
    wherein a test agent that reduces binding of the amyloid-beta polypeptide to the EphB2 polypeptide is a candidate agent for treating an amyloid-beta-induced neurodegenerative disease.

19. A method of identifying a candidate agent for the treatment of an amyloid-beta-induced neurodegenerative disease, the method comprising:
    a) contacting a cell that expresses an EphB2 polypeptide with a test agent; and
    b) determining the effect, if any, of the test agent on the level of the EphB2 in the cell, wherein a test agent that increases the level of the EphB2 polypeptide in the cell is a candidate agent for treating an amyloid-beta-induced neurodegenerative disease.

20. The method of claim 19, wherein the cell is a neuron.

21. The method of claim 19, wherein the EphB2 polypeptide comprises an amino acid sequence having at least about 85% amino acid sequence identity to the amino acid sequence set forth in SEQ ID NO: 2.

22. The method of claim 19, wherein the EphB2 polypeptide comprises an amino acid sequence having at least about 95% amino acid sequence identity to the amino acid sequence set forth in SEQ ID NO:2.

23. The method of claim 18, wherein the EphB2 polypeptide comprises an amino acid sequence having at least about 85% amino acid sequence identity to the amino acid sequence set forth in SEQ ID NO:2.

24. The method of claim 18, wherein the EphB2 polypeptide comprises an amino acid sequence having at least about 95% amino acid sequence identity to the amino acid sequence set forth in SEQ ID NO:2.

25. The method of claim 18, wherein the amyloid-beta polypeptide comprises the amino acid sequence set forth in SEQ ID NO:5.

26. The method of claim 18, wherein the amyloid-beta polypeptide comprises a moiety that provides for detection, purification, or immunoprecipitation.

27. The method of claim 18, wherein EphB2 polypeptide comprises a moiety that provides for detection, purification, or immunoprecipitation.

28. The method of claim 1, wherein said administering is systemic.

29. The method of claim 1, wherein said expression vector is formulated with one or more agents that facilitate crossing the blood-brain barrier.

* * * * *

SEQUENCE LISTING

<160> NUMBER OF SEQ ID NOS: 18

<210> SEQ ID NO 1
<211> LENGTH: 4869
<212> TYPE: DNA
<213> ORGANISM: Homo sapiens

<400> SEQUENCE: 1

| | | | | | |
|---|---|---|---|---|---|
| cattctgctg | gctgcgcggt | ggcggcggct | gtgtgtgcgc | cgcgccttgc | cgccccccct | 60 |
| ggccccccga | gcccggggcg | cgcgctcccg | cccgggccgt | ccgggccccg | cggcgccgcg | 120 |
| gcccgaggcc | ccgggaagcg | cagccatggc | tctgcgcagg | ctgggggccg | cgctgctgct | 180 |
| gctgccgctg | ctcgccgccg | tggaagaaac | gctaatggac | tccactacag | cgactgctga | 240 |
| gctgggctgg | atggtgcatc | ctccatcagg | gtgggaagag | gtgagtggct | acgatgagaa | 300 |
| catgaacacg | atccgcacgt | accaggtgtg | caacgtgttt | gagtcaagcc | agaacaactg | 360 |
| gctacggacc | aagtttatcc | ggcgccgtgg | cgcccaccgc | atccacgtgg | agatgaagtt | 420 |
| ttcggtgcgt | gactgcagca | gcatccccag | cgtgcctggc | tcctgcaagg | agaccttcaa | 480 |
| cctctattac | tatgaggctg | actttgactc | ggccaccaag | accttcccca | actggatgga | 540 |
| gaatccatgg | gtgaaggtgg | ataccattgc | agccgacgag | agcttctccc | aggtggacct | 600 |
| gggtggccgc | gtcatgaaaa | tcaacaccga | ggtgcggagc | ttcggacctg | tgtcccgcag | 660 |
| cggcttctac | ctggccttcc | aggactatgg | cggctgcatg | tccctcatcg | ccgtgcgtgt | 720 |
| cttctaccgc | aagtgccccc | gcatcatcca | gaatggcgcc | atcttccagg | aaaccctgtc | 780 |
| gggggctgag | agcacatcgc | tggtggctgc | ccggggcagc | tgcatcgcca | atgcggaaga | 840 |
| ggtggatgta | cccatcaagc | tctactgtaa | cggggacggc | gagtggctgg | tgcccatcgg | 900 |
| gcgctgcatg | tgcaaagcag | gcttcgaggc | cgttgagaat | ggcaccgtct | gccgaggttg | 960 |
| tccatctggg | actttcaagg | ccaaccaagg | ggatgaggcc | tgtacccact | gtcccatcaa | 1020 |
| cagccggacc | acttctgaag | gggccaccaa | ctgtgtctgc | cgcaatggct | actacagagc | 1080 |
| agacctggac | cccctggaca | tgccctgcac | aaccatcccc | tccgcgcccc | aggctgtgat | 1140 |
| ttccagtgtc | aatgagacct | ccctcatgct | ggagtggacc | cctcccgcg | actccggagg | 1200 |
| ccgagaggac | ctcgtctaca | acatcatctg | caagagctgt | ggctcgggcc | ggggtgcctg | 1260 |
| cacccgctgc | ggggacaatg | tacagtacgc | accacgccag | ctaggcctga | ccgagccacg | 1320 |
| catttacatc | agtgacctgc | tggcccacac | ccagtacacc | ttcgagatcc | aggctgtgaa | 1380 |
| cggcgttact | gaccagagcc | ccttctcgcc | tcagttcgcc | tctgtgaaca | tcaccaccaa | 1440 |
| ccaggcagct | ccatcggcag | tgtccatcat | gcatcaggtg | agccgcaccg | tggacagcat | 1500 |
| taccctgtcg | tggtcccagc | cggaccagcc | caatggcgtg | atcctggact | atgagctgca | 1560 |
| gtactatgag | aaggagctca | gtgagtacaa | cgccacagcc | ataaaaagcc | ccaccaacac | 1620 |
| ggtcaccgtg | cagggcctca | agccggcgc | catctatgtc | ttccaggtgc | gggcacgcac | 1680 |
| cgtggcaggc | tacgggcgct | acagcggcaa | gatgtacttc | cagaccatga | cagaagccga | 1740 |
| gtaccagaca | agcatccagg | agaagttgcc | actcatcatc | ggctcctcgg | ccgctggcct | 1800 |
| ggtcttcctc | attgctgtgg | ttgtcatcgc | catcgtgtgt | aacagaagac | gggggttga | 1860 |
| gcgtgctgac | tcggagtaca | cggacaagct | gcaacactac | accagtggcc | acatgacccc | 1920 |
| aggcatgaag | atctacatcg | atccttcac | ctacgaggac | cccaacgagg | cagtgcggga | 1980 |
| gtttgccaag | gaaattgaca | tctcctgtgt | caaaattgag | caggtgatcg | gagcagggga | 2040 |
| gtttggcgag | gtctgcagtg | gccacctgaa | gctgccaggc | aagagagaga | tctttgtggc | 2100 |

```
catcaagacg ctcaagtcgg gctacacgga gaagcagcgc cgggacttcc tgagcgaagc    2160
ctccatcatg ggccagttcg accatcccaa cgtcatccac ctggagggtg tcgtgaccaa    2220
gagcacacct gtgatgatca tcaccgagtt catggagaat ggctccctgg actccttct    2280 ccggcaaaac gatgggcagt tcacagtcat ccagctggtg gcatgcttc ggggcatcgc    2340 agctggcatg aagtacctgg cagacatgaa ctatgttcac cgtgacctgg ctcccgcaa    2400 catcctcgtc aacagcaacc tggtctgcaa ggtgtcggac tttgggctct cacgctttct    2460
agaggacgat acctcagacc ccacctacac cagtgccctg gcggaaaga tccccatccg    2520 ctggacagcc ccgaagcca tccagtaccg gaagttcacc tcggccagtg atgtgtggag    2580
ctacggcatt gtcatgtggg aggtgatgtc ctatgggag cggccctact gggacatgac    2640
caaccaggat gtaatcaatg ccattgagca ggactatcgg ctgccaccgc ccatggactg    2700
cccgagcgcc ctgcaccaac tcatgctgga ctgttggcag aaggaccgca accaccggcc    2760
caagttcggc caaattgtca acacgctaga caagatgatc cgcaatccca acagcctcaa    2820
agccatggcg cccctctcct ctggcatcaa cctgccgctg ctggaccgca cgatccccga    2880
ctacaccagc tttaacacgg tggacgagtg gctggaggcc atcaagatgg ggcagtacaa    2940
ggagagcttc gccaatgccg gcttcacctc ctttgacgtc gtgtctcaga tgatgatgga    3000
ggacattctc cggttggggg tcactttggc tggccaccag aaaaaaatcc tgaacagtat    3060
ccaggtgatg cgggcgcaga tgaaccagat tcagtctgtg gaggtttgac attcacctgc    3120
ctcggctcac ctcttcctcc aagccccgcc cctctgccc cacgtgccgg ccctcctggt    3180
gctctatcca ctgcagggcc agccactcgc caggaggcca cgggccacgg gaagaaccaa    3240
gcggtgccag ccacgagacg tcaccaagaa aacatgcaac tcaaacgacg aaaaaaaaa    3300 gggaatggga aaaagaaaa cagatcctgg gaggggcgg gaaatacaag gaatattttt    3360
taaagaggat tctcataagg aaagcaatga ctgttcttgc ggggataaa aagggcttg    3420 ggagattcat gcgatgtgtc caatcggaga caaaagcagt ttctctccaa ctccctctgg    3480
gaaggtgacc tggccagagc caagaaacac tttcagaaaa acaaatgtga aggggagaga    3540
caggggccgc ccttggctcc tgtccctgct gctcctctag gcctcactca acaaccaagc    3600
gcctggagga cgggacagat ggacagacag ccaccctgag aacccctctg gaaaatcta    3660 ttcctgccac cactgggcaa acagaagaat ttttctgtct ttggagagta ttttagaaac    3720
tccaatgaaa gacactgttt ctcctgttgg ctcacagggc tgaaaggggc ttttgtcctc    3780
ctgggtcagg agaacgcgg ggaccccaga aaggtcagcc ttcctgagga tgggcaaccc    3840
ccaggtctgc agctccaggt acatatcacg cgcacagcct ggcagcctgg ccctcctggt    3900
gcccactccc gccagcccct gcctcgagga ctgatactgc agtgactgcc gtcagctccg    3960
actgccgctg agaagggttg atcctgcatc tgggtttgtt tacagcaatt cctggactcg    4020
ggggtatttt ggtcacaggg tggttttggt ttaggggtt tgtttgttgg ttgttttt    4080 gttttttggt tttttttaat gacaatgaag tgacactttg acatttccta ccttttgagg    4140
acttgatcct tctccaggaa gaaggtgctt tctgcttact gacttaggca atacaccaag    4200
ggcgagattt tatatgcaca tttctggatt tttttatacg gttttcattg acactcttcc    4260
ctcctcccac ctgccaccag gcctcaccaa agcccactgc catgggccca tctgggccat    4320
tcagagactg gagtgagatt tgggtgtgga ggggaggcg ccaaggtgga ggagcttccc    4380
actccaggac tgttgatgaa aggacagat tgaggaggaa gtgggctctg aggctgcagg    4440
```

-continued

```
gctggaagtc cttgcccact tcccactctc ctgccccaat ctatctagta cttcccaggc    4500
aaataggccc ctttgaggct cctgagtgcc ctcagatggt caaaacccag ttttccctct    4560
gggagcctaa accaggctgc atcggaggcc aggacccgga tcattcactg tgataccctg    4620
ccctccagag ggtgcgctca gagacacggg caagcatgcc tcttcccttc cctggagaga    4680
aagtgtgtga tttctctccc acctccttcc ccccaccaga cctttgctgg gcctaaaggt    4740
cttggccatg gggacgccct cagtctaggg atctggccac agactccctc ctgtgaacca    4800
acacagacac ccaagcagag caatcagtta gtgaattgaa tggaaataaa cgctttagtt    4860
ataatatga                                                            4869
```

```
<210> SEQ ID NO 2
<211> LENGTH: 987
<212> TYPE: PRT
<213> ORGANISM: Homo sapiens

<400> SEQUENCE: 2

Met Ala Leu Arg Arg Leu Gly Ala Ala Leu Leu Leu Pro Leu Leu
1               5                   10                  15

Ala Ala Val Glu Glu Thr Leu Met Asp Ser Thr Thr Ala Thr Ala Glu
                20                  25                  30

Leu Gly Trp Met Val His Pro Pro Ser Gly Trp Glu Glu Val Ser Gly
            35                  40                  45

Tyr Asp Glu Asn Met Asn Thr Ile Arg Thr Tyr Gln Val Cys Asn Val
        50                  55                  60

Phe Glu Ser Ser Gln Asn Asn Trp Leu Arg Thr Lys Phe Ile Arg Arg
65                  70                  75                  80

Arg Gly Ala His Arg Ile His Val Glu Met Lys Phe Ser Val Arg Asp
                85                  90                  95

Cys Ser Ser Ile Pro Ser Val Pro Gly Ser Cys Lys Glu Thr Phe Asn
            100                 105                 110

Leu Tyr Tyr Tyr Glu Ala Asp Phe Asp Ser Ala Thr Lys Thr Phe Pro
        115                 120                 125

Asn Trp Met Glu Asn Pro Trp Val Lys Val Asp Thr Ile Ala Ala Asp
    130                 135                 140

Glu Ser Phe Ser Gln Val Asp Leu Gly Gly Arg Val Met Lys Ile Asn
145                 150                 155                 160

Thr Glu Val Arg Ser Phe Gly Pro Val Ser Arg Ser Gly Phe Tyr Leu
                165                 170                 175

Ala Phe Gln Asp Tyr Gly Gly Cys Met Ser Leu Ile Ala Val Arg Val
            180                 185                 190

Phe Tyr Arg Lys Cys Pro Arg Ile Ile Gln Asn Gly Ala Ile Phe Gln
        195                 200                 205

Glu Thr Leu Ser Gly Ala Glu Ser Thr Ser Leu Val Ala Ala Arg Gly
    210                 215                 220

Ser Cys Ile Ala Asn Ala Glu Glu Val Asp Val Pro Ile Lys Leu Tyr
225                 230                 235                 240

Cys Asn Gly Asp Gly Glu Trp Leu Val Pro Ile Gly Arg Cys Met Cys
                245                 250                 255

Lys Ala Gly Phe Glu Ala Val Glu Asn Gly Thr Val Cys Arg Gly Cys
            260                 265                 270

Pro Ser Gly Thr Phe Lys Ala Asn Gln Gly Asp Glu Ala Cys Thr His
        275                 280                 285

Cys Pro Ile Asn Ser Arg Thr Thr Ser Glu Gly Ala Thr Asn Cys Val
```

```
              290                 295                 300
Cys Arg Asn Gly Tyr Tyr Arg Ala Asp Leu Asp Pro Leu Asp Met Pro
305                 310                 315                 320
Cys Thr Thr Ile Pro Ser Ala Pro Gln Ala Val Ile Ser Ser Val Asn
                325                 330                 335
Glu Thr Ser Leu Met Leu Glu Trp Thr Pro Pro Arg Asp Ser Gly Gly
                340                 345                 350
Arg Glu Asp Leu Val Tyr Asn Ile Ile Cys Lys Ser Cys Gly Ser Gly
                355                 360                 365
Arg Gly Ala Cys Thr Arg Cys Gly Asp Asn Val Gln Tyr Ala Pro Arg
                370                 375                 380
Gln Leu Gly Leu Thr Glu Pro Arg Ile Tyr Ile Ser Asp Leu Leu Ala
385                 390                 395                 400
His Thr Gln Tyr Thr Phe Glu Ile Gln Ala Val Asn Gly Val Thr Asp
                405                 410                 415
Gln Ser Pro Phe Ser Pro Gln Phe Ala Ser Val Asn Ile Thr Thr Asn
                420                 425                 430
Gln Ala Ala Pro Ser Ala Val Ser Ile Met His Gln Val Ser Arg Thr
                435                 440                 445
Val Asp Ser Ile Thr Leu Ser Trp Ser Gln Pro Asp Gln Pro Asn Gly
                450                 455                 460
Val Ile Leu Asp Tyr Glu Leu Gln Tyr Glu Lys Glu Leu Ser Glu
465                 470                 475                 480
Tyr Asn Ala Thr Ala Ile Lys Ser Pro Thr Asn Thr Val Thr Val Gln
                485                 490                 495
Gly Leu Lys Ala Gly Ala Ile Tyr Val Phe Gln Val Arg Ala Arg Thr
                500                 505                 510
Val Ala Gly Tyr Gly Arg Tyr Ser Gly Lys Met Tyr Phe Gln Thr Met
                515                 520                 525
Thr Glu Ala Glu Tyr Gln Thr Ser Ile Gln Glu Lys Leu Pro Leu Ile
                530                 535                 540
Ile Gly Ser Ser Ala Ala Gly Leu Val Phe Leu Ile Ala Val Val Val
545                 550                 555                 560
Ile Ala Ile Val Cys Asn Arg Arg Gly Phe Glu Arg Ala Asp Ser
                565                 570                 575
Glu Tyr Thr Asp Lys Leu Gln His Tyr Thr Ser Gly His Met Thr Pro
                580                 585                 590
Gly Met Lys Ile Tyr Ile Asp Pro Phe Thr Tyr Glu Asp Pro Asn Glu
                595                 600                 605
Ala Val Arg Glu Phe Ala Lys Glu Ile Asp Ile Ser Cys Val Lys Ile
                610                 615                 620
Glu Gln Val Ile Gly Ala Gly Glu Phe Gly Glu Val Cys Ser Gly His
625                 630                 635                 640
Leu Lys Leu Pro Gly Lys Arg Glu Ile Phe Val Ala Ile Lys Thr Leu
                645                 650                 655
Lys Ser Gly Tyr Thr Glu Lys Gln Arg Arg Asp Phe Leu Ser Glu Ala
                660                 665                 670
Ser Ile Met Gly Gln Phe Asp His Pro Asn Val Ile His Leu Glu Gly
                675                 680                 685
Val Val Thr Lys Ser Thr Pro Val Met Ile Ile Thr Glu Phe Met Glu
                690                 695                 700
Asn Gly Ser Leu Asp Ser Phe Leu Arg Gln Asn Asp Gly Gln Phe Thr
705                 710                 715                 720
```

```
Val Ile Gln Leu Val Gly Met Leu Arg Gly Ile Ala Ala Gly Met Lys
                725                 730                 735

Tyr Leu Ala Asp Met Asn Tyr Val His Arg Asp Leu Ala Ala Arg Asn
                740                 745                 750

Ile Leu Val Asn Ser Asn Leu Val Cys Lys Val Ser Asp Phe Gly Leu
                755                 760                 765

Ser Arg Phe Leu Glu Asp Asp Thr Ser Asp Pro Thr Tyr Thr Ser Ala
770                 775                 780

Leu Gly Gly Lys Ile Pro Ile Arg Trp Thr Ala Pro Glu Ala Ile Gln
785                 790                 795                 800

Tyr Arg Lys Phe Thr Ser Ala Ser Asp Val Trp Ser Tyr Gly Ile Val
                805                 810                 815

Met Trp Glu Val Met Ser Tyr Gly Glu Arg Pro Tyr Trp Asp Met Thr
                820                 825                 830

Asn Gln Asp Val Ile Asn Ala Ile Glu Gln Asp Tyr Arg Leu Pro Pro
                835                 840                 845

Pro Met Asp Cys Pro Ser Ala Leu His Gln Leu Met Leu Asp Cys Trp
            850                 855                 860

Gln Lys Asp Arg Asn His Arg Pro Lys Phe Gly Gln Ile Val Asn Thr
865                 870                 875                 880

Leu Asp Lys Met Ile Arg Asn Pro Asn Ser Leu Lys Ala Met Ala Pro
                885                 890                 895

Leu Ser Ser Gly Ile Asn Leu Pro Leu Leu Asp Arg Thr Ile Pro Asp
            900                 905                 910

Tyr Thr Ser Phe Asn Thr Val Asp Glu Trp Leu Glu Ala Ile Lys Met
                915                 920                 925

Gly Gln Tyr Lys Glu Ser Phe Ala Asn Ala Gly Phe Thr Ser Phe Asp
930                 935                 940

Val Val Ser Gln Met Met Met Glu Asp Ile Leu Arg Val Gly Val Thr
945                 950                 955                 960

Leu Ala Gly His Gln Lys Lys Ile Leu Asn Ser Ile Gln Val Met Arg
                965                 970                 975

Ala Gln Met Asn Gln Ile Gln Ser Val Glu Val
                980                 985

<210> SEQ ID NO 3
<211> LENGTH: 986
<212> TYPE: PRT
<213> ORGANISM: Rattus norvegicus

<400> SEQUENCE: 3

Met Ala Val Arg Arg Leu Gly Ala Ala Leu Leu Leu Pro Leu Leu
1               5                   10                  15

Ala Ala Val Glu Glu Thr Leu Met Asp Ser Thr Thr Ala Thr Ala Glu
                20                  25                  30

Leu Gly Trp Met Val His Pro Pro Ser Gly Trp Glu Glu Val Ser Gly
                35                  40                  45

Tyr Asp Glu Asn Met Asn Thr Ile Arg Thr Tyr Gln Val Cys Asn Val
            50                  55                  60

Phe Glu Ser Ser Gln Asn Asn Trp Leu Arg Thr Lys Phe Ile Arg Arg
65                  70                  75                  80

Arg Gly Ala His Arg Ile His Val Glu Met Lys Phe Ser Val Arg Asp
                85                  90                  95

Cys Ser Ser Ile Pro Ser Val Pro Gly Ser Cys Lys Glu Thr Phe Asn
```

```
            100             105              110
Leu Tyr Tyr Tyr Glu Ala Asp Phe Asp Leu Ala Thr Lys Thr Phe Pro
            115             120              125

Asn Trp Met Glu Asn Pro Trp Val Lys Val Asp Thr Ile Ala Ala Asp
            130             135              140

Glu Ser Phe Ser Gln Val Asp Leu Gly Gly Arg Val Met Lys Ile Asn
145             150             155              160

Thr Glu Val Arg Ser Phe Gly Pro Val Ser Arg Asn Gly Phe Tyr Leu
                165             170              175

Ala Phe Gln Asp Tyr Gly Gly Cys Met Ser Leu Ile Ala Val Arg Val
            180             185              190

Phe Tyr Arg Lys Cys Pro Arg Val Ile Gln Asn Gly Ala Ile Phe Gln
            195             200              205

Glu Thr Leu Ser Gly Ala Glu Ser Thr Ser Leu Val Ala Ala Arg Gly
            210             215              220

Ser Cys Ile Ala Asn Ala Glu Glu Val Asp Val Pro Ile Lys Leu Tyr
225             230             235              240

Cys Asn Gly Asp Gly Glu Trp Leu Val Pro Ile Gly Arg Cys Met Cys
                245             250              255

Lys Ala Gly Phe Glu Ala Val Glu Asn Gly Thr Val Cys Arg Gly Cys
            260             265              270

Pro Ser Gly Thr Phe Lys Ala Asn Gln Gly Asp Glu Ala Cys Thr His
            275             280              285

Cys Pro Ile Asn Ser Arg Thr Thr Ser Glu Gly Ala Thr Asn Cys Val
            290             295              300

Cys Arg Asn Gly Tyr Tyr Arg Ala Asp Leu Asp Pro Leu Asp Met Pro
305             310             315              320

Cys Thr Thr Ile Pro Ser Ala Pro Gln Ala Val Ile Ser Ser Val Asn
                325             330              335

Glu Thr Ser Leu Val Leu Glu Trp Thr Pro Pro Arg Asp Ser Gly Gly
            340             345              350

Arg Glu Asp Leu Val Tyr Asn Ile Ile Cys Lys Ser Cys Gly Ser Gly
            355             360              365

Arg Gly Ala Cys Thr Arg Cys Gly Asp Asn Val Gln Tyr Ala Pro Arg
            370             375              380

Gln Leu Gly Leu Thr Glu Pro Arg Ile Tyr Ile Ser Asp Leu Leu Ala
385             390             395              400

His Thr Gln Tyr Thr Phe Glu Ile Gln Ala Val Asn Gly Val Thr Asp
                405             410              415

Gln Ser Pro Phe Ser Pro Gln Phe Ala Ser Val Asn Ile Thr Thr Asn
            420             425              430

Gln Ala Ala Pro Ser Ala Val Ser Ile Met His Gln Val Ser Arg Thr
            435             440              445

Val Asp Ser Ile Thr Leu Ser Trp Ser Gln Pro Asp Gln Pro Asn Gly
450             455             460

Val Ile Leu Asp Tyr Glu Leu Gln Tyr Tyr Glu Lys Glu Leu Ser Glu
465             470             475              480

Tyr Asn Ala Thr Ala Ile Lys Ser Pro Thr Asn Thr Val Thr Val Gln
                485             490              495

Gly Leu Lys Ala Gly Thr Ile Tyr Val Phe Gln Val Arg Ala Arg Thr
            500             505              510

Val Ala Gly Tyr Gly Arg Tyr Ser Gly Lys Met Tyr Phe Gln Thr Met
            515             520              525
```

```
Thr Glu Ala Glu Tyr Gln Thr Ser Ile Lys Glu Lys Leu Pro Leu Ile
        530                 535                 540
Val Gly Ser Ser Ala Ala Gly Val Val Phe Ile Ala Val Val
545                 550                 555                 560
Ile Ala Ile Val Cys Asn Arg Arg Gly Phe Glu Arg Ala Asp Ser Glu
                565                 570                 575
Tyr Thr Asp Lys Leu Gln His Tyr Thr Ser Gly His Met Thr Pro Gly
                580                 585                 590
Met Lys Ile Tyr Ile Asp Pro Phe Thr Tyr Glu Asp Pro Asn Glu Ala
                595                 600                 605
Val Arg Glu Phe Ala Lys Glu Ile Asp Ile Ser Cys Val Lys Ile Glu
610                 615                 620
Gln Val Ile Gly Ala Gly Glu Phe Gly Glu Val Cys Ser Gly His Leu
625                 630                 635                 640
Lys Leu Pro Gly Lys Arg Glu Ile Phe Val Ala Ile Lys Thr Leu Lys
                645                 650                 655
Ser Gly Tyr Thr Glu Lys Gln Arg Arg Asp Phe Leu Ser Glu Ala Ser
                660                 665                 670
Ile Met Gly Gln Phe Asp His Pro Asn Val Ile His Leu Glu Gly Val
                675                 680                 685
Val Thr Lys Ser Thr Pro Val Met Ile Ile Thr Glu Phe Met Glu Asn
690                 695                 700
Gly Ser Leu Asp Ser Phe Leu Arg Gln Asn Asp Gly Gln Phe Thr Val
705                 710                 715                 720
Ile Gln Leu Val Gly Met Leu Arg Gly Ile Ala Ala Gly Met Lys Tyr
                725                 730                 735
Leu Ala Asp Met Asn Tyr Val His Arg Asp Leu Ala Ala Arg Asn Ile
                740                 745                 750
Leu Val Asn Ser Asn Leu Val Cys Lys Val Ser Asp Phe Gly Leu Ser
                755                 760                 765
Arg Phe Leu Glu Asp Asp Thr Ser Asp Pro Thr Tyr Thr Ser Ala Leu
                770                 775                 780
Gly Gly Lys Ile Pro Ile Arg Trp Thr Ala Pro Glu Ala Ile Gln Tyr
785                 790                 795                 800
Arg Lys Phe Thr Ser Ala Ser Asp Val Trp Ser Tyr Gly Ile Val Met
                805                 810                 815
Trp Glu Val Met Ser Tyr Gly Glu Arg Pro Tyr Trp Asp Met Thr Asn
                820                 825                 830
Gln Asp Val Ile Asn Ala Ile Glu Gln Asp Tyr Arg Leu Pro Pro Pro
                835                 840                 845
Met Asp Cys Pro Ser Ala Leu His Gln Leu Met Leu Asp Cys Trp Gln
850                 855                 860
Lys Asp Arg Asn His Arg Pro Lys Phe Gly Gln Ile Val Asn Thr Leu
865                 870                 875                 880
Asp Lys Met Ile Arg Asn Pro Asn Ser Leu Lys Ala Met Ala Pro Leu
                885                 890                 895
Ser Ser Gly Ile Asn Leu Pro Leu Leu Asp Arg Thr Ile Pro Asp Tyr
                900                 905                 910
Thr Ser Phe Asn Thr Val Asp Glu Trp Leu Glu Ala Ile Lys Met Gly
                915                 920                 925
Gln Tyr Lys Glu Ser Phe Thr Asn Ala Gly Phe Thr Ser Phe Asp Val
                930                 935                 940
```

-continued

```
Val Ser Gln Met Met Met Glu Asp Ile Leu Arg Val Gly Val Thr Leu
945                 950                 955                 960

Ala Gly His Gln Lys Lys Ile Leu Asn Ser Ile Gln Val Met Arg Ala
            965                 970                 975

Gln Met Asn Gln Ile Gln Ser Val Glu Val
            980                 985

<210> SEQ ID NO 4
<211> LENGTH: 1012
<212> TYPE: PRT
<213> ORGANISM: Pan troglodytes

<400> SEQUENCE: 4

Met Glu Asp Leu Ser Cys Leu Gly Leu Gly Leu Cys Glu Gln Asn Leu
1               5                   10                  15

Gly Tyr Ile Leu Arg Asp Gly Leu Gly Pro Arg Gly Phe Leu Gln Leu
            20                  25                  30

Leu Glu Ser Gly Glu Ala Ser Gly Ala Gln Asp Gly Pro Glu Thr Leu
        35                  40                  45

Met Asp Ser Thr Thr Ala Thr Ala Glu Leu Gly Trp Met Val His Pro
    50                  55                  60

Pro Ser Gly Trp Glu Glu Val Ser Gly Tyr Asp Glu Asn Met Asn Thr
65                  70                  75                  80

Ile Arg Thr Tyr Gln Val Cys Asn Val Phe Glu Ser Ser Gln Asn Asn
                85                  90                  95

Trp Leu Arg Thr Lys Phe Ile Arg Arg Gly Ala His Arg Ile His
            100                 105                 110

Val Glu Met Lys Phe Ser Val Arg Asp Cys Ser Ser Ile Pro Ser Val
        115                 120                 125

Pro Gly Ser Cys Lys Glu Thr Phe Asn Leu Tyr Tyr Tyr Glu Ala Asp
    130                 135                 140

Phe Asp Ser Ala Thr Lys Thr Phe Pro Asn Trp Met Glu Asn Pro Trp
145                 150                 155                 160

Val Lys Val Asp Thr Ile Ala Ala Asp Glu Ser Phe Ser Gln Val Asp
                165                 170                 175

Leu Gly Gly Arg Val Met Lys Ile Asn Thr Glu Val Arg Ser Phe Gly
            180                 185                 190

Pro Val Ser Arg Ser Gly Phe Tyr Leu Ala Phe Gln Asp Tyr Gly Gly
        195                 200                 205

Cys Met Ser Leu Ile Ala Val Arg Val Phe Tyr Arg Lys Cys Pro Arg
    210                 215                 220

Ile Ile Gln Asn Gly Ala Ile Phe Gln Glu Thr Leu Ser Gly Ala Glu
225                 230                 235                 240

Ser Thr Ser Leu Val Ala Ala Arg Gly Ser Cys Ile Ala Asn Ala Glu
                245                 250                 255

Glu Val Asp Val Pro Ile Lys Leu Tyr Cys Asn Gly Asp Gly Glu Trp
            260                 265                 270

Leu Val Pro Ile Gly Arg Cys Met Cys Lys Ala Gly Phe Glu Ala Val
        275                 280                 285

Glu Asn Gly Thr Val Cys Arg Gly Cys Pro Ser Gly Thr Phe Lys Ala
    290                 295                 300

Asn Gln Gly Asp Glu Ala Cys Thr His Cys Pro Ile Asn Ser Arg Thr
305                 310                 315                 320

Thr Ser Glu Gly Ala Thr Asn Cys Val Cys Arg Asn Gly Tyr Tyr Arg
                325                 330                 335
```

-continued

```
Ala Asp Leu Asp Pro Leu Asp Met Pro Cys Thr Thr Ile Pro Ser Ala
            340                 345                 350

Pro Gln Ala Val Ile Ser Ser Val Asn Glu Thr Ser Leu Met Leu Glu
            355                 360                 365

Trp Thr Pro Pro Arg Asp Ser Gly Gly Arg Glu Asp Leu Val Tyr Asn
    370                 375                 380

Ile Ile Cys Lys Ser Cys Gly Ser Gly Arg Gly Ala Cys Thr Arg Cys
385                 390                 395                 400

Gly Asp Asn Val Gln Tyr Ala Pro Arg Gln Leu Gly Leu Thr Glu Pro
                405                 410                 415

Arg Ile Tyr Ile Ser Asp Leu Leu Ala His Thr Gln Tyr Thr Phe Glu
            420                 425                 430

Ile Gln Ala Val Asn Gly Val Thr Asp Gln Ser Pro Phe Ser Pro Gln
            435                 440                 445

Phe Ala Ser Val Asn Ile Thr Thr Asn Gln Ala Ala Pro Ser Ala Val
    450                 455                 460

Ser Ile Met His Gln Val Ser Arg Thr Val Asp Ser Ile Thr Leu Ser
465                 470                 475                 480

Trp Ser Gln Pro Asp Gln Pro Asn Gly Val Ile Leu Asp Tyr Glu Leu
                485                 490                 495

Gln Tyr Tyr Glu Lys Glu Leu Ser Glu Tyr Asn Ala Thr Ala Ile Lys
            500                 505                 510

Ser Pro Thr Asn Thr Val Thr Val Gln Gly Leu Lys Ala Gly Ala Ile
            515                 520                 525

Tyr Val Phe Gln Val Arg Ala Arg Thr Val Ala Gly Tyr Gly Arg Tyr
    530                 535                 540

Ser Gly Lys Met Tyr Phe Gln Thr Met Thr Glu Ala Glu Tyr Gln Thr
545                 550                 555                 560

Ser Ile Gln Glu Lys Leu Pro Leu Ile Ile Gly Ser Ser Ala Ala Gly
                565                 570                 575

Leu Val Phe Leu Ile Ala Val Val Ile Ala Ile Val Cys Asn Arg
            580                 585                 590

Arg Arg Gly Phe Glu Arg Ala Asp Ser Glu Tyr Thr Asp Lys Leu Gln
    595                 600                 605

His Tyr Thr Ser Gly His Met Thr Pro Gly Met Lys Ile Tyr Ile Asp
610                 615                 620

Pro Phe Thr Tyr Glu Asp Pro Asn Glu Ala Val Arg Glu Phe Ala Lys
625                 630                 635                 640

Glu Ile Asp Ile Ser Cys Val Lys Ile Glu Gln Val Ile Gly Ala Gly
                645                 650                 655

Glu Phe Gly Glu Val Cys Ser Gly His Leu Lys Leu Pro Gly Lys Arg
            660                 665                 670

Glu Ile Phe Val Ala Ile Lys Thr Leu Lys Ser Gly Tyr Thr Glu Lys
            675                 680                 685

Gln Arg Arg Asp Phe Leu Ser Glu Ala Ser Ile Met Gly Gln Phe Asp
    690                 695                 700

His Pro Asn Val Ile His Leu Glu Gly Val Val Thr Lys Ser Thr Pro
705                 710                 715                 720

Val Met Ile Ile Thr Glu Phe Met Glu Asn Gly Ser Leu Asp Ser Phe
                725                 730                 735

Leu Arg Gln Asn Asp Gly Gln Phe Thr Val Ile Gln Leu Val Gly Met
            740                 745                 750
```

-continued

```
Leu Arg Gly Ile Ala Ala Gly Met Lys Tyr Leu Ala Asp Met Asn Tyr
            755                 760                 765

Val His Arg Asp Leu Ala Ala Arg Asn Ile Leu Val Asn Ser Asn Leu
    770                 775                 780

Val Cys Lys Val Ser Asp Phe Gly Leu Ser Arg Phe Leu Glu Asp Asp
785                 790                 795                 800

Thr Ser Asp Pro Thr Tyr Thr Ser Ala Leu Gly Gly Lys Ile Pro Ile
                805                 810                 815

Arg Trp Thr Ala Pro Glu Ala Ile Gln Tyr Arg Lys Phe Thr Ser Ala
            820                 825                 830

Ser Asp Val Trp Ser Tyr Gly Ile Val Met Trp Glu Val Met Ser Tyr
        835                 840                 845

Gly Glu Arg Pro Tyr Trp Asp Met Thr Asn Gln Asp Val Ile Asn Ala
    850                 855                 860

Ile Glu Gln Asp Tyr Arg Leu Pro Pro Met Asp Cys Pro Ser Ala
865                 870                 875                 880

Leu His Gln Leu Met Leu Asp Cys Trp Gln Lys Asp Arg Asn His Arg
                885                 890                 895

Pro Lys Phe Gly Gln Ile Val Asn Thr Leu Asp Lys Met Ile Arg Asn
            900                 905                 910

Pro Asn Ser Leu Lys Ala Met Ala Pro Leu Ser Ser Gly Ile Asn Leu
        915                 920                 925

Pro Leu Leu Asp Arg Thr Ile Pro Asp Tyr Thr Ser Phe Asn Thr Val
    930                 935                 940

Asp Glu Trp Leu Glu Ala Ile Lys Met Gly Gln Tyr Lys Glu Ser Phe
945                 950                 955                 960

Ala Asn Ala Gly Phe Thr Ser Phe Asp Val Val Ser Gln Met Met Met
                965                 970                 975

Glu Asp Ile Leu Arg Val Gly Val Thr Leu Ala Gly His Gln Lys Lys
            980                 985                 990

Ile Leu Asn Ser Ile Gln Val Met  Arg Ala Gln Met Asn  Gln Ile Gln
            995                1000                1005

Ser Val  Glu Val
   1010

<210> SEQ ID NO 5
<211> LENGTH: 42
<212> TYPE: PRT
<213> ORGANISM: Artificial Sequence
<220> FEATURE:
<223> OTHER INFORMATION: Synthetic polypeptide

<400> SEQUENCE: 5

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
            35                  40

<210> SEQ ID NO 6
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 6
```

```
Cys Tyr Pro Tyr Asp Val Pro Asp Tyr Ala
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 7

Asp Tyr Lys Asp Asp Asp Asp Lys
1               5

<210> SEQ ID NO 8
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 8

Cys Glu Gln Lys Leu Ile Ser Glu Glu Asp Leu
1               5                   10

<210> SEQ ID NO 9
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 9
acgagaacat gaacactat                                              19

<210> SEQ ID NO 10
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 10
tgaacagtat ccaggtgat                                              19

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
gtgtggagct atggcatcgt                                             20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
tgggcggagg tagtctgtag                                             20
```

```
<210> SEQ ID NO 13
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 13
tgcaatgtct ttgagtcaa                                          19

<210> SEQ ID NO 14
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 14
atgcggtggg cgcc                                               14

<210> SEQ ID NO 15
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 15
atcaactttc gatggtagtc g                                       21

<210> SEQ ID NO 16
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 16
tccttggatg tggtagccg                                          19

<210> SEQ ID NO 17
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 17
cgttgctgtc gtagagtcc                                          19

<210> SEQ ID NO 18
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 18
attctgctgg ctgctgct                                           18
```